US007592006B1

(12) United States Patent
Bazin et al.

(10) Patent No.: US 7,592,006 B1
(45) Date of Patent: *Sep. 22, 2009

(54) COMPOSITION COMPRISING THE LO-CD2A ANTIBODY

(75) Inventors: Herve Bazin, Brussels (BE); Dominique Latinne, Brussels (BE)

(73) Assignee: Université Catholique de Louvain, Louvain-la-Neuve (BE)

( * ) Notice: Subject to any disclaimer, the term of this patent is extended or adjusted under 35 U.S.C. 154(b) by 0 days.

This patent is subject to a terminal disclaimer.

(21) Appl. No.: 09/056,072

(22) Filed: Apr. 7, 1998

Related U.S. Application Data

(63) Continuation of application No. 08/472,281, filed on Jun. 7, 1995, now Pat. No. 5,817,311, which is a continuation-in-part of application No. 08/407,009, filed on Mar. 29, 1995, now abandoned, which is a continuation-in-part of application No. 08/119,032, filed on Sep. 9, 1993, now abandoned, which is a continuation-in-part of application No. 08/027,008, filed on Mar. 5, 1993, now abandoned.

(51) Int. Cl.
*A61K 39/395* (2006.01)
*C07K 16/28* (2006.01)

(52) U.S. Cl. .............. 424/154.1; 424/130.1; 424/133.1; 424/141.1; 424/143.1; 424/144.1; 424/153.1; 424/173.1; 530/387.1; 530/387.3; 530/388.1; 530/388.2; 530/388.22; 530/388.7; 530/388.73; 530/388.75

(58) Field of Classification Search ... 424/130.1–133.1, 424/144.1, 153.1; 435/70.21, 326, 343, 346; 530/387.1, 388.22, 388.75

See application file for complete search history.

(56) References Cited

U.S. PATENT DOCUMENTS

| 5,283,058 | A | * | 2/1994 | Faustman | |
|---|---|---|---|---|---|
| 5,530,101 | A | * | 6/1996 | Queen et al. | |
| 5,658,570 | A | * | 8/1997 | Newman et al. | |
| 5,730,979 | A | * | 3/1998 | Bazin et al. | |
| 5,817,311 | A | * | 10/1998 | Bazin et al. | 424/154.1 |
| 5,951,983 | A | * | 9/1999 | Bazin et al. | 424/154.1 |
| 6,849,258 | B1 | * | 2/2005 | Bazin et al. | 424/154.1 |

FOREIGN PATENT DOCUMENTS

WO WO91/01752 2/1991

OTHER PUBLICATIONS

Xia et al. In Rat Hybridomas and Rat Monoclonal Antibodies, Ravott et al. (Ed) CRC Press Inc. Boca Raton Florida 1990 pp. 309-322.*
Guckel et al. J. Exp Med. 174: 957-967 (1991).*
Bromberg et al. Transplantation 51: 219-225 (1991).*
Hafler et a. J. Immunol. 141:131-138 (1988).*
Chavin et al. Transplantation 54: 286-291 (1996).*
Olive et al., Leucocyte Typing III, edited by McMichael et al., Oxford University Press, Oxford, 1987; see pp. 148-153.*
Denning et al., Leucocyte Typing III, edited by McMichael et al., Oxford University Press, Oxford, 1987; see pp. 144-147.*
Xu et al., Clin. Exp. Immunol. 138: 476-483, 2004.*
Wallace et al. Leucocyte Typing III, edited by McMichael et al., Oxford University Press, Oxford, Great Britain, 1987; pp. 120-123.*
Jonker, et al., *Transplantation Proceedings*, vol. 15, No. 1, pp. 635-638 (Mar. 1983).
Remlinger, et al., *Human Immunology*, vol. 9, pp. 21-35 (1984).
Martin, et al., *Transplantation Proceedings*, vol. 16, No. 6 (Dec. 1984).
Jonker, et al., *Transplantation*, vol. 45, No. 4, pp. 677-682 (Apr. 1988).
Trinchieri, *Advances in Immunology*, vol. 47, pp. 272-303 (1989).
Auchincloss, et al., *Fundamental Immunology*, Paul, ed., Raven Press Ltd., New York, pp. 889-922 (1989).
Sharabi, et al., *J. Exp. Med.*, vol. 172, pp. 195-202 (Jul. 1990).
Bollinger, et al., *Transplantation Proceedings*, vol. 23, No. 1, pp. 587-588 (Feb. 1991).
DeLaParra, et al. *Belg. J. Zoology*, vol. 121, Supp. 1, p. 13 (Nov. 1991).
Berlin, et al., *Transplantation*, vol. 53, No. 4, pp. 840-849 (Apr. 1992).
Edgington, et al. *Biotechnology*, vol. 10, pp. 383-389 (Apr. 1992).
Kahan, *Curr. Opin. in Immunol.*, vol. 4, pp. 553-560 (Aug. 1992).
Monaco, *Immunomethods*, vol. 2, pp. 159-170 (1993).
Berzofsky, et al., *Fundamental Immunology*, Paul, ed., Raven Press Ltd., New York, p. 242 (1993).
Harris, et al., *Tibtech*, vol. 11, pp. 42-44 (Feb. 1993).
Rebellato, et al., *Transplantation Proceedings*, vol. 25, No. 1, pp. 598-599 (Feb. 1993).
Emery, et al., *Exp. Opin. Invest. Drugs*, vol. 3, No. 3, pp. 241-251 (1994).

* cited by examiner

*Primary Examiner*—Phillip Gambel
(74) *Attorney, Agent, or Firm*—Elliot M. Olstein; Raymond J. Lillie

(57) ABSTRACT

The present invention relates to a LO-CD2a antibody and methods of using such antibodies or molecules that bind to the same epitope (or a portion thereof) to prevent and inhibit an immune response in human patients, preferably, where the immune response is mediated by the activation and proliferation of T cells or natural killer cells. The administration of an effective amount of the LO-CD2a antibody to a human patient will prevent or inhibit graft rejection, graft versus host disease or autoimmune disease.

2 Claims, 62 Drawing Sheets

Figure 1:
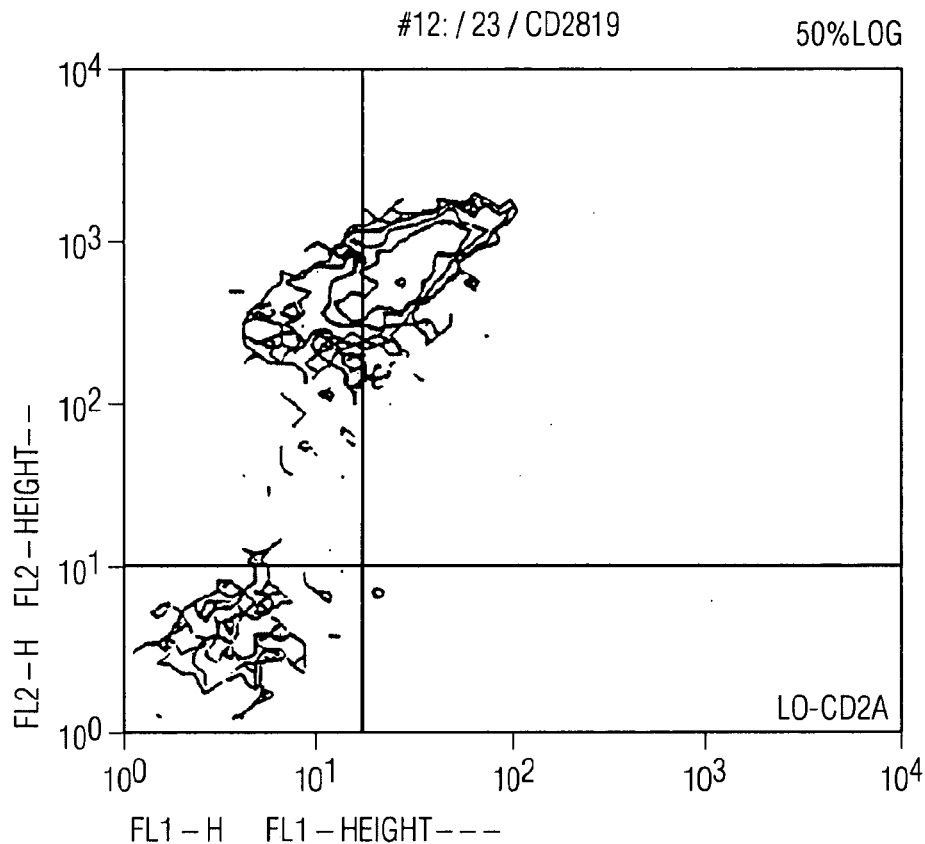

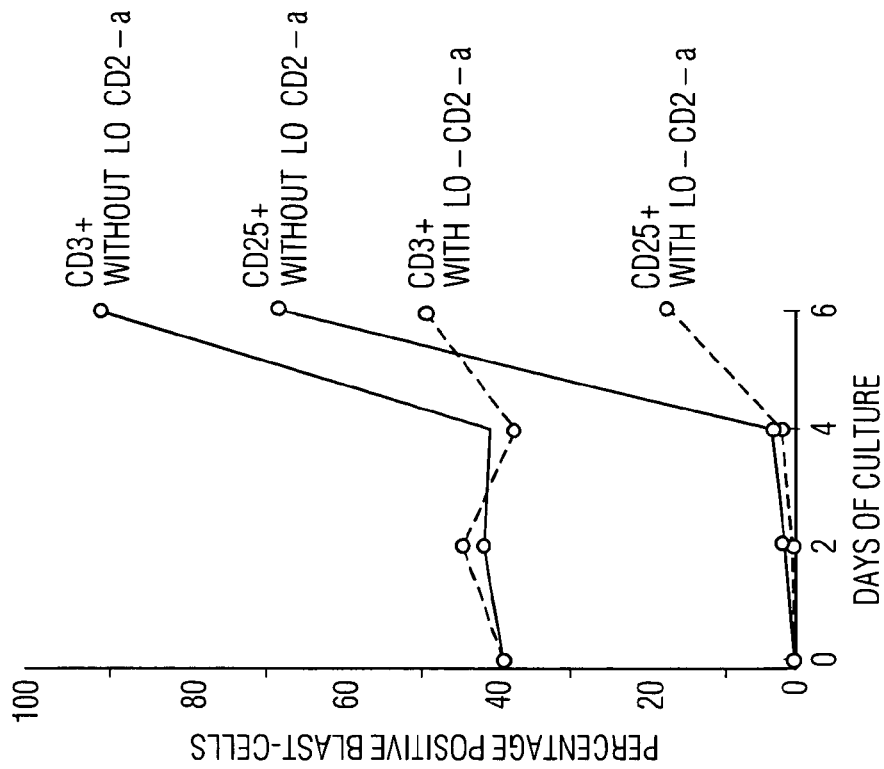
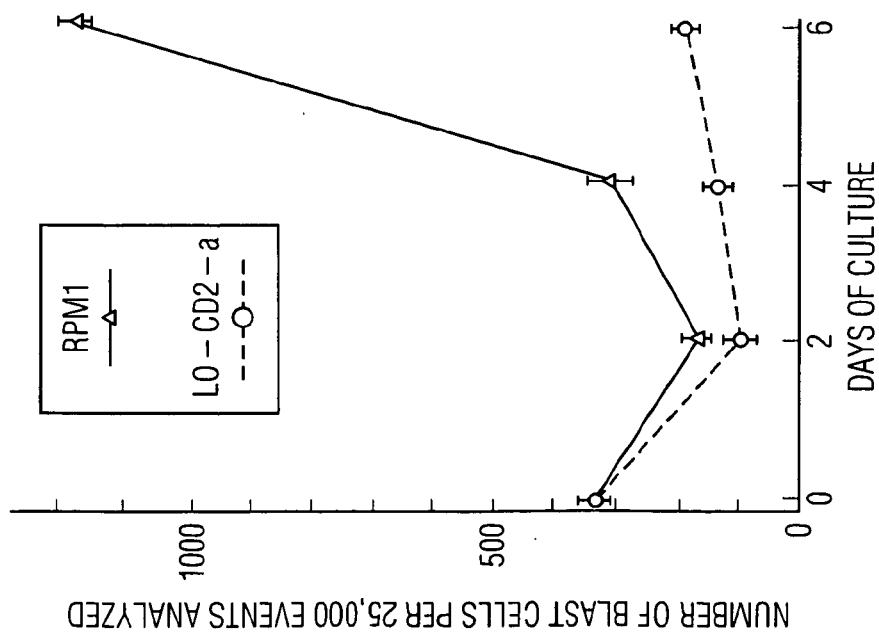
FIG. 7A
FIG. 7B

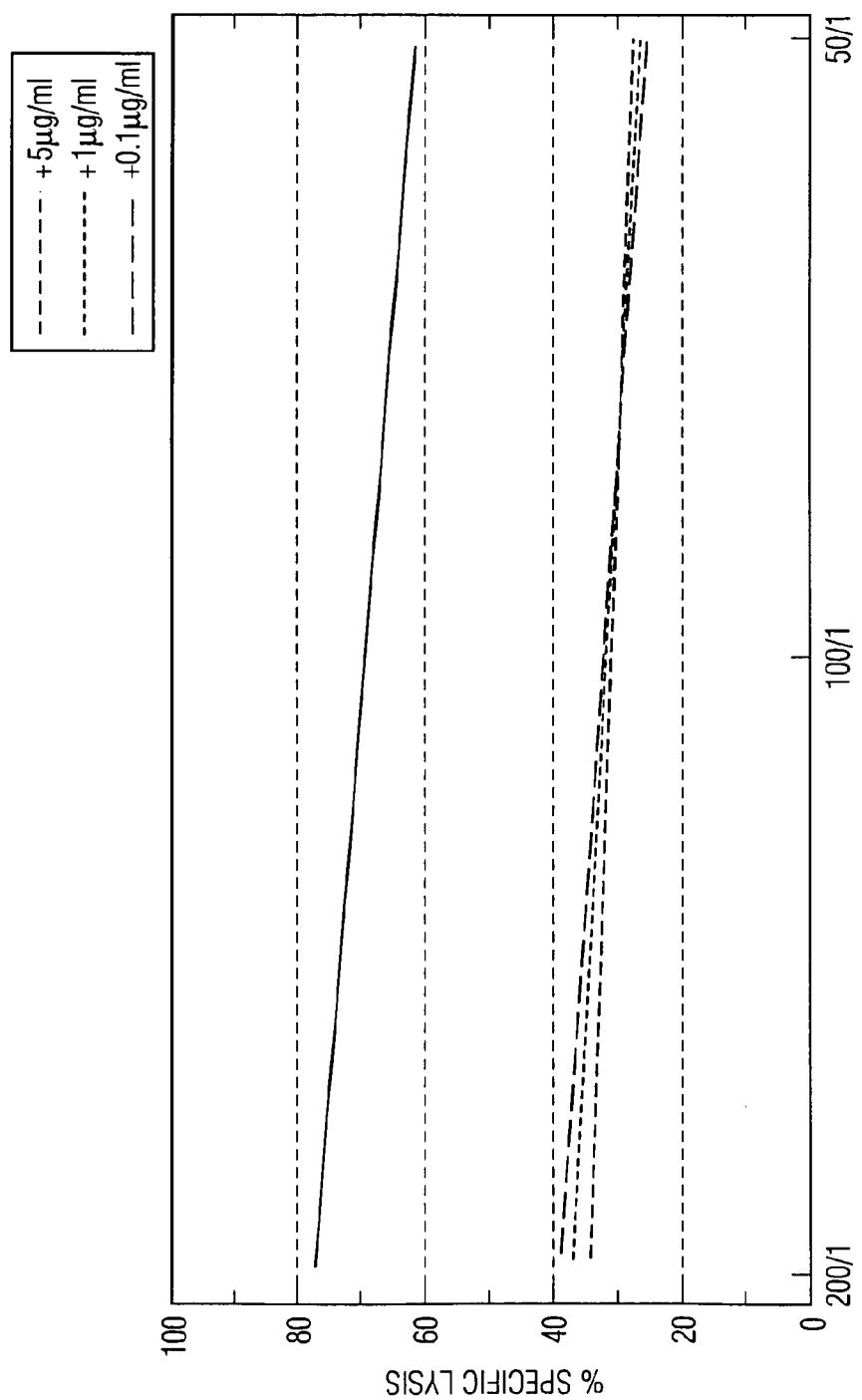

```
         10         20          30
         *          *           *
ATGATGAGTCCTGTCCAGTCCCTGTTTCTGTTATT
 M  M  S  P  V  Q  S  L  F  L  L  L 110        120         130
         *          *           *
GACTGCCCATGTTGGCTGTCCATGTGTGGTAAGGC 210        220         230
         *          *           *
ATAGGATTTGTGCTAAGAGGATTCTAATGTAGATG 310        320         330
         *          *           *
TTAAAAATCACAAAACACACCGGGATCTCACAGGA 410        420         430
         *          *           *
TATTATAATTTCAGGAACCAATGGTGATGTTGTGC
                    T  N  G  D  V  V 510        520         530
         *          *           *
AGTCAGAGTCTCTTACATAGTAGTGGAAACACCTA
 S  Q  S  L  L  H  S  S  G  N  T  Y 610        620         630
         *          *           *
TGGAATCTGGGGTCCCCAACAGGTTCAGTGGCAGT
 L  E  S  G  V  P  N  R  F  S  G  S 710        720         730
         *          *           *
CTGCATGCAATTTACCCATTATCCGTATACGTTTG
 C  M  Q  F  T  H  Y  P  Y  T  F
```

FIG. 29A

```
        40         50         60         70
         *    *    *    *    *    *    *
  GCTTTGGATTCTGGGTAAGTAGAGAATGAGTTACA
   L  W  I  L  G 140        150        160        170
         *    *    *    *    *    *    *
  AGGTCCTATTTCTAAGATGGACACTTGAGATTCC 240        250        260        270
         *    *    *    *    *    *    *
  AGAAGGTGTATGCCATTTAGGATCTGCAACCGAAT 340        350        360        370
         *    *    *    *    *    *    *
  AATGAGTAACAAAAGTAATTCACAAAGATTGGTT 440        450        460        470
         *    *    *    *    *    *    *
  TGACCCAGACTCCACCTACTTTATTGGCTACCATT
   L  T  Q  T  P  P  T  L  L  A  T  I 540        550        560        570
         *    *    *    *    *    *    *
  TTTAAATTGGTTGCTACAGAGGACAGGCCAATCTC
   L  N  W  L  L  Q  R  T  G  Q  S 640        650        660        670
         *    *    *    *    *    *    *
  GGGTCAGGAACAGATTTCACACTCAAAATCAGTGG
   G  S  G  T  D  F  T  L  K  I  S  G 740        750        760
         *    *    *    *    *
  GAGCTGGGACCAAGCTGGAACTGAAA
   G  A  G  T  K  L  E  L  K>
```

FIG. 29B

```
                80            90           100
        *      *      *      *      *      *
        GGACAAGAATGGGGATGGAGGATGAGTTCT 180           190          200
        *      *      *      *      *      *
        ATTACTTGATAATGAGAAATTACAGATGAG 280           290          300
        *      *      *      *      *      *
        TGTTTTGTGAAAAGCATTTGGTATATTTT 380           390          400
        *      *      *      *      *      *
        GCAAATTTTGCACATAACTTTGTTCTGATC 480           490          500
        *      *      *      *      *      *
        GGACAATCAGTCTCCATCTCTTGCAGGTCA
         G  Q  S  V  S  I  S  C  R  S>

580           590          600
        *      *      *      *      *      *
        CACAGCCGCTAATTTATTTGGTATCCAAAC
         P  Q  P  L  I  Y  L  V  S  K>

680           690          700
        *      *      *      *      *      *
        AGTGGAAGTTGAGGATTTGGGGGTTTATTA
         V  E  A  E  D  L  G  V  Y  Y>
```

FIG. 29C

```
          10         20         30         40
           *          *          *          *
ATGAAATGCAGGTGGATCATCTTCTTCTTGATGGCAGTAGCTACAG
 M  K  C  R  W  I  I  L  L  L  M  A  V  A  T 110        120        130        140
           *          *          *          *
CACTATCTTTGGATTTCTTGCAACAGGGTCAACTCAGAAGTTCAG
    Y  L  W  I  S  C  N  R  V  N  S  E  V  Q 210        220        230        240
           *          *          *          *
TGCAAGGCTTCTGGCTATATATTTATAGAATACTATATGTACTGGG
 C  K  A  S  G  Y  I  F  T  E  Y  Y  M  Y  W 310        320        330        340
           *          *          *          *
ACGGTAGTATTGATTATGTTGAGAAGTTCAAAAAGAAGGCCACACT
 D  G  S  I  D  Y  V  E  K  F  K  K  K  A  T  L 410        420        430        440
           *          *          *          *
TGAGGACACAGCAACCTATTTTTGTGCTAGGGGAAAATTCAACTAT
 E  D  T  A  T  Y  F  C  A  R  G  K  F  N  Y
```

FIG. 30A

```
        50              60              70              80              90             100
         *               *               *               *               *               *
GTAAGGCACTCCCAAGTCCTAAACTTGAGAGATCATACACTTGGGAGACAGTGA
 G >
        150             160             170             180             190             200
         *               *               *               *               *               *
CTGCAGCAATCTGGGCCTGAGCTTCAGAGACCCGGGGCCTCAGTCAAGTTGTCG
 L   Q   Q   S   G   P   E   L   Q   R   P   G   A   S   V   K   L   S >
        250             260             270             280             290             300
         *               *               *               *               *               *
TGAAGCAGAGGCCTAAAACAGGGCCTGGAATTAGTAGGAAGGATCGATCCTGAAG
 V   K   Q   R   P   K   Q   G   L   E   L   V   G   R   I   D   P   E >
        350             360             370             380             390             400
         *               *               *               *               *               *
GACTGCAGATACATCGTCCAATACAGCCTACATGCAACTTAGCAGCCTGACATC
 T   A   D   T   S   S   N   T   A   Y   M   Q   L   S   S   L   T   S >
        450             460             470             480             490
         *               *               *               *               *
CGATTTGCTTACTGGGGCCAAGGCACCCTCGTCACAGTCTCCTCA
 R   F   A   Y   W   G   Q   G   T   L   V   T   V   S   S >

FIG. 30B
```

```
                    FR 1                 *            CDR 1                        FR 2
                *        *       20                 30            40 **            *
Rat Lo-CD2a Vk  DVVLTQTPPT LLATIGQSVS ISCRSSQSLL HSSGNTYLNW LLQRTGQSPQ
Humanized Vk    ---M---S--- ---V-L--PA- ---------- ---------- ----P-----
Human HUM5400 Vk ---M---S-LS -PV-L--PA-  -V Y-D---H--- FQ--P-----R CDR 2                                  FR 3
              *            60          70             80               *       90        CDR 3
                                                                                         100
Rat Lo-CD2a Vk  PLIYLVSKLE SGVPNRFSGS GSGTDFTLKI SGVEAEDLGV YYCMQFTHYP
Humanized Vk    ---------- -------D-- ---------- --V------- ----------
HumanHUM5400 Vk R---K--NRD ----D----- ---------- -R-V------ ----G--W-

FR 4
                110
Rat Lo-CD2a Vk  YTFGAGTKLE LK
Humanized Vk    ----Q----- I-
HumanHUM5400 Vk ----Q----- I-
```

FIG. 31

```
          10        20        30
    *      *    *    *    *    *    *
AAGCTTCATGATGAGTCCTGTCCAGTCCTTGTTTC
      M   M   S   P   V   Q   S   L   F 110       120       130
    *      *    *    *    *    *    *
GAGTTCTGACTGCCCATGTTGGCTGTCCATGTGTG 210       220       230
    *      *    *    *    *    *    *
AGATGAGATAGGATTTGTGCTAAGAGGATTCTAAT 310       320       330
    *      *    *    *    *    *    *
ATATTTTTAAAAATCACAAAACACACCGGGATCT 410       420       430
    *      *    *    *    *    *    *
TCTGATCTATTATAATTTCAGGAACCAATGGTGAT
                              T   N   G   D 510       520       530
    *      *    *    *    *    *    *
CAGGTCAAGTCAGAGTCTCTTACATAGTAGTGGAA
  R   S   S   Q   S   L   L   H   S   S   G 610       620       630
    *      *    *    *    *    *    *
TCCAAACTGGAATCTGGGGTCCCCGACAGGTTCAG
  S   K   L   E   S   G   V   P   D   R   F   S 710       720       730
    *      *    *    *    *    *    *
TTTATTACTGCATGCAATTTACCCATTATCCGTAC
  V   Y   Y   C   M   Q   F   T   H   Y   P   Y
    *
TGGATCC
```

FIG. 32A

```
         40             50             60             70
   *      *      *      *      *      *      *
TGTTATTGCTTTGGATTCTGGGTAAGTAGAGAATG
 L   L   L   L   W   I   L   G>

140            150            160            170
   *      *      *      *      *      *      *
GTAAGGCAGGTCCTATTTTCTAAGATGGACACTTG 240            250            260            270
   *      *      *      *      *      *      *
GTAGATGAGAAGGTGTATGCCATTTAGGATTTGCA 340            350            360            370
   *      *      *      *      *      *      *
CACAGGAAATGAGTAACAAAAAGTAATTCACAAAG 440            450            460            470
   *      *      *      *      *      *      *
GTTGTGATGACCCAGAGTCCACCTTCATTATTGGT
 V   V   M   T   Q   S   P   P   S   L   L   V 540            550            560            570
   *      *      *      *      *      *      *
ACACCTATTTAAATTGGTTGCTACAGAGGCCAGGC
 N   T   Y   L   N   W   L   L   Q   R   P   G 640            650            660            670
   *      *      *      *      *      *      *
TGGCTCAGGGAGTGGAACAGATTTCACACTCAAAA
 G   S   G   S   G   T   D   F   T   L   K 740            750            760            770
   *      *      *      *      *      *      *
ACGTTTGGACAAGGAACCAAGCTGGAAATCAAACG
 T   F   G   Q   G   T   K   L   E   I   K>
```

FIG. 32B

```
              80         90        100
         *    *    *    *    *    *
    AGTTACAGGACAAGAATGGGGATGGAGGAT 180        190       200
         *    *    *    *    *    *
    AGATTCCATTACTTGATAATGAGAAATTAC 280        290       300
         *    *    *    *    *    *
    ACCAATTGTTTGTTGAAAAAGCATTTGGT 380        390       400
         *    *    *    *    *    *
    ATTGGTTGCAAATTTTGCACATAACTTTGT 480        490       500
         *    *    *    *    *    *
    AACCTTGGGACAACCAGCTTCCATCTCTTG
      T  L  G  Q  P  A  S  I  S  C>

580        590       600
         *    *    *    *    *    *
    CAATCTCCACAGCCGCTAATTTATTTGGTA
      Q  S  P  Q  P  L  I  Y  L  V>

680        690       700
         *    *    *    *    *    *
    TCAGTGGAGTGGAAGCTGAGGATGTGGGGG
      I  S  G  V  E  A  E  D  V  G>

780        790       800
         *    *    *    *    *    *
    TGAGTAGAATTTAAACTTTGCTTCCTCAGT
```

FIG. 32C

```
                       FR 1                                            CDR 1                       FR 2
                         10         20           30             40                   *  50
Rat Lo-CD2a Vh  EVQLQQSGPE LQRPGASVKL SCKASGYIFT EYYMYWVYQR PKQGLELVGR
Humanized Vh    Q---V-----  ---A----V  -----T---  -----R-A-  -G------M--
Human Amu 5-3 Vh Q---V-----  ---A----V  G----T---  G---H--R-A  -G------WM--

60          *   *    *   80       *  *  90                 100
Rat Lo-CD2a Vh  IDPEDGSIDY VEKFKKKATL TADTSSNTAY MQLSSLTSED TATYFCARGK
Humanized Vh    ----------  ------V--  -----S---  -E-----D-   --V--Y----
Human Amu 5-3 Vh -N-NS-GTN-  AQ--QGRV-M -R---IS---  -E--R-R-D-  --V--Y----R CDR 3            FR 4
                           110
Rat Lo-CD2a Vh  FNYR/////FAYWGQ GTLVTVSS
Humanized Vh    ----//////------  --------
Human Amu 5-3 Vh TE-IVVAEG-D----  --------
```

FIG. 33

```
           10        20        30
    *      *     *      *      *     *     *
AAGCTTCATGAAATGCAGGTGGATCATCCTCTTCT
         M  K  C  R  W  I  I  L  F 110       120       130
    *      *     *      *      *     *     *
ACAGTGACACTATCTTTGGATTTCTTTCAACAGGG 210       220       230
    *      *     *      *      *     *     *
GGTCTCCTGCAAGGCTTCTGGATACACCTTCACCG
     V  S  C  K  A  S  G  Y  T  F  T 310       320       330
    *      *     *      *      *     *     *
CCTGAAGACGGTAGTATTGATTATGTTGAGAAGTT
  P  E  D  G  S  I  D  Y  V  E  K  F 410       420       430
    *      *     *      *      *     *     *
TGACCTCTGACGACACGGCCGTGTATTACTGTGCG
 L  T  S  D  D  T  A  V  Y  Y  C  A 510       520       530
    *      *     *      *      *     *     *
TGAGTCTTTACAACCTCTCTCTTCTATTCAGCTTA 610       620       630
    *      *     *      *      *     *     *
AGGGACACCTTGGGAGTCAGAAAGGGTCATTGGGA
```

FIG. 34A

```
       40         50         60         70
        *          *          *          *
TGATGGCAGTAGCTACAGGTAAGGCACTCCCAAGTC
 L  M  A  V  A  T  G>

140        150        160        170
        *          *          *          *
GTCAACTCACAGGTGCAGCTGGTGCAGTCTGGGGCT
 V  N  S  Q  V  Q  L  V  Q  S  G  A 240        250        260        270
        *          *          *          *
AGTACTATATGTACTGGGTGCGACAGGCCCCTGGAC
 E  Y  Y  M  Y  W  V  R  Q  A  P  G 340        350        360        370
        *          *          *          *
TAAGAAAAAGGTCACCCTGACCGCTGACACGTCCTC
 K  K  K  V  T  L  T  A  D  T  S  S 440        450        460        470
        *          *          *          *
AGAGGAAAGTTTAATTATAGTTTTGCTTACTGGGGC
 R  G  K  F  N  Y  R  F  A  Y  W  G 540        550        560        570
        *          *          *          *
AATAGATTTTACTGCATTTGTTGGGGGGGAAATGTG 640        650        660        670
        *          *          *          *
GCCCGGGCTGATGCAGACAGACATCCTCAGCTCCCG
```

FIG. 34B

```
            80         90        100
             *          *          *
      CTAAACTTGAGAGATCATACACTTGGGAG 180        190        200
             *          *          *
      GAGGTGAAGAAGCCTGGGGCCTCAGTGAA
       E  V  K  K  P  G  A  S  V  K>

280        290        300
             *          *          *
      AAGGGCTTGAGCTGATGGGAAGGATCGAT
       Q  G  L  E  L  M  G  R  I  D>

380        390        400
             *          *          *
      TAGCACAGCCTACATGGAGCTGAGCAGCC
          S  T  A  Y  M  E  L  S  S>

480        490        500
             *          *          *
      CAAGGAACCCTGGTCACCGTCTCCTCAGG
       Q  G  T  L  V  T  V  S  S>

580        590        600
             *          *          *
      TGTATCTGAATTTCAGGTCATGAAGGACT 680        690        700
             *          *          *
      GACTTCATGGCCAGAGATTTATAGGGATC
```

FIG. 34C

SEQUENCE LISTING

```
(1) GENERAL INFORMATION:

(iii) NUMBER OF SEQUENCES:   96

(2) INFORMATION FOR SEQ ID NO: 1:

(i) SEQUENCE CHARACTERISTICS:
        (A) LENGTH: 32 bases
        (B) TYPE:   nucleic acid
        (C) STRANDEDNESS:  single
        (D) TOPOLOGY:  linear (ii) MOLECULE TYPE:   oligonucleotide (ix) FEATURE:
        (A) NAME/KEY:  PCR primer (xi) SEQUENCE DESCRIPTION:   SEQ ID NO: 1:

AACCCGGGGA CATTCAGCTG ACCCAGTCTC AA                                    32

(2) INFORMATION FOR SEQ ID NO: 2:

(i) SEQUENCE CHARACTERISTICS:
        (A) LENGTH: 29 bases
        (B) TYPE:   nucleic acid
        (C) STRANDEDNESS:  single
        (D) TOPOLOGY:  linear (ii) MOLECULE TYPE:   oligonucleotide (ix) FEATURE:
        (A) NAME/KEY:  PCR primer
```

(xi) SEQUENCE DESCRIPTION: SEQ ID NO: 2:

CAGTCGACTA CAGTTGGTGC AGCATCAGC                              29

(2) INFORMATION FOR SEQ ID NO: 3:

(i) SEQUENCE CHARACTERISTICS:
        (A) LENGTH: 31 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 3:

AACCCGGGGA GGTCCAGCTG CAGCAGTCTG G                            31

(2) INFORMATION FOR SEQ ID NO: 4:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 4:

AAGTCGACCC AGTGGATAGA CCGATGG                                 27

(2) INFORMATION FOR SEQ ID NO: 5:

(i) SEQUENCE CHARACTERISTICS:
        (A) LENGTH: 22 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 5:

CCGCAAGCTT CATGGGATGG AG                                      22

(2) INFORMATION FOR SEQ ID NO: 6:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 6:

GCTGCTTGGG GACTGGGTCA GCTGGAT                                 27

(2) INFORMATION FOR SEQ ID NO: 7:

```
    (i) SEQUENCE CHARACTERISTICS:
        (A) LENGTH: 21 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 7:

ATTCAGCTGA CCCAGTCTCC A                                            21

(2) INFORMATION FOR SEQ ID NO: 8:

(i) SEQUENCE CHARACTERISTICS:
        (A) LENGTH: 58 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 8:

GATCGGATCC ACCTGAGGAA GCAAAGTTTA AATTCTACTC ACGTTTCAGT TCCAGCTT    58

(2) INFORMATION FOR SEQ ID NO: 9:

(i) SEQUENCE CHARACTERISTICS:
        (A) LENGTH: 31 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 9:

TCTCCTGCAG TGGGACCTCG GAGTGGACAC C                                 31

(2) INFORMATION FOR SEQ ID NO: 10:

(i) SEQUENCE CHARACTERISTICS:
        (A) LENGTH: 21 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 10:

GAGGTCCAGC TGCAGCAGTC T                                            21

(2) INFORMATION FOR SEQ ID NO: 11:

(i) SEQUENCE CHARACTERISTICS:
        (A) LENGTH: 24 bases
        (B) TYPE: nucleic acid
        (C) STRANDEDNESS: single
        (D) TOPOLOGY: linear
```

(ii) MOLECULE TYPE: oligonucleotide (ix) FEATURE:
             (A) NAME/KEY: PCR primer (xi) SEQUENCE DESCRIPTION: SEQ ID NO: 11:

CGATGTATCA GCTGTCAGTG TGGC                                              24

(2) INFORMATION FOR SEQ ID NO: 12:

(i) SEQUENCE CHARACTERISTICS:
             (A) LENGTH: 24 bases
             (B) TYPE: nucleic acid
             (C) STRANDEDNESS: single
             (D) TOPOLOGY: linear (ii) MOLECULE TYPE: oligonucleotide (ix) FEATURE:
             (A) NAME/KEY: PCR primer (xi) SEQUENCE DESCRIPTION: SEQ ID NO: 12:

GCCACACTGA CAGCTGATAC ATCG                                              24

(2) INFORMATION FOR SEQ ID NO: 13:

(i) SEQUENCE CHARACTERISTICS:
             (A) LENGTH: 21 bases
             (B) TYPE: nucleic acid
             (C) STRANDEDNESS: single
             (D) TOPOLOGY: linear (ii) MOLECULE TYPE: oligonucleotide (ix) FEATURE:
             (A) NAME/KEY: PCR primer (xi) SEQUENCE DESCRIPTION: SEQ ID NO: 13:

CAGAGTGCCT TGGCCCCAGT A                                                 21

(2) INFORMATION FOR SEQ ID NO: 14:

(i) SEQUENCE CHARACTERISTICS:
             (A) LENGTH: 27 bases
             (B) TYPE: nucleic acid
             (C) STRANDEDNESS: single
             (D) TOPOLOGY: linear (ii) MOLECULE TYPE: oligonucleotide (ix) FEATURE:
             (A) NAME/KEY: PCR primer (xi) SEQUENCE DESCRIPTION: SEQ ID NO: 14:

TACTGGGGCC AAGGCACCCT CGTCACA                                           27

(2) INFORMATION FOR SEQ ID NO: 15:

(i) SEQUENCE CHARACTERISTICS:
             (A) LENGTH: 25 bases
             (B) TYPE: nucleic acid
             (C) STRANDEDNESS: single
             (D) TOPOLOGY: linear (ii) MOLECULE TYPE: oligonucleotide (ix) FEATURE:
             (A) NAME/KEY: PCR primer (xi) SEQUENCE DESCRIPTION: SEQ ID NO: 15:

```
GATCGGATCC CTATAAATCT CTGGC                                          25

(2) INFORMATION FOR SEQ ID NO: 16:

(i) SEQUENCE CHARACTERISTICS:
        (A) LENGTH: 43 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 16:

TTGGATCCGC GGCCGCGTCG ACTACAGTTG GTGCAGCATC AGC                      43

(2) INFORMATION FOR SEQ ID NO: 17:

(i) SEQUENCE CHARACTERISTICS:
        (A) LENGTH: 41 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 17:

ATGGATCCGC GGCCGCGTCG ACCCAGTGGA TAGACCGATG G                        41

(2) INFORMATION FOR SEQ ID NO: 18:

(i) SEQUENCE CHARACTERISTICS:
        (A) LENGTH: 31 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 18:

CCATGGCCTC GAGGGCCCCC CCCCCCCCCC C                                   31

(2) INFORMATION FOR SEQ ID NO: 19:

(i) SEQUENCE CHARACTERISTICS:
        (A) LENGTH: 29 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 19:

CCTGTTTAGG CCTCTGCTTC ACCCAGTAC                                      29

(2) INFORMATION FOR SEQ ID NO: 20:

(i) SEQUENCE CHARACTERISTICS:
        (A) LENGTH: 29 bases
```

(B) TYPE: nucleic acid
          (C) STRANDEDNESS: single
          (D) TOPOLOGY: linear (ii) MOLECULE TYPE: oligonucleotide (ix) FEATURE:
          (A) NAME/KEY: PCR primer (xi) SEQUENCE DESCRIPTION: SEQ ID NO: 20:

GGATAATGGG TAAATTGCAT GCAGTAATA                                              29

(2) INFORMATION FOR SEQ ID NO: 21:

(i) SEQUENCE CHARACTERISTICS:
          (A) LENGTH: 30 bases
          (B) TYPE: nucleic acid
          (C) STRANDEDNESS: single
          (D) TOPOLOGY: linear (ii) MOLECULE TYPE: oligonucleotide (ix) FEATURE:
          (A) NAME/KEY: PCR primer (xi) SEQUENCE DESCRIPTION: SEQ ID NO: 21:

TGCAAGCTTC ATGATGAGTC CTGTCCAGTC                                             30

(2) INFORMATION FOR SEQ ID NO: 22:

(i) SEQUENCE CHARACTERISTICS:
          (A) LENGTH: 28 bases
          (B) TYPE: nucleic acid
          (C) STRANDEDNESS: single
          (D) TOPOLOGY: linear (ii) MOLECULE TYPE: oligonucleotide (ix) FEATURE:
          (A) NAME/KEY: PCR primer (xi) SEQUENCE DESCRIPTION: SEQ ID NO: 22:

AGTAAGCTTC ATGAAATGCA GGTGGATC                                               28

(2) INFORMATION FOR SEQ ID NO: 23:

(i) SEQUENCE CHARACTERISTICS:
          (A) LENGTH: 24 bases
          (B) TYPE: nucleic acid
          (C) STRANDEDNESS: single
          (D) TOPOLOGY: linear (ii) MOLECULE TYPE: oligonucleotide (ix) FEATURE:
          (A) NAME/KEY: PCR primer (xi) SEQUENCE DESCRIPTION: SEQ ID NO: 23:

GGGAGATTGC TGCAGCTGGA CTTC                                                   24

(2) INFORMATION FOR SEQ ID NO: 24:

(i) SEQUENCE CHARACTERISTICS:
          (A) LENGTH: 33 bases
          (B) TYPE: nucleic acid
          (C) STRANDEDNESS: single
          (D) TOPOLOGY: linear (ii) MOLECULE TYPE: oligonucleotide (ix) FEATURE:

-continued (A) NAME/KEY: PCR primer (xi) SEQUENCE DESCRIPTION: SEQ ID NO: 24:

GATCCCCGGG CCACCATGAT GAGTCCTGTC CAG                    33

(2) INFORMATION FOR SEQ ID NO: 25:

(i) SEQUENCE CHARACTERISTICS:
        (A) LENGTH: 61 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 25:

AGAATGGCCA CGTCATCCGA CCCCCTCAGA GTTTACTATT CTACTATCCA ACTGAGGAAG    60
C                                                                    61

(2) INFORMATION FOR SEQ ID NO: 26:

(i) SEQUENCE CHARACTERISTICS:
        (A) LENGTH: 34 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 26:

GATCGAATTC GCCACCATGA AATGCAGGTG GATC                   34

(2) INFORMATION FOR SEQ ID NO: 27:

(i) SEQUENCE CHARACTERISTICS:
        (A) LENGTH: 37 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 27:

CCAGAAAGCT AGCTTGCCAT CCCTATAAAT CTCTGGC                37

(2) INFORMATION FOR SEQ ID NO: 28:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: polypeptide (xi) SEQUENCE DESCRIPTION: SEQ ID NO: 28:

Asp Val Val Leu Thr Gln Thr Pro Pro Thr
              5                  10

Leu Leu Ala Thr Ile Gly Gln Ser Val Ser

```
            15                  20
Ile Ser Cys (2) INFORMATION FOR SEQ ID NO: 29:

(i) SEQUENCE CHARACTERISTICS:
        (A) LENGTH: 23 amino acids
        (B) TYPE:   amino acid
        (C) STRANDEDNESS:
        (D) TOPOLOGY: linear (ii) MOLECULE TYPE:  polypeptide (xi) SEQUENCE DESCRIPTION:  SEQ ID NO: 29:

Asp Val Val Met Thr Gln Ser Pro Leu Ser
                 5                  10

Leu Pro Val Thr Leu Gly Gln Pro Ala Ser
            15                  20

Ile Ser Cys (2) INFORMATION FOR SEQ ID NO: 30:

(i) SEQUENCE CHARACTERISTICS:
        (A) LENGTH: 15 amino acids
        (B) TYPE:   amino acid
        (C) STRANDEDNESS:
        (D) TOPOLOGY: linear (ii) MOLECULE TYPE:  polypeptide (xi) SEQUENCE DESCRIPTION:  SEQ ID NO: 30:

Trp Leu Leu Gln Arg Thr Gly Gln Ser Pro
                 5                  10

Gln Pro Leu Ile Tyr
            15

(2) INFORMATION FOR SEQ ID NO: 31:

(i) SEQUENCE CHARACTERISTICS:
        (A) LENGTH: 15 amino acids
        (B) TYPE:   amino acid
        (C) STRANDEDNESS:
        (D) TOPOLOGY: linear (ii) MOLECULE TYPE:  polypeptide (xi) SEQUENCE DESCRIPTION:  SEQ ID NO: 31:

Trp Phe Gln Gln Arg Pro Gly Gln Ser Pro
                 5                  10

Arg Arg Leu Ile Tyr
            15

(2) INFORMATION FOR SEQ ID NO: 32:

(i) SEQUENCE CHARACTERISTICS:
        (A) LENGTH: 32 amino acids
        (B) TYPE:   amino acid
        (C) STRANDEDNESS:
        (D) TOPOLOGY: linear (ii) MOLECULE TYPE:  polypeptide (xi) SEQUENCE DESCRIPTION:  SEQ ID NO: 32:

Gly Val Pro Asn Arg Phe Ser Gly Ser Gly
                 5                  10
```

```
Ser Gly Thr Asp Phe Thr Leu Lys Ile Ser
                15                  20

Gly Val Glu Ala Glu Asp Leu Gly Val Tyr
                25                  30

Tyr Cys (2) INFORMATION FOR SEQ ID NO: 33:

(i) SEQUENCE CHARACTERISTICS:
        (A) LENGTH: 32 amino acids
        (B) TYPE:   amino acid
        (C) STRANDEDNESS:
        (D) TOPOLOGY:  linear (ii) MOLECULE TYPE:  polypeptide (xi) SEQUENCE DESCRIPTION:  SEQ ID NO: 33:

Gly Val Pro Asp Arg Phe Ser Gly Ser Gly
                5                   10

Ser Gly Thr Asp Phe Thr Leu Lys Ile Ser
                15                  20

Arg Val Glu Ala Glu Asp Val Gly Val Tyr
                25                  30

Tyr Cys (2) INFORMATION FOR SEQ ID NO: 34:

(i) SEQUENCE CHARACTERISTICS:
        (A) LENGTH: 10 amino acids
        (B) TYPE:   amino acid
        (C) STRANDEDNESS:
        (D) TOPOLOGY:  linear (ii) MOLECULE TYPE:  polypeptide (xi) SEQUENCE DESCRIPTION:  SEQ ID NO: 34:

Phe Gly Ala Gly Thr Lys Leu Glu Leu Lys
                5                   10

(2) INFORMATION FOR SEQ ID NO: 35:

(i) SEQUENCE CHARACTERISTICS:
        (A) LENGTH: 10 amino acids
        (B) TYPE:   amino acid
        (C) STRANDEDNESS:
        (D) TOPOLOGY:  linear (ii) MOLECULE TYPE:  polypeptide (xi) SEQUENCE DESCRIPTION:  SEQ ID NO: 35:

Phe Gly Gln Gly Thr Lys Leu Glu Ile Lys
                5                   10

(2) INFORMATION FOR SEQ ID NO: 36:

(i) SEQUENCE CHARACTERISTICS:
        (A) LENGTH: 81 bases
        (B) TYPE:   nucleic acid
        (C) STRANDEDNESS:  single
        (D) TOPOLOGY:  linear (ii) MOLECULE TYPE:  oligonucleotide (ix) FEATURE:
        (A) NAME/KEY:  PCR primer (xi) SEQUENCE DESCRIPTION:  SEQ ID NO: 36:
```

GCAAGAGATG GAAGCTGGTT GTCCCAAGGT TACCAATAAT GAAGGTGGAC TCTGGGTCAT    60

CACAACATCA CCATTGGTTC C    81

(2) INFORMATION FOR SEQ ID NO: 37:

(i) SEQUENCE CHARACTERISTICS:
        (A) LENGTH: 72 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 37:

CAACCAGCTT CCATCTCTTG CAGGTCAAGT CAGAGTCTCT TACATAGTAG TGGAAACACC    60

TATTTAAATT GG    72

(2) INFORMATION FOR SEQ ID NO: 38:

(i) SEQUENCE CHARACTERISTICS:
        (A) LENGTH: 81 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 38:

AGATTCCAGT TTGGATACCA AATAAATTAG CGGCTGTGGA GATTGGCCTG GCCTTAGCAA    60

CCAATTTAAA TAGGTGTTTC C    81

(2) INFORMATION FOR SEQ ID NO: 39:

(i) SEQUENCE CHARACTERISTICS:
        (A) LENGTH: 81 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 39:

TTGGTATCCA AACTGGAATC TGGGGTCCCC GACAGGTTCA GTGGCTCAGG GAGTGGAACA    60

GATTTCACAC TCAAAATCAG T    81

(2) INFORMATION FOR SEQ ID NO: 40:

(i) SEQUENCE CHARACTERISTICS:
        (A) LENGTH: 72 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 40:

ATGGGTAAAT TGCATGCAGT AATAAACCCC CACATCCTCA GCTTCCACTC CACTGATTTT    60

GAGTGTGAAA TC    72

(2) INFORMATION FOR SEQ ID NO: 41:

(i) SEQUENCE CHARACTERISTICS:
        (A) LENGTH: 63 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 41:

TACTGCATGC AATTTACCCA TTATCCGTAC ACGTTTGGAC AAGGGACCAA GCTGGAAATC    60

AAA    63

(2) INFORMATION FOR SEQ ID NO: 42:

(i) SEQUENCE CHARACTERISTICS:
        (A) LENGTH: 67 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 42:

GATCGGATCC AACTGAGGAA GCAAAGTTTA AATTCTACTC ACGTTTGATT TCCAGCTTGG    60

TCCCTTG    67

(2) INFORMATION FOR SEQ ID NO: 43:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 43:

GATCAAGCTT CATGATGAGT CCT    23

(2) INFORMATION FOR SEQ ID NO: 44:

(i) SEQUENCE CHARACTERISTICS:
        (A) LENGTH: 21 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 44:

```
GCAAGAGATG GAAGCTGGTT G                                              21

(2) INFORMATION FOR SEQ ID NO: 45:

(i) SEQUENCE CHARACTERISTICS:
         (A) LENGTH: 21 bases
         (B) TYPE:  nucleic acid
         (C) STRANDEDNESS: single
         (D) TOPOLOGY:  linear (ii) MOLECULE TYPE:  oligonucleotide (ix) FEATURE:
         (A) NAME/KEY:  PCR primer (xi) SEQUENCE DESCRIPTION: SEQ ID NO: 45:

CAACCAGCTT CCATCTCTTG C                                              21

(2) INFORMATION FOR SEQ ID NO: 46:

(i) SEQUENCE CHARACTERISTICS:
         (A) LENGTH: 21 bases
         (B) TYPE:  nucleic acid
         (C) STRANDEDNESS: single
         (D) TOPOLOGY:  linear (ii) MOLECULE TYPE:  oligonucleotide (ix) FEATURE:
         (A) NAME/KEY:  PCR primer (xi) SEQUENCE DESCRIPTION: SEQ ID NO: 46:

AGATTCCAGT TTGGATACCA A                                              21

(2) INFORMATION FOR SEQ ID NO: 47:

(i) SEQUENCE CHARACTERISTICS:
         (A) LENGTH: 24 bases
         (B) TYPE:  nucleic acid
         (C) STRANDEDNESS: single
         (D) TOPOLOGY:  linear (ii) MOLECULE TYPE:  oligonucleotide (ix) FEATURE:
         (A) NAME/KEY:  PCR primer (xi) SEQUENCE DESCRIPTION: SEQ ID NO: 47:

TTGGTATCCA AACTGGAATC TGGG                                           24

(2) INFORMATION FOR SEQ ID NO: 48:

(i) SEQUENCE CHARACTERISTICS:
         (A) LENGTH: 24 bases
         (B) TYPE:  nucleic acid
         (C) STRANDEDNESS: single
         (D) TOPOLOGY:  linear (ii) MOLECULE TYPE:  oligonucleotide (ix) FEATURE:
         (A) NAME/KEY:  PCR primer (xi) SEQUENCE DESCRIPTION: SEQ ID NO: 48:

ATGGGTAAAT TGCATGCAGT AATA                                           24

(2) INFORMATION FOR SEQ ID NO: 49:

(i) SEQUENCE CHARACTERISTICS:
```

(A) LENGTH: 24 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 49:

TACTGCATGC AATTTACCCA TTAT                                                24

(2) INFORMATION FOR SEQ ID NO: 50:

(i) SEQUENCE CHARACTERISTICS:
        (A) LENGTH: 26 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 50:

GATCGGATCC AACTGAGGAA GCAAAG                                              26

(2) INFORMATION FOR SEQ ID NO: 51:

(i) SEQUENCE CHARACTERISTICS:
        (A) LENGTH: 30 amino acids
        (B) TYPE: amino acid
        (C) STRANDEDNESS:
        (D) TOPOLOGY: linear (ii) MOLECULE TYPE: polypeptide (xi) SEQUENCE DESCRIPTION: SEQ ID NO: 51:

Glu Val Gln Leu Gln Gln Ser Gly Pro Glu
                5                   10

Leu Gln Arg Pro Gly Ala Ser Val Lys Leu
                15                  20

Ser Cys Lys Ala Ser Gly Tyr Ile Phe Thr
                25                  30

(2) INFORMATION FOR SEQ ID NO: 52:

(i) SEQUENCE CHARACTERISTICS:
        (A) LENGTH: 30 amino acids
        (B) TYPE: amino acid
        (C) STRANDEDNESS:
        (D) TOPOLOGY: linear (ii) MOLECULE TYPE: polypeptide (xi) SEQUENCE DESCRIPTION: SEQ ID NO: 52:

Gln Val Gln Leu Val Gln Ser Gly Ala Glu
                5                   10

Val Lys Lys Pro Gly Ala Ser Val Lys Val
                15                  20

Ser Cys Lys Ala Ser Gly Tyr Thr Phe Thr
                25                  30

(2) INFORMATION FOR SEQ ID NO: 53:

(i) SEQUENCE CHARACTERISTICS:
            (A) LENGTH: 14 amino acids
            (B) TYPE: amino acid
            (C) STRANDEDNESS:
            (D) TOPOLOGY: linear (ii) MOLECULE TYPE: polypeptide (xi) SEQUENCE DESCRIPTION: SEQ ID NO: 53:

Trp Val Lys Gln Arg Pro Lys Gln Gly Leu
                 5                  10

Glu Leu Val Gly (2) INFORMATION FOR SEQ ID NO: 54:

(i) SEQUENCE CHARACTERISTICS:
            (A) LENGTH: 14 amino acids
            (B) TYPE: amino acid
            (C) STRANDEDNESS:
            (D) TOPOLOGY: linear (ii) MOLECULE TYPE: polypeptide (xi) SEQUENCE DESCRIPTION: SEQ ID NO: 54:

Trp Val Arg Gln Ala Pro Gly Gln Gly Leu
                 5                  10

Glu Trp Met Gly (2) INFORMATION FOR SEQ ID NO: 55:

(i) SEQUENCE CHARACTERISTICS:
            (A) LENGTH: 32 amino acids
            (B) TYPE: amino acid
            (C) STRANDEDNESS:
            (D) TOPOLOGY: linear (ii) MOLECULE TYPE: polypeptide (xi) SEQUENCE DESCRIPTION: SEQ ID NO: 55:

Lys Ala Thr Leu Thr Ala Asp Thr Ser Ser
                 5                  10

Asn Thr Ala Tyr Met Gln Leu Ser Ser Leu
                15                  20

Thr Ser Glu Asp Thr Ala Thr Tyr Phe Cys
                25                  30

Ala Arg (2) INFORMATION FOR SEQ ID NO: 56:

(i) SEQUENCE CHARACTERISTICS:
            (A) LENGTH: 32 amino acids
            (B) TYPE: amino acid
            (C) STRANDEDNESS:
            (D) TOPOLOGY: linear (ii) MOLECULE TYPE: polypeptide (xi) SEQUENCE DESCRIPTION: SEQ ID NO: 56:

Arg Val Thr Met Thr Arg Asp Thr Ser Ile
                 5                  10

Ser Thr Ala Tyr Met Glu Leu Ser Arg Leu
                15                  20

Arg Ser Asp Asp Thr Ala Val Tyr Tyr Cys
                25                  30

Ala Arg (2) INFORMATION FOR SEQ ID NO: 57:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: polypeptide (xi) SEQUENCE DESCRIPTION: SEQ ID NO: 57:

Trp Gly Gln Gly Thr Leu Val Thr Val Ser
               5                    10
Ser (2) INFORMATION FOR SEQ ID NO: 58:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: polypeptide (xi) SEQUENCE DESCRIPTION: SEQ ID NO: 58:

Trp Gly Gln Gly Thr Leu Val Thr Val Ser
               5                    10
Ser (2) INFORMATION FOR SEQ ID NO: 59:

(i) SEQUENCE CHARACTERISTICS:
        (A) LENGTH: 88 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 59:

```
GATCAAGCTT CATGAAATGC AGGTGGATCA TCCTCTTCTT GATGGCAGTA GCTACAGGTA      60

AGGCACTCCC AAGTCGTAAA CTTGAGAG                                        88
```

(2) INFORMATION FOR SEQ ID NO: 60:

(i) SEQUENCE CHARACTERISTICS:
        (A) LENGTH: 87 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 60:

```
CACCTGTGAG TTGACCCCTG TTGAAAGAAA TCCAAAGATA GTGTCACTGT CTCCCAAGTG      60

TATGATCTCT CAAGTTTAGG ACTTGGG                                         87
```

(2) INFORMATION FOR SEQ ID NO: 61:

(i) SEQUENCE CHARACTERISTICS:
        (A) LENGTH: 78 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 61:

```
ACAGGGGTCA ACTCACAGGT GCAGCTGGTG CAGTCTGGGG CTGAGGTGAA GAAGCCTGGG      60

GCCTCAGTGA AGGTCTCC                                                    78
```

(2) INFORMATION FOR SEQ ID NO: 62:

(i) SEQUENCE CHARACTERISTICS:
        (A) LENGTH: 78 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 62:

```
GGCCTGTCGC ACCCAGTACA TATAGTACTC GGTGAAGGTG TATCCAGAAG CCTTGCAGGA      60

GACCTTCACT GAGGCCCC                                                    78
```

(2) INFORMATION FOR SEQ ID NO: 63:

(i) SEQUENCE CHARACTERISTICS:
        (A) LENGTH: 78 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 63:

```
ATGTACTGGG TGCGACAGGC CCCTGGACAA GGGCTTGAGC TGATGGGAAG GATCGATCCT      60

GAAGACGGTA GTATTGAT                                                    78
```

(2) INFORMATION FOR SEQ ID NO: 64:

(i) SEQUENCE CHARACTERISTICS:
        (A) LENGTH: 78 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 64:

```
TGTGCTAGAG GACGTGTCAG CGGTCAGGGT GACCTTTTTC TTAAACTTCT CAACATAATC      60

AATACTACCG TCTTCAGG                                                    78
```

(2) INFORMATION FOR SEQ ID NO: 65:

(i) SEQUENCE CHARACTERISTICS:
        (A) LENGTH: 84 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 65:

```
GCTGACACGT CCTCTAGCAC AGCCTACATG GAGCTGAGCA GCCTGACCTC TGACGACACG    60

GCCGTGTATT ACTGTGCGAG AGGA                                          84
```

(2) INFORMATION FOR SEQ ID NO: 66:

(i) SEQUENCE CHARACTERISTICS:
        (A) LENGTH: 87 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 66:

```
GGACTCACCT GAGGAGACGG TGACCAGGGT TCCTTGGCCC CAGTAAGCAA ACCTATAGTT    60

AAACTTTCCT CTCGCACAGT AATACAC                                       87
```

(2) INFORMATION FOR SEQ ID NO: 67:

(i) SEQUENCE CHARACTERISTICS:
        (A) LENGTH: 69 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 67:

```
ACCGTCTCCT CAGGTGAGTC CTTACAACCT CTCTCTTCTA TTCAGCTTAA ATAGATTTTA    60

CTGCATTTG                                                           69
```

(2) INFORMATION FOR SEQ ID NO: 68:

(i) SEQUENCE CHARACTERISTICS:
        (A) LENGTH: 69 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 68:

```
CCTAGTCCTT CATGACCTGA AATTCAGATA CACACATTTC CCCCCCAACA AATGCAGTAA    60

AATCTATTT                                                           69
```

(2) INFORMATION FOR SEQ ID NO: 69:

(i) SEQUENCE CHARACTERISTICS:
        (A) LENGTH: 72 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 69:

```
TTCAGGTCAT GAAGGACTAG GGACACCTTG GGAGTCAGAA AGGGTCATTG GGAGCCCGGG     60

CTGATGCAGA CA                                                        72
```

(2) INFORMATION FOR SEQ ID NO: 70:

(i) SEQUENCE CHARACTERISTICS:
        (A) LENGTH: 72 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 70:

```
GATCGGATCC CTATAAATCT CTGGCCATGA AGTCTGGGAG CTGAGGATGT CTGTCTGCAT     60

CAGCCCGGGC TC                                                        72
```

(2) INFORMATION FOR SEQ ID NO: 71:

(i) SEQUENCE CHARACTERISTICS:
        (A) LENGTH: 25 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 71:

```
GATCAAGCTT CATGAAATGC AGGTG                                          25
```

(2) INFORMATION FOR SEQ ID NO: 72:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 72:

```
CACCTGTGAG TTGACCCCTG TTG                                            23
```

(2) INFORMATION FOR SEQ ID NO: 73:

```
    (i) SEQUENCE CHARACTERISTICS:
        (A) LENGTH: 21 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 73:

ACAGGGGTCA ACTCACAGGT G                                              21

(2) INFORMATION FOR SEQ ID NO: 74:

(i) SEQUENCE CHARACTERISTICS:
        (A) LENGTH: 21 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 74:

GGCCTGTCGC ACCCAGTACA T                                              21

(2) INFORMATION FOR SEQ ID NO: 75:

(i) SEQUENCE CHARACTERISTICS:
        (A) LENGTH: 21 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 75:

ATGTACTGGG TGCGACAGGC C                                              21

(2) INFORMATION FOR SEQ ID NO: 76:

(i) SEQUENCE CHARACTERISTICS:
        (A) LENGTH: 21 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 76:

TGTGCTAGAG GACGTGTCAG C                                              21

(2) INFORMATION FOR SEQ ID NO: 77:

(i) SEQUENCE CHARACTERISTICS:
        (A) LENGTH: 21 bases
        (B) TYPE: nucleic acid
        (C) STRANDEDNESS: single
        (D) TOPOLOGY: linear
```

-continued

```
        (ii) MOLECULE TYPE:  oligonucleotide (ix) FEATURE:
             (A) NAME/KEY:  PCR primer (xi) SEQUENCE DESCRIPTION:  SEQ ID NO: 77:
```

GCTGACACGT CCTCTAGCAC A                                              21

(2) INFORMATION FOR SEQ ID NO: 78:

```
        (i) SEQUENCE CHARACTERISTICS:
             (A) LENGTH:  21 bases
             (B) TYPE:  nucleic acid
             (C) STRANDEDNESS:  single
             (D) TOPOLOGY:  linear (ii) MOLECULE TYPE:  oligonucleotide (ix) FEATURE:
             (A) NAME/KEY:  PCR primer (xi) SEQUENCE DESCRIPTION:  SEQ ID NO: 78:
```

GGACTCACCT GAGGAGACGG T                                              21

(2) INFORMATION FOR SEQ ID NO: 79:

```
        (i) SEQUENCE CHARACTERISTICS:
             (A) LENGTH:  21 bases
             (B) TYPE:  nucleic acid
             (C) STRANDEDNESS:  single
             (D) TOPOLOGY:  linear (ii) MOLECULE TYPE:  oligonucleotide (ix) FEATURE:
             (A) NAME/KEY:  PCR primer (xi) SEQUENCE DESCRIPTION:  SEQ ID NO: 79:
```

ACCGTCTCCT CAGGTGAGTC C                                              21

(2) INFORMATION FOR SEQ ID NO: 80:

```
        (i) SEQUENCE CHARACTERISTICS:
             (A) LENGTH:  21 bases
             (B) TYPE:  nucleic acid
             (C) STRANDEDNESS:  single
             (D) TOPOLOGY:  linear (ii) MOLECULE TYPE:  oligonucleotide (ix) FEATURE:
             (A) NAME/KEY:  PCR primer (xi) SEQUENCE DESCRIPTION:  SEQ ID NO: 80:
```

CCTAGTCCTT CATGACCTGA A                                              21

(2) INFORMATION FOR SEQ ID NO: 81:

```
        (i) SEQUENCE CHARACTERISTICS:
             (A) LENGTH:  21 bases
             (B) TYPE:  nucleic acid
             (C) STRANDEDNESS:  single
             (D) TOPOLOGY:  linear (ii) MOLECULE TYPE:  oligonucleotide (ix) FEATURE:
             (A) NAME/KEY:  PCR primer (xi) SEQUENCE DESCRIPTION:  SEQ ID NO: 81:
```

TTCAGGTCAT GAACGACTAG G                                        21

(2) INFORMATION FOR SEQ ID NO: 82:

(i) SEQUENCE CHARACTERISTICS:
        (A) LENGTH: 26 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 82:

GATCGGATCC CTATAAATCT CTGGCC                                   26

(2) INFORMATION FOR SEQ ID NO: 83:

(i) SEQUENCE CHARACTERISTICS:
        (A) LENGTH: 761 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: Nucleotide sequence encoding LO-CD2a VL chain.

(xi) SEQUENCE DESCRIPTION: SEQ ID NO: 83:

ATGATGAGTC CTGTCCAGTC CCTGTTTCTG TTATTGCTTT GGATTCTGGG TAAGTAGAGA    60
ATGAGTTACA GGACAAGAAT GGGGATGGAG GATGAGTTCT GACTGCCCAT GTTGGCTGTC   120
CATGTGTGGT AAGGCAGGTC CTATTTTCTA AGATGGACAC TTGAGATTCC ATTACTTGAT   180
AATGAGAAAT TACAGATGAG ATAGGATTTG TGCTAAGAGG ATTCTAATGT AGATGAGAAG   240
GTGTATGCCA TTTAGGATCT GCAACCGAAT TGTTTTGTGA AAAAGCATTT GGTATATTTT   300
TTAAAAATCA CAAACACAC CGGGATCTCA CAGGAAATGA GTAACAAAAA GTAATTCACA    360
AAGATTGGTT GCAAATTTTG CACATAACTT TGTTCTGATC TATTATAATT TCAGGAACCA   420
ATGGTGATGT TGTGCTGACC CAGACTCCAC CTACTTTATT GGCTACCATT GGACAATCAG   480
TCTCCATCTC TTGCAGGTCA AGTCAGAGTC TCTTACATAG TAGTGGAAAC ACCTATTTAA   540
ATTGGTTGCT ACAGAGGACA GGCCAATCTC CACAGCCGCT AATTTATTTG GTATCCAAAC   600
TGGAATCTGG GGTCCCCAAC AGGTTCAGTG GCAGTGGGTC AGGAACAGAT TCACACTCA    660
AAATCAGTGG AGTGGAAGCT GAGGATTTGG GGGTTTATTA CTGCATGCAA TTTACCCATT   720
ATCCGTACAC GTTTGGAGCT GGGACCAAGC TGGAACTGAA A                      761

(2) INFORMATION FOR SEQ ID NO: 84:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: polypeptide (ix) FEATURE:
        (A) NAME/KEY: Chimeric LO-CD2a VL Chain (xi) SEQUENCE DESCRIPTION: SEQ ID NO: 84:

Met Met Ser Pro Val Gln Ser Leu Phe

```
                -20                     -15
Leu Leu Leu Leu Trp Ile Leu Gly Thr Asn
        -10                    -5

Gly Asp Val Val Leu Thr Gln Thr Pro
 -1  +1                  5

Pro Thr Leu Leu Ala Thr Ile Gly Gln Ser
         10                  15

Val Ser Ile Ser Cys Arg Ser Gln Ser Leu
         20                  25

Leu His Ser Ser Gly Asn Thr Tyr Leu Asn Trp
 30              35                  40

Leu Leu Gln Arg Thr Gly Gln Ser Pro Gln
                 45                  50

Pro Leu Ile Tyr Leu Val Ser Lys Leu Glu
             55                  60

Ser Gly Val Pro Asn Arg Phe Ser Gly Ser
                 65                  70

Gly Ser Gly Thr Asp Phe Thr Leu Lys Ile
                 75                  80

Ser Gly Val Glu Ala Glu Asp Leu Gly Val
                 85                  90

Tyr Tyr Cys Met Gln Phe Thr His Tyr Pro
                 95                 100

Tyr Thr Phe Gly Ala Gly Thr Lys Leu Glu
                105                 110

Leu Lys
```

(2) INFORMATION FOR SEQ ID NO: 85:

(i) SEQUENCE CHARACTERISTICS:
        (A) LENGTH: 491 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: Nucleotide sequence encoding LO-CD2a VH chain.

(xi) SEQUENCE DESCRIPTION: SEQ ID NO: 85:

```
ATGAAATGCA GGTGGATCAT CCTCTTCTTG ATGGCAGTAG CTACAGGTAA GGCACTCCCA    60
AGTCCTAAAC TTGAGAGATC ATACACTTGG GAGACAGTGA CACTATCTTT GGATTTCTTT   120
CAACAGGGGT CAACTCAGAA GTCCAGCTGC AGCAATCTGG GCCTGAGCTT CAGAGACCCG   180
GGGCCTCAGT CAAGTTGTCG TGCAAGGCTT CTGGCTATAT ATTTACAGAA TACTATATGT   240
ACTGGGTGAA GCAGAGGCCT AAACAGGGCC TGGAATTAGT AGGAAGGATC GATCCTGAAG   300
ACGGTAGTAT TGATTATGTT GAGAAGTTCA AAAGAAGGC CACACTGACT GCAGATACAT    360
CGTCCAACAC AGCCTACATG CAACTCAGCA GCCTGACATC TGAGGACACA GCAACCTATT   420
TTTGTGCTAG GGAAAATTC AACTATCGAT TGCTTACTG GGGCCAAGGC ACCCTCGTCA     480
CAGTCTCCTC A                                                        491
```

(2) INFORMATION FOR SEQ ID NO: 86:

(i) SEQUENCE CHARACTERISTICS:
        (A) LENGTH: 137 amino acids

```
        (B) TYPE:  amino acid
        (C) STRANDEDNESS:
        (D) TOPOLOGY:  linear (ii) MOLECULE TYPE:  polypeptide (ix) FEATURE:
        (A) NAME/KEY:  Amino acid sequence of chimeric LO-CD2a VH
            chain.

(xi) SEQUENCE DESCRIPTION:  SEQ ID NO: 86:

Met Lys Cys Arg Trp Ile Ile Leu Phe Leu
-19           -15               -10

Met Ala Val Ala Thr Gly Val Asn Ser Glu
            -5              -1  +1

Val Gln Leu Gln Gln Ser Gly Pro Glu
            5               10

Leu Gln Arg Pro Gly Ala Ser Val Lys Leu
            15              20

Ser Cys Lys Ala Ser Gly Tyr Ile Phe Thr
            25              30

Glu Tyr Tyr Met Tyr Trp Val Lys Gln Arg
            35              40

Pro Lys Gln Gly Leu Glu Leu Val Gly Arg
            45              50

Ile Asp Pro Glu Asp Gly Ser Ile Asp Tyr
            55              60

Val Glu Lys Phe Lys Lys Lys Ala Thr Leu
            65              70

Thr Ala Asp Thr Ser Ser Asn Thr Ala Tyr
            75              80

Met Gln Leu Ser Ser Leu Thr Ser Glu Asp
            85              90

Thr Ala Thr Tyr Phe Cys Ala Arg Gly Lys
            95              100

Phe Asn Tyr Arg Phe Ala Tyr Trp Gly Gln
            105             110

Gly Thr Leu Val Thr Val Ser Ser
            115

(2) INFORMATION FOR SEQ ID NO: 87:

(i) SEQUENCE CHARACTERISTICS:
        (A) LENGTH:  112 amino acids
        (B) TYPE:  amino acid
        (C) STRANDEDNESS:
        (D) TOPOLOGY:  linear (ii) MOLECULE TYPE:  polypeptide (ix) FEATURE:
        (A) NAME/KEY:  Rat LO-CD2a light chain variable region.

(xi) SEQUENCE DESCRIPTION:  SEQ ID NO: 87:

Asp Val Val Leu Thr Gln Thr Pro Thr
            5               10

Leu Leu Ala Thr Ile Gly Gln Ser Val Ser
            15              20

Ile Ser Cys Arg Ser Ser Gln Ser Leu Leu
            25              30
```

His Ser Ser Gly Asn Thr Tyr Leu Asn Trp
                35                      40

Leu Leu Gln Arg Thr Gly Gln Ser Pro Gln
                45                      50

Pro Leu Ile Tyr Leu Val Ser Lys Leu Glu
                55                      60

Ser Gly Val Pro Asn Arg Phe Ser Gly Ser
                65                      70

Gly Ser Gly Thr Asp Phe Thr Leu Lys Ile
                75                      80

Ser Gly Val Glu Ala Glu Asp Leu Gly Val
                85                      90

Tyr Tyr Cys Met Gln Phe Thr His Tyr Pro
                95                      100

Tyr Thr Phe Gly Ala Gly Thr Lys Leu Glu
                105                     110

Leu Lys (2) INFORMATION FOR SEQ ID NO: 88:

(i) SEQUENCE CHARACTERISTICS:
        (A) LENGTH: 112 amino acids
        (B) TYPE:  amino acid
        (C) STRANDEDNESS:
        (D) TOPOLOGY:  linear (ii) MOLECULE TYPE:  polypeptide (ix) FEATURE:
        (A) NAME/KEY:  Humanized LO-CD2a light chain variable region.

(xi) SEQUENCE DESCRIPTION:  SEQ ID NO: 88:

Asp Val Val Met Thr Gln Ser Pro Pro Ser
                5                       10

Leu Leu Val Thr Leu Gly Gln Pro Ala Ser
                15                      20

Ile Ser Cys Arg Ser Ser Gln Ser Leu Leu
                25                      30

His Ser Ser Gly Asn Thr Tyr Leu Asn Trp
                35                      40

Leu Leu Gln Arg Pro Gly Gln Ser Pro Gln
                45                      50

Pro Leu Ile Tyr Leu Val Ser Lys Leu Glu
                55                      60

Ser Gly Val Pro Asp Arg Phe Ser Gly Ser
                65                      70

Gly Ser Gly Thr Asp Phe Thr Leu Lys Ile
                75                      80

Ser Gly Val Glu Ala Glu Asp Val Gly Val
                85                      90

Tyr Tyr Cys Met Gln Phe Thr His Tyr Pro
                95                      100

Tyr Thr Phe Gly Gln Gly Thr Lys Leu Glu
                105                     110

Ile Lys (2) INFORMATION FOR SEQ ID NO: 89:

(i) SEQUENCE CHARACTERISTICS:
        (A) LENGTH: 112 amino acids
        (B) TYPE: amino acid
        (C) STRANDEDNESS:
        (D) TOPOLOGY: linear (ii) MOLECULE TYPE: polypeptide (ix) FEATURE:
        (A) NAME/KEY: Light chain vairable region of HUM5400

(xi) SEQUENCE DESCRIPTION: SEQ ID NO: 89:

Asp Val Val Met Thr Gln Ser Pro Leu Ser
                  5                  10

Leu Pro Val Thr Leu Gly Gln Pro Ala Ser
                 15                  20

Ile Ser Cys Arg Ser Ser Gln Ser Leu Val
                 25                  30

Tyr Ser Asp Gly Asn Thr His Leu Asn Trp
                 35                  40

Phe Gln Gln Arg Pro Gly Gln Ser Pro Arg
                 45                  50

Arg Leu Ile Tyr Lys Val Ser Asn Arg Asp
                 55                  60

Ser Gly Val Pro Asp Arg Phe Ser Gly Ser
                 65                  70

Gly Ser Gly Thr Asp Phe Thr Leu Lys Ile
                 75                  80

Ser Arg Val Glu Ala Glu Asp Val Gly Val
                 85                  90

Tyr Tyr Cys Met Gln Gly Thr His Trp Pro
                 95                 100

Tyr Thr Phe Gly Gln Gly Thr Lys Leu Glu
                105                 110

Ile Lys (2) INFORMATION FOR SEQ ID NO: 90:

(i) SEQUENCE CHARACTERISTICS:
        (A) LENGTH: 807 bases
        (B) TYPE: nucleic acid
        (C) STRANDEDNESS: single
        (D) TOPOLOGY: linear (ii) MOLECULE TYPE: polynucleotide (ix) FEATURE:
        (A) NAME/KEY: Nucleotide sequence encoding humanized LO-CD2a
            light chain variable region.

(xi) SEQUENCE DESCRIPTION: SEQ ID NO: 90:

AAGCTTCATG ATGAGTCCTG TCCAGTCCCT GTTTCTGTTA TTGCTTTGGA TTCTGGGTAA      60

GTAGAGAATG AGTTACAGGA CAAGAATGGG GATGGAGGAT GAGTTCTGAC TGCCCATGTT     120

GGCTGTCCAT GTGTGGTAAG GCAGGTCCTA TTTTCTAAGA TGGACACTTG AGATTCCATT     180

ACTTGATAAT GAGAAATTAC AGATGAGATA GGATTTGTGC TAAGAGGATT CTAATGTAGA     240

TGAGAAGGTG TATGCCATTT AGGATCTGCA ACCGAATTGT TTTGTGAAAA AGCATTTGGT     300

ATATTTTTTA AAAATCACAA AACACACCGG GATCTCACAG GAAATGAGTA ACAAAAAGTA     360

ATTCACAAAG ATTGGTTGCA AATTTTGCAC ATAACTTTGT TCTGATCTAT TATAATTTCA     420

```
GGAACCAATG GTGATGTTGT GATGACCCAG AGTCCACCTT CATTATTGGT AACCTTGGGA      480

CAACCAGCTT CCATCTCTTG CAGGTCAAGT CAGAGTCTCT TACATAGTAG TGGAAACACC      540

TATTTAAATT GGTTGCTACA GAGGCCAGGC CAATCTCCAC AGCCGCTAAT TTATTTGGTA      600

TCCAAACTGG AATCTGGGGT CCCCGACAGG TTCAGTGGCT CAGGGAGTGG AACAGATTTC      660

ACACTCAAAA TCAGTGGAGT GGAAGCTGAG GATGTGGGGG TTTATTACTG CATGCAATTT      720

ACCCATTATC CGTACACGTT TGGACAAGGG ACCAAGCTGG AAATCAAACG TGAGTAGAAT      780

TTAAACTTTG CTTCCTCAGT TGGATCC                                          807

(2) INFORMATION FOR SEQ ID NO: 91:

(i) SEQUENCE CHARACTERISTICS:
         (A) LENGTH: 132 amino acids
         (B) TYPE:   amino acid
         (C) STRANDEDNESS:
         (D) TOPOLOGY:  linear (ii) MOLECULE TYPE:  polypeptide (ix) FEATURE:
         (A) NAME/KEY:  Humanized LO-CD2a light chain variable region.

(xi) SEQUENCE DESCRIPTION:  SEQ ID NO: 91:

Met Met Ser Pro Val Gln Ser Leu Phe Leu Leu
-20             -15                 -10

Leu Leu Trp Ile Leu Gly Thr Asn Gly Asp
             -5                 -1  +1

Val Val Met Thr Gln Ser Pro Pro Ser
                5             10

Leu Leu Val Thr Leu Gly Gln Pro Ala Ser
                15                  20

Ile Ser Cys Arg Ser Ser Gln Ser Leu Leu
                25                  30

His Ser Ser Gly Asn Thr Tyr Leu Asn Trp
                35                  40

Leu Leu Gln Arg Pro Gly Gln Ser Pro Gln
                45                  50

Pro Leu Ile Tyr Leu Val Ser Lys Leu Glu
                55                  60

Ser Gly Val Pro Asp Arg Phe Ser Gly Ser
                65                  70

Gly Ser Gly Thr Asp Phe Thr Leu Lys Ile
                75                  80

Ser Gly Val Glu Ala Glu Asp Val Gly Val
                85                  90

Tyr Tyr Cys Met Gln Phe Thr His Tyr Pro
                95                  100

Tyr Thr Phe Gly Gln Gly Thr Lys Leu Glu
                105                 110

Ile Lys (2) INFORMATION FOR SEQ ID NO: 92:

(i) SEQUENCE CHARACTERISTICS:
         (A) LENGTH: 118 amino acids
         (B) TYPE:   amino acid
         (C) STRANDEDNESS:
```

(D) TOPOLOGY:  linear (ii) MOLECULE TYPE:  polypeptide (ix) FEATURE:
        (A) NAME/KEY:  Rat LO-CD2a heavy chain variable region.

(xi) SEQUENCE DESCRIPTION:  SEQ ID NO: 92:

Glu Val Gln Leu Gln Gln Ser Gly Pro Glu
                  5                  10

Leu Gln Arg Pro Gly Ala Ser Val Lys Leu
                 15                  20

Ser Cys Lys Ala Ser Gly Tyr Ile Phe Thr
                 25                  30

Glu Tyr Tyr Met Tyr Trp Val Lys Gln Arg
                 35                  40

Pro Lys Gln Gly Leu Glu Leu Val Gly Arg
                 45                  50

Ile Asp Pro Glu Asp Gly Ser Ile Asp Tyr
                 55                  60

Val Glu Lys Phe Lys Lys Ala Thr Leu
                 65                  70

Thr Ala Asp Thr Ser Ser Asn Thr Ala Tyr
                 75                  80

Met Gln Leu Ser Ser Leu Thr Ser Glu Asp
                 85                  90

Thr Ala Thr Tyr Phe Cys Ala Arg Gly Lys
                 95                 100

Phe Asn Tyr Arg Phe Ala Tyr Trp Gly Gln
                105                 110

Gly Thr Leu Val Thr Val Ser Ser
                115

(2) INFORMATION FOR SEQ ID NO: 93:

(i) SEQUENCE CHARACTERISTICS:
        (A) LENGTH: 118 amino acids
        (B) TYPE:  amino acid
        (C) STRANDEDNESS:
        (D) TOPOLOGY:  linear (ii) MOLECULE TYPE:  polypeptide (ix) FEATURE:
        (A) NAME/KEY:  Humanized LO-CD2a heavy chain variable region.

(xi) SEQUENCE DESCRIPTION:  SEQ ID NO: 93:

Gln Val Gln Leu Val Gln Ser Gly Ala Glu
                  5                  10

Val Lys Lys Pro Gly Ala Ser Val Lys Val
                 15                  20

Ser Cys Lys Ala Ser Gly Tyr Thr Phe Thr
                 25                  30

Glu Tyr Tyr Met Tyr Trp Val Arg Gln Ala
                 35                  40

Pro Gly Gln Gly Leu Glu Leu Met Gly Arg
                 45                  50

Ile Asp Pro Glu Asp Gly Ser Ile Asp Tyr
                 55                  60

```
Val Glu Lys Phe Lys Lys Val Thr Leu
                65              70

Thr Ala Asp Thr Ser Ser Thr Ala Tyr
                75              80

Met Glu Leu Ser Ser Leu Thr Ser Asp Asp
                85              90

Thr Ala Val Tyr Tyr Cys Ala Arg Gly Lys
                95              100

Phe Asn Tyr Arg Phe Ala Tyr Trp Gly Gln
                105             110

Gly Thr Leu Val Thr Val Ser Ser
                115
```

(2) INFORMATION FOR SEQ ID NO: 94:

(i) SEQUENCE CHARACTERISTICS:
        (A) LENGTH: 123 amino acids
        (B) TYPE:   amino acid
        (C) STRANDEDNESS:
        (D) TOPOLOGY:  linear (ii) MOLECULE TYPE:  polypeptide (ix) FEATURE:
        (A) NAME/KEY:  Human Amu 5-3 heavy chain variable region.

(xi) SEQUENCE DESCRIPTION:  SEQ ID NO: 94:

```
Gln Val Gln Leu Val Gln Ser Gly Ala Glu
                5               10

Val Lys Lys Pro Gly Ala Ser Val Lys Val
                15              20

Ser Cys Lys Ala Ser Gly Tyr Thr Phe Thr
                25              30

Gly Tyr Tyr Met His Trp Val Arg Gln Ala
                35              40

Pro Gly Gln Gly Leu Glu Trp Met Gly Arg
                45              50

Ile Asn Pro Asn Ser Gly Gly Thr Asn Tyr
                55              60

Ala Gln Lys Phe Gln Gly Arg Val Thr Met
                65              70

Thr Arg Asp Thr Ser Ile Ser Thr Ala Tyr
                75              80

Met Glu Leu Ser Arg Leu Arg Ser Asp Asp
                85              90

Thr Ala Val Tyr Tyr Cys Ala Arg Gly Arg
                95              100

Thr Glu Tyr Ile Val Val Ala Glu Gly Phe
                105             110

Asp Tyr Trp Gly Gln Gly Thr Leu Val Thr
                115             120

Val Ser Ser
```

(2) INFORMATION FOR SEQ ID NO: 95:

(i) SEQUENCE CHARACTERISTICS:
        (A) LENGTH: 701 bases
        (B) TYPE:   nucleic acid
        (C) STRANDEDNESS:  single

```
        (D) TOPOLOGY:  linear (ii) MOLECULE TYPE:  polynucleotide (ix) FEATURE:
         (A) NAME/KEY:  Nucleotide sequence encoding LO-CD2a heavy
             chain variable region.

(xi) SEQUENCE DESCRIPTION:  SEQ ID NO: 95:

AAGCTTCATG AAATGCAGGT GGATCATCCT CTTCTTGATG GCAGTAGCTA CAGGTAAGGC     60

ACTCCCAAGT CCTAAACTTG AGAGATCATA CACTTGGGAG ACAGTGACAC TATCTTTGGA    120

TTTCTTTCAA CAGGGGTCAA CTCACAGGTG CAGCTGGTGC AGTCTGGGGC TGAGGTGAAG    180

AAGCCTGGGG CCTCAGTGAA GGTCTCCTGC AAGGCTTCTG GATACACCTT CACCGAGTAC    240

TATATGTACT GGGTGCGACA GGCCCCTGGA CAAGGGCTTG AGCTGATGGG AAGGATCGAT    300

CCTGAAGACG GTAGTATTGA TTATGTTGAG AAGTTTAAGA AAAGGTCAC CCTGACCGCT     360

GACACGTCCT CTAGCACAGC CTACATGGAG CTGAGCAGCC TGACCTCTGA CGACACGGCC    420

GTGTATTACT GTGCGAGAGG AAAGTTTAAC TATAGGTTTG CTTACTGGGG CCAAGGAACC    480

CTGGTCACCG TCTCCTCAGG TGAGTCCTTA CAACCTCTCT CTTCTATTCA GCTTAAATAG    540

ATTTTACTGC ATTTGTTGGG GGGAAATGT GTGTATCTGA ATTTCAGGTC ATGAAGGACT     600

AGGGACACCT TGGGAGTCAG AAAGGGTCAT TGGGAGCCCG GGCTGATGCA GACAGACATC    660

CTCAGCTCCC GGACTTCATG GCCAGAGATT TATAGGGATC C                       701

(2) INFORMATION FOR SEQ ID NO: 96:

(i) SEQUENCE CHARACTERISTICS:
        (A) LENGTH: 137 amino acids
        (B) TYPE:  amino acid
        (C) STRANDEDNESS:
        (D) TOPOLOGY:  linear (ii) MOLECULE TYPE:  polypeptide (ix) FEATURE:
         (A) NAME/KEY:  Humanized LO-CD2a heavy chain variable region.

(xi) SEQUENCE DESCRIPTION:  SEQ ID NO: 96:

Met Lys Cys Arg Trp Ile Ile Leu Phe Leu
-19            -15                  -10

Met Ala Val Ala Thr Gly Val Asn Ser Gln
              -5                 -1   1

Val Gln Leu Val Gln Ser Gly Ala Glu
                5                 10

Val Lys Lys Pro Gly Ala Ser Val Lys Val
                15                    20

Ser Cys Lys Ala Ser Gly Tyr Thr Phe Thr
                25                    30

Glu Tyr Tyr Met Tyr Trp Val Arg Gln Ala
                35                    40

Pro Gly Gln Gly Leu Glu Leu Met Gly Arg
                45                    50

Ile Asp Pro Glu Asp Gly Ser Ile Asp Tyr
                55                    60

Val Glu Lys Phe Lys Lys Lys Val Thr Leu
                65                    70

Thr Ala Asp Thr Ser Ser Ser Thr Ala Tyr
                75                    80
```

-continued

```
Met Glu Leu Ser Ser Leu Thr Ser Asp Asp
                85                  90

Thr Ala Val Tyr Tyr Cys Ala Arg Gly Lys
                95                  100

Phe Asn Tyr Arg Phe Ala Tyr Trp Gly Gln
                105                 110

Gly Thr Leu Val Thr Val Ser Ser
                115
```

COMPOSITION COMPRISING THE LO-CD2A ANTIBODY

This application is a continuation of U.S. patent application Ser. No. 08/472,281, filed Jun. 7, 1995, now U.S. Pat. No. 5,817,311, which is a continuation-in-part of U.S. patent application Ser. No. 08/407,009, filed Mar. 29, 1995, now abandoned, which is a continuation-in-part of U.S. patent application Ser. No. 08/119,032, filed Sep. 9, 1993, abandoned, which is a continuation-in-part of U.S. patent application Ser. No. 08/027,008 filed Mar. 5, 1993, now abandoned.

BACKGROUND OF THE INVENTION

A. Field of the Invention

This invention relates to an antibody (or fragment or derivative thereof) and preferably, to an antibody (or fragment or derivative thereof) which binds to human lymphocytes. More particularly, this invention relates to preventing and/or inhibiting on-going immune responses in a patient through the administration of such antibody (or fragment or derivative thereof) to a patient. Preferably, this invention relates to preventing or inhibiting T cell activation and proliferation through the administration of such antibody or fragment or derivative thereof to a patient.

B. Description of the Related Art

The prior art has disclosed the possibility of using antibodies to CD2 antigen for inhibiting graft rejection. In general, the prior art discloses the use of antibodies which bind to CD2 antigens as being possibly useful for inhibiting graft rejection, see, Ortho Pharmaceutical Corp., U.S. Pat. Nos. 4,364,973; 4,614,720; 4,515,893; 4,743,681; and 4,798,806.

Such antibodies have not been known to be useful in inhibiting graft rejection in human patients or in non-human primates. As exemplified in the following references, J. V. Giorgi, et al., *Immunosuppressive Effect and Immunogenicity of OKT11A Monoclonal Antibody in Monkey Allograft Recipients*, Transplantation Proceedings Vol. XV No. 1, March 1983, and P. J. Thurlow, et al., *A Monoclonal Anti-Pan-T-Cell Antibody*, Transplantation, Vol. 36, No. 3, Pg. 293-298.

DETAILED DESCRIPTION OF THE FIGURES

FIG. 1

Two color staining of peripheral blood mononuclear cells (PBMC) with biotinylated LO-CD2a and Leu-5bPE.

For this staining, the following parameters were followed:
PARAMETER:FL1-H\(LOG)   FL2-h(LOG)   QUAD LOCATION: 17.15,9

| TOTAL = 5000 | | GATED = 1290 | | | |
|---|---|---|---|---|---|
| QUAD | EVENTS | % GATED | % TOTAL | X MEAN | Y MEAN |
| 1UL | 299 | 23.18 | 3.98 | 11.41 | 284.69 |
| 2UR | 831 | 65.97 | 17.02 | 32.70 | 630.65 |
| 3LL | 135 | 10.47 | 2.70 | 4.08 | 3.31 |
| 4LR | 5 | 0.39 | 0.10 | 25.11 | 6.54 |

FIG. 2

Human PBMC were stained with LO-CD2a-FITC and then a) stained with T11-PE(Coulter antibody to CD2) conjugated with phycoerythrin (PE) or b) Leu-5B-PE (Becton Dickinson antibody to CD2) conjugated to phycoerythrin (PE). In neither case was staining by the second antibody altered by pretreatment with LO-CD2a.

Figure 3B:
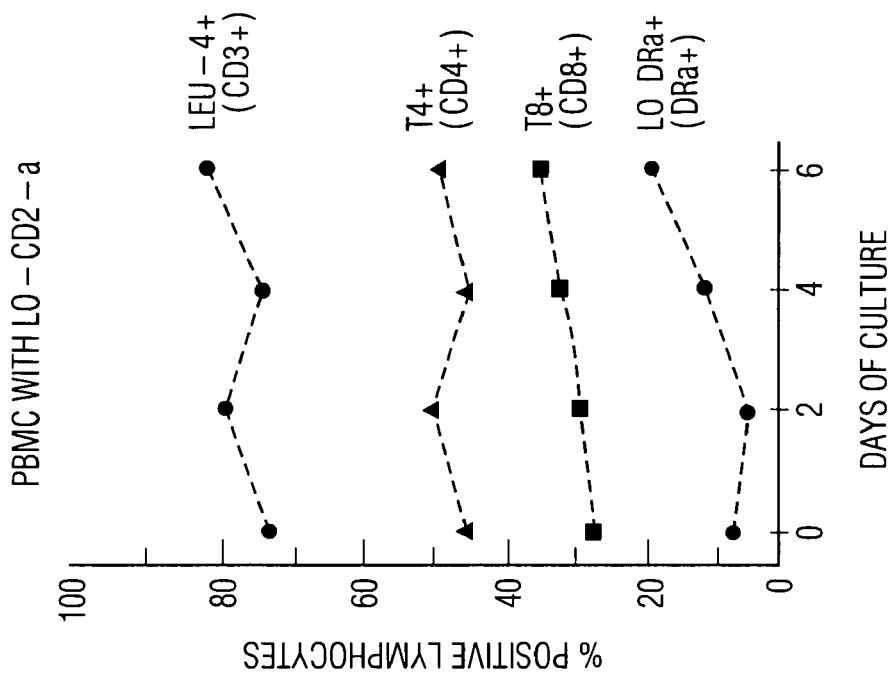
Figure 3A:
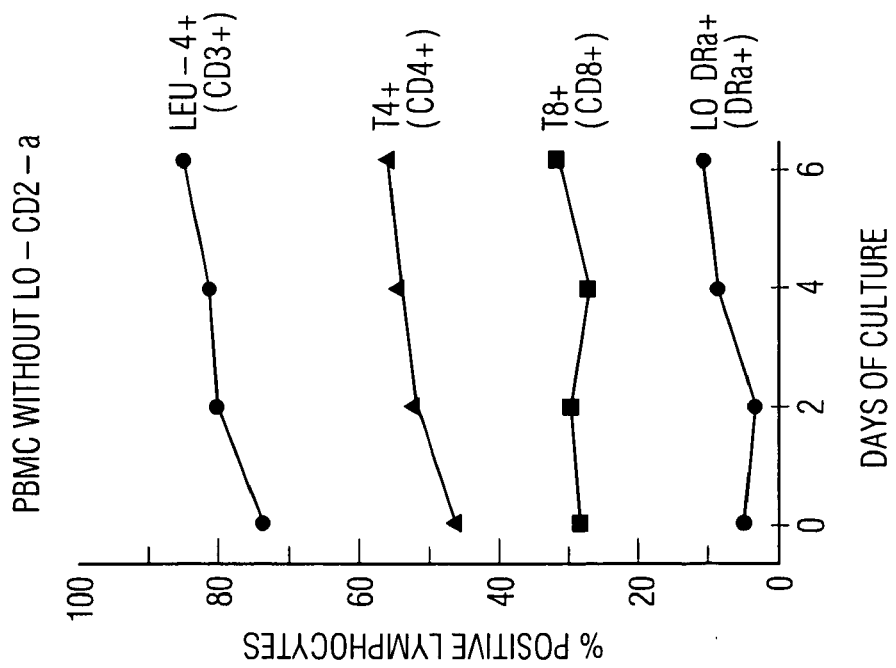

FIGS. 3a and 3b

Effects of LO-CD2a on membrane markers. PBMC at $2 \times 10^6$ cells/ml were cultured in the absence (solid lines) or in the presence (broken lines) of LO-CD2a (200 ng/ml). At the times indicated in the figures, cells were harvested and treated for cytofluorometric analysis. a) and b); PBMC were labeled with anti-CD3 (Leu-4a-FITC), anti-CD4 (T4–RD) mAbs, anti-class II antigens (LO-DRa-FITC) or anti-CD8 (T8–RD) monoclonal antibodies (mAbs). Negative controls for commercial mouse mAbs were aliquots of the same cells stained with FITC or Rhodamine-labeled mouse IgGs. Negative controls for rat mAbs were cells incubated with normal rat serum followed by a FITC-labeled mouse anti-rat mAb (MARK-FITC). Results are expressed as percentage positive cells.

FIG. 4

Effects of LO-CD2a on membrane markers and human blood lymphocyte culture with and without addition of LO-CD2a. Lymphocyte Cultures at $1 \times 10^6$ cells ml were labeled with (a) anti-CD2 (Leu-5b–FITC), anti-CD4 (T4–RD1) mAb, or anti-CD8 (T8–RD) mAb at times indicated. Negative controls for commercial mouse mAbs were aliquots of the same cells stained with FITC or Rhodamine-labeled mouse IgGs. Negative controls for rat mAbs were cells incubated with normal rat serum followed by a FITC-labeled mouse anti-rat mAb (MARK-FITC). Results are expressed as percentage of positive cells.

Figure 5B:
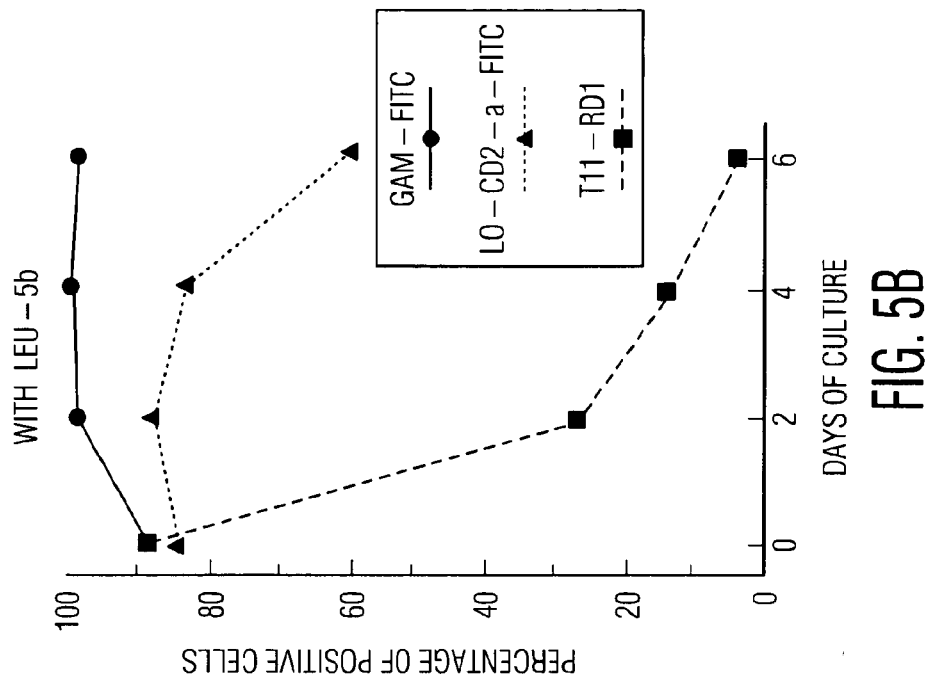
Figure 5A:
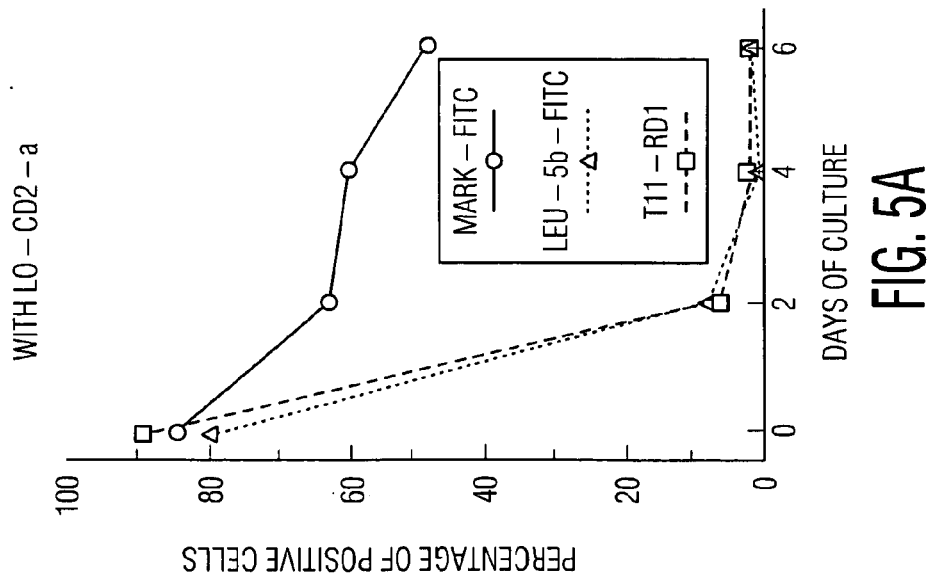

FIGS. 5a and 5b

Effects of LO-CD2a and Leu-5b on CD2 expression. Human PBMC were incubated with a) LO-CD2a (200 ng/ml) or b) Leu-5b (dialyzed against PBS, diluted 1:2) for the times indicated and a) stained for expression of CD2 (Leu-5b–FITC and T11-RD1) and for binding of LO-CD2a (Mark-3-FITC) or b) CD2 (LO-CD2a-FITC, T11-RD1) and for binding of Leu-5b Goat anti-mouse (GAM-FITC).

FIG. 6

Effects of LO-CD2a on MLR. a) inhibition of MLR in mixed lymphocyte cultures incubated for 6 days in the presence of increasing concentrations of LO-CD2a added at time 0. Cultures were harvested at day 6; b) inhibition of MLR in mixed lymphocyte cultures incubated with different concentrations of LO-CD2a added at time 0. Cultures were harvested at 24 h intervals; c) $^3$H-Thymidine (3H-T) incorporation (cpm) by mixed lymphocyte cultures in the absence (solid line) or in the presence (broken line) of LO-CD2a (200 ng/ml); d) inhibition of MLR by LO-CD2a (200 ng/ml) added at different times after the start of incubation. Cultures were harvested at day 6. All cultures were made in triplicate ($1 \times 10^6$ cells of each donor/ml) in a final volume of 200 il/well. $^3$H-Thymidine was added 8 h before harvesting cultures. Results in c) are shown as cpm$\times 10^{-3}$ incorporated per well harvested at the time indicated. Results in a), b) and d) are expressed as percentage inhibition of MLR of triplicate cultures (mean ±S.D.), as compared to control cultures (without LO-CD2a).

FIG. 7

Effects of LO-CD2a on blast cells during MLC. Peripheral blood mononuclear cells were cultured in mixed lymphocyte cultures with or without the addition of 200 ng/ml of LO-CD2a. At the indicated times cells were removed and analyzed by flow cytometry after staining with antibody to CD2 (Leu5b-FITC). Blast cells were gated by forward and side scatter and the expression of the indicated markers quantified on the blast cells.

Figure 8A:
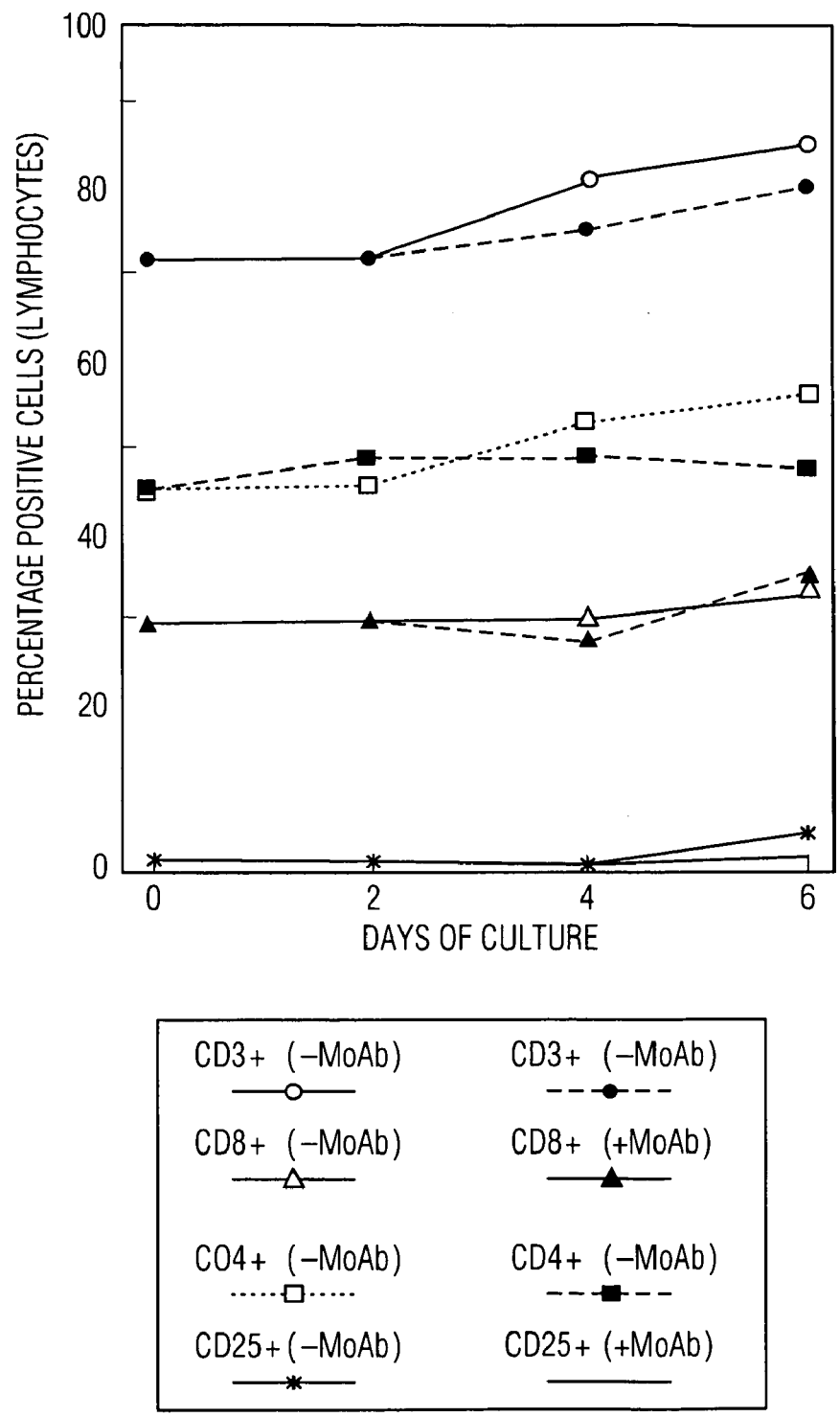
Figure 8B:
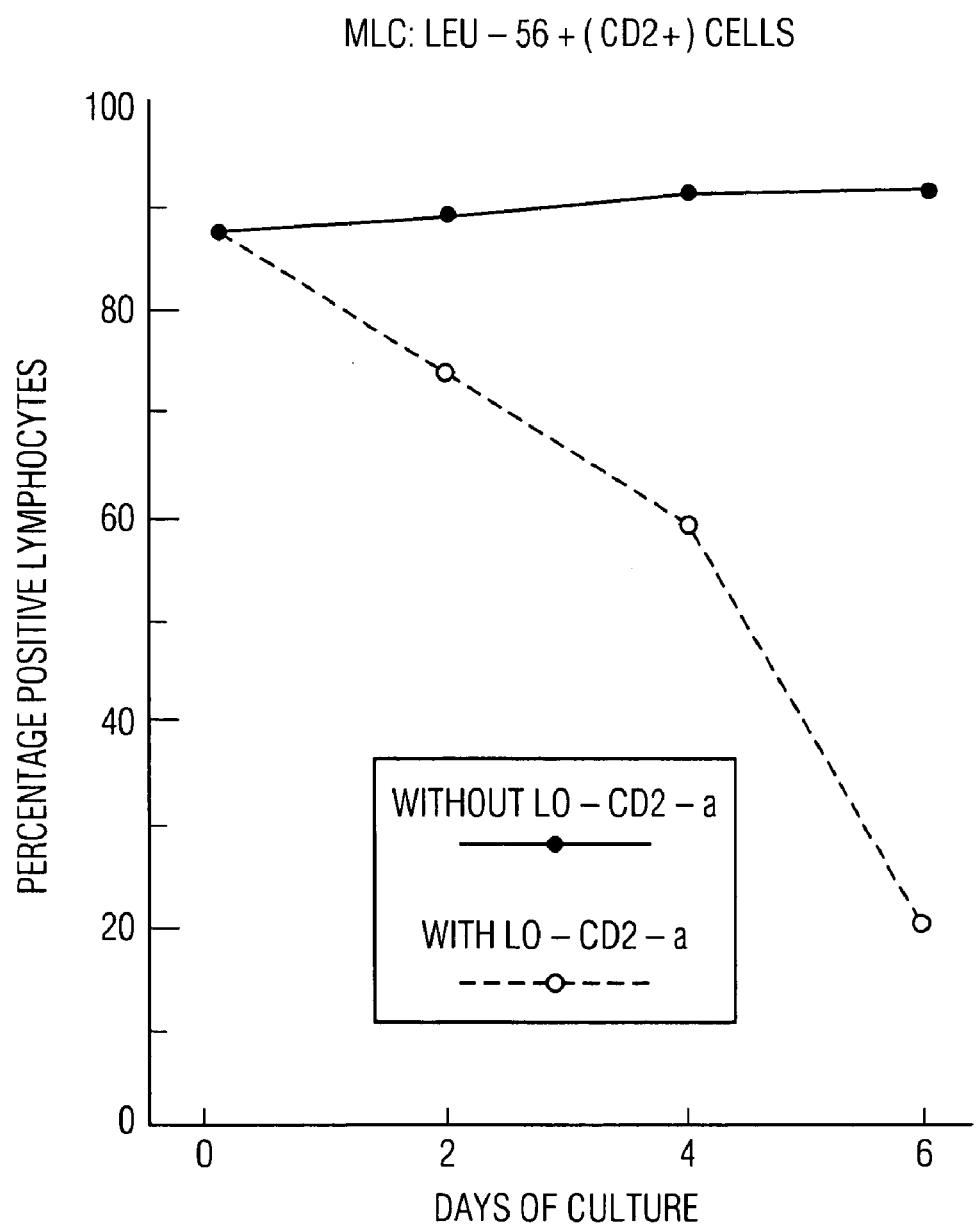

FIGS. 8a and 8b

Effects of LO-CD2a on resting cells during MLC. Human lymphocytes were cultured with and without the addition of LO-CD2a (200 ng/ml). At the indicated times cells were removed and stained for CD3 (Leu 4a-FITC), CD4 (T4–RD1) CD8 (T8–RD1) or CD25 (LO-TACT-1-FITC). The resting lymphocytes were identified by differential gating for size and granularity and the results are expressed as the percent of total resting lymphocytes staining with the indicated antibody. (FIG. 8a.) The percentage of resting cells positively stained by Leu-5b in cultures with and without LO-CD2a is shown in FIG. 8b.

FIG. 9

Effects of LO-CD2a on mitogen-stimulated lymphocytes. PBMC were cultured for 96 h in the absence or in the presence of OKT3 (100 ng/ml), Con-A (10 ìg/ml) and PHA (1 ìg/ml). In parallel cultures, LO-CD2a (200 ng/ml) was added 1 h after mitogens (gray bars) or 1 h before mitogens (blank bars). Checked bars represent cultures performed in the presence of LO-CD2a alone. Cultures (in triplicate) were pulse-labeled with $^3$H-Thymidine during the last 8 h of incubation.

FIG. 10

Effects of LO-CD2a on mitogen-driven activation of PMBC. PMBCs from two donors were cultured for 96 h in the presence of OKT3 (100 ng/ml), CON-A (10 ìg/ml) and PHA (1 ìg/ml). In parallel cultures, LO-CD2a (200 ng/ml) was added at Day 0 (0 h) after the initiation of the culture, Day 1 (24 h), or Day 2 (48 h). The graph depicts the percentage inhibition by LO-CD2a of the mitogen-induced proliferation in each donor.

Figure 11B:
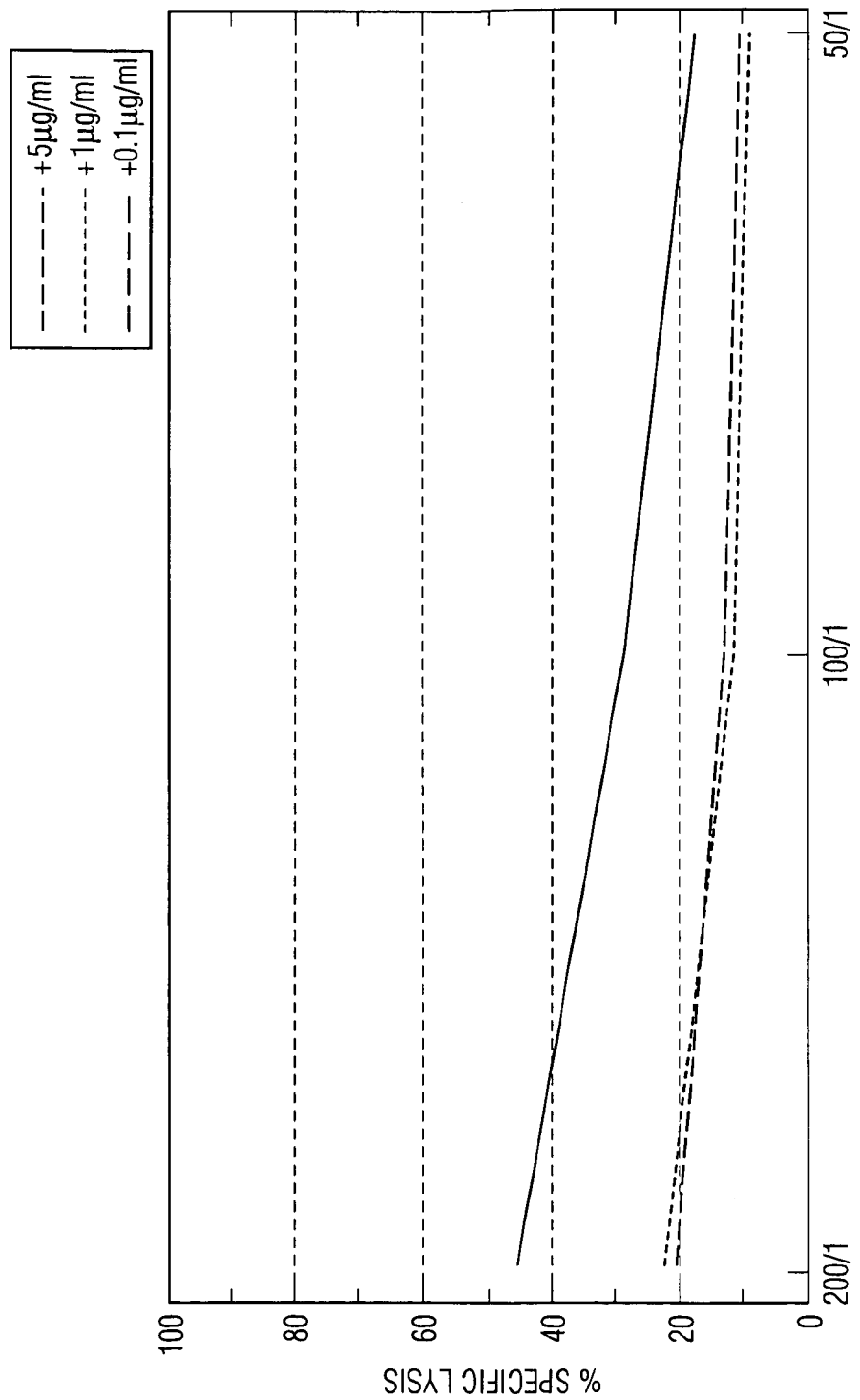

FIGS. 11a and 11b

Inhibition of NK activity by incubation of the effector and target cells ($^{51}$CR labeled K562 cells) in the presence of LO-CD2a. Three concentrations of LO-CD2a have been tested: 5 ìg/ml, 1 ìg/ml, 0.5 ìg/ml. Effector cells were peripheral blood lymphocytes of NK activity is expressed as percent lysis of labeled target cells. Two normal subjects were tested at 3 E/T ratios: 200/1, 200/1, 50/1.

FIG. 12

Total lymphocytes per ìl of peripheral blood of a cynomolgus monkey receiving 20 mg/day of LO-CD2a for 10 days (days 0-9).

FIG. 13

PBMC from the cynomolgus monkey receiving LO-CD2a at 20 mg/day for 10 days (day 0 to 9) were stained with monoclonal antibodies to CD2 (Leu-5b), CD4 (Leu3a), CD8 (Leu 2a), Natural Killer cells (CD8 and CD11b), and B cells (anti-IgM) on the days indicated and analyzed by flow cytometry. Results are presented as the percentage of the total number of staining cells per microliter of blood.

FIG. 14

NK activity of a cynomolgus monkey receiving 20 mg/day of LO-CD2a for 10 days (day 0-9). NK activity was assayed on days 11 and 22 and presented as % lysis at E/T of 25/1, 50/1 and 100/1.

FIG. 15

Serum concentration of LO-CD-2a of a cynomolgus monkey receiving the antibody at 20 mg/day for 10 days (day 0-9). The monoclonal antibody was measured by ELISA as described in the text and expressed in ìg/ml.

FIG. 16

Development of IgG antibody to LO-CD2a in a cynomolgus monkey receiving 20 mg/day of LO-CD2a for 10 days (days 0-9). The antibody to the monoclonal antibody was measured in serial dilutions of serum drawn on the indicated days by the sandwich ELISA described in the text and is expressed as the optical density at 492 nm.

Figure 17B:
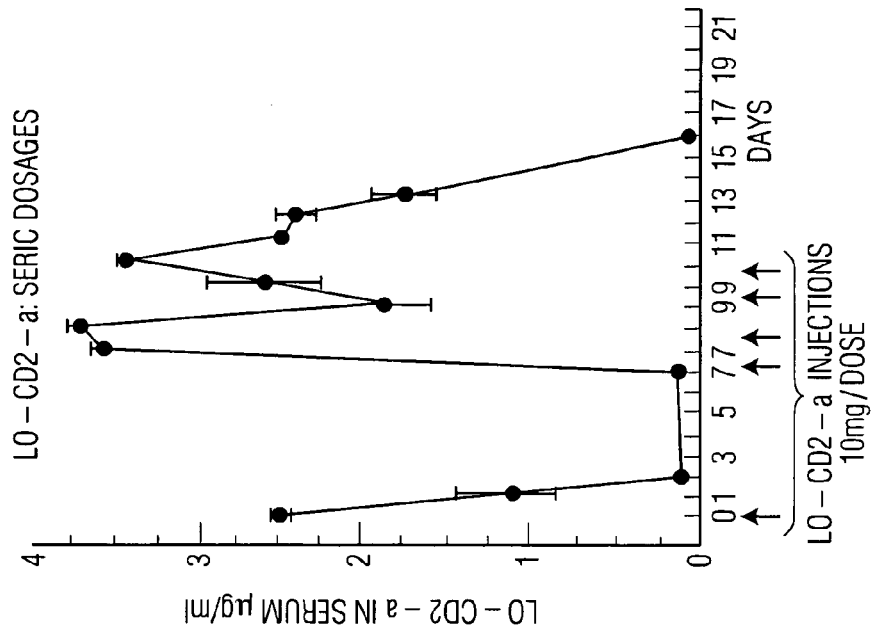
Figure 17A:
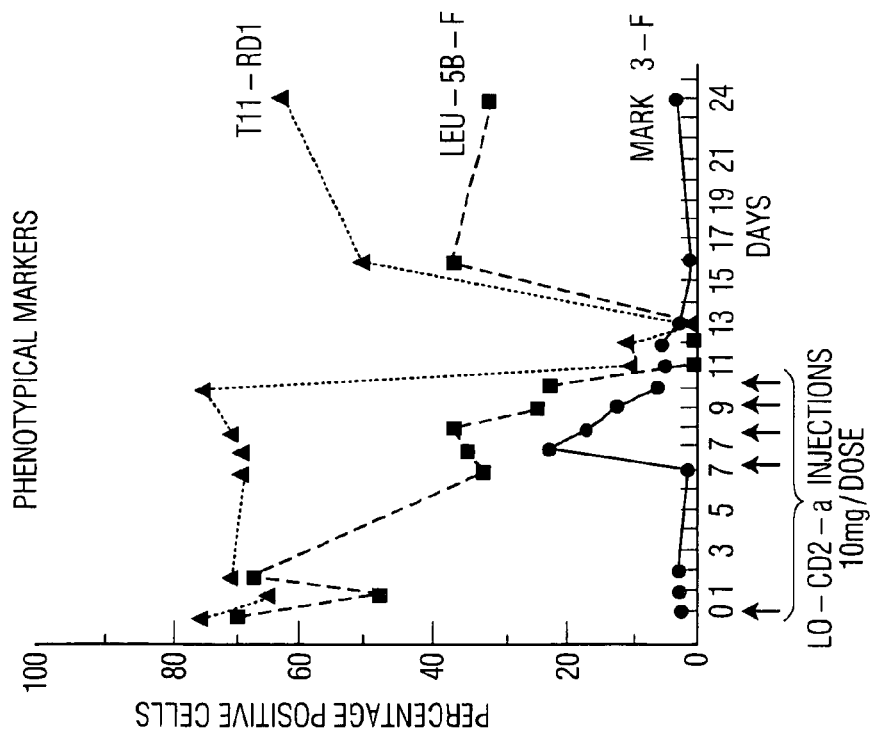

FIGS. 17a and 17b

Effect of LO-CD2a on baboon lymphocytes.

a) On the days indicated blood was obtained from the baboon and cells were stained with the anti-CD2 antibodies T11-RD1 and Leu-5b–FITC, LO-CD2a and MARK3-FITC, a mouse anti-rat kappa 1b antibody coupled to FITC to detect bound LO-CD2a.

b) Serum samples taken on the indicated days were evaluated for levels of LO-CD2a by ELISA.

Figures 18A, 18B:
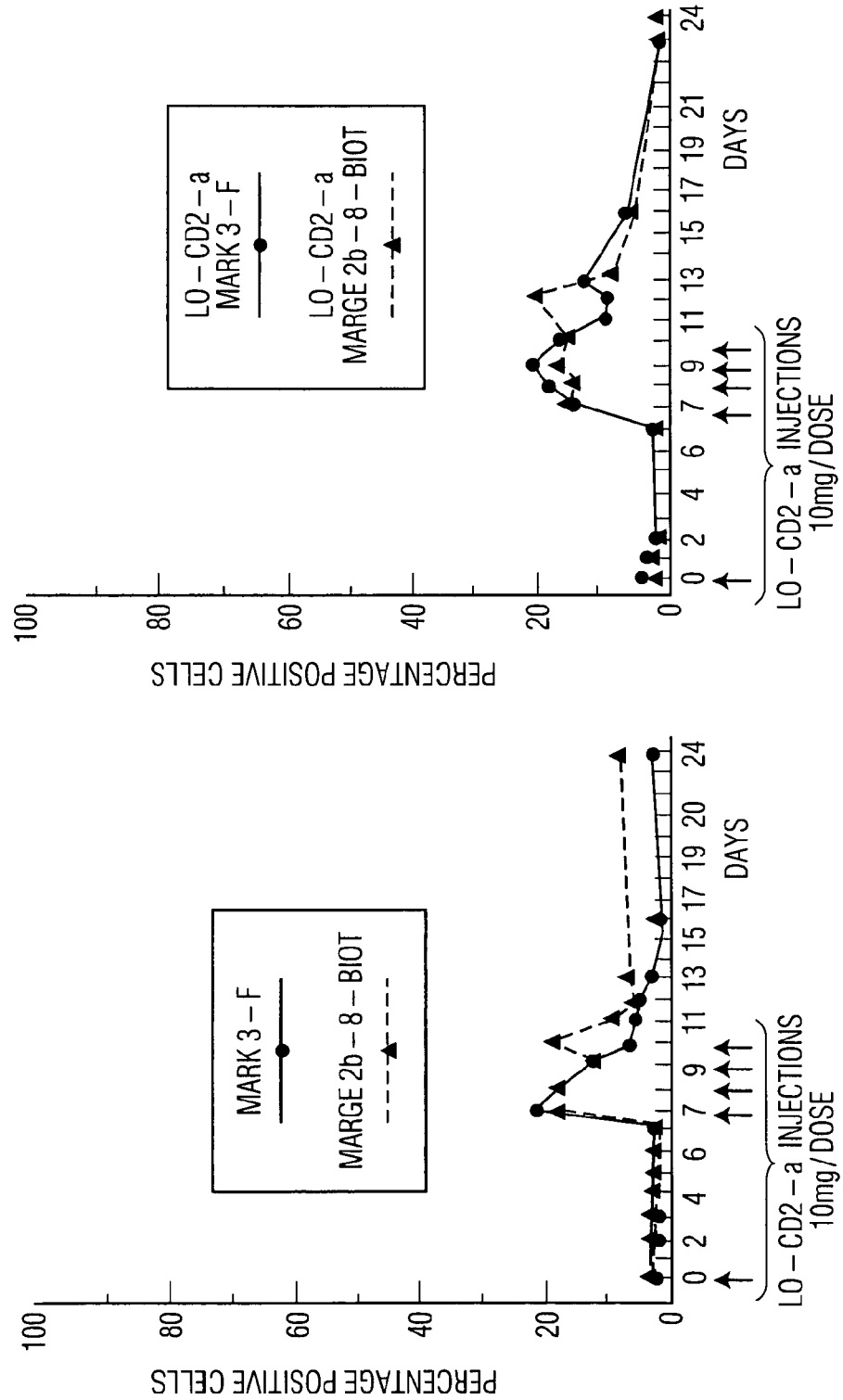

FIGS. 18a and 18b

Effect of LO-CD2a on baboon lymphocytes.

On the indicated days blood was taken and the cells stained to detect bound LO-CD2a with MARK3-FITC and MARK2b-8-biotin (a mouse monoclonal anti-rat IgG2b antibody coupled to biotin) detected with PE-coupled streptavidin.

a) No pretreatment of cells;

b) incubation with 2.5 ìg/ml LO-CD2a prior to staining to detect any sites unoccupied by circulating antibody.

FIG. 19

Effect of LO-CD2a on baboon lymphocytes.

On the indicated days blood samples were taken and stained with T4–RD1 (CD4); T8–RD1 (CD8) or MARK3-FITC (bound LO-CD2a).

FIG. 20

Leukocytes, lymphocytes and creatinine in patient #1 treated with ATG then LO-CD2a for allograft rejection.

FIG. 21

Serum levels of LO-CD2a during and following treatment in patient #1.

FIG. 22

Creatinine in patient #2 prior to, during and following treatment with LO-CD2a.

FIG. 23

Leukocyte and lymphocyte counts in patient #2 prior to, during and following treatment with LO-CD2a.

FIG. 24

Serum levels of LO-CD2a in patient #2, drawn just prior to and 2.5 hours after each injection.

FIG. 25

Leukocyte count, lymphocyte count and serum creatinine level in patient #3 receiving LO-CD2a for rejection of renal allograft.

FIG. 26

Dual color staining with LO-CD2a and (2) Leu5b, (3) Leu 4(CD3), (4) Leu3a(CD4), (5) Leu2b(CD8) and (6) Leu11 (anti-CD16) a marker for NK cells. LO-CD2a binding was detected with goat anti-rat IG-FITC. The upper set (1-6) of two color histograms shows the double staining. The low set (7-12) shows single staining with each antibody.

FIG. 27

Two color staining of human PBL with a rat isotype control for LO-CD2a (Pharmingen, purified rat IgG2b, kappa) or LO-CD2a and phycoerthyrin conjugated antibodies to CD4 (c,d), Cd8 (e,f), CD16(g,h), CD19(i,j) and CD2 (k,l). LO-CD2a and the isotype control were detected with FITC conjugated affinity purified F(ab')2 anti-rat immunoglobulin (Southern Biotechnology). The antibodies to the CD antigens were all phycoerthrin conjugated antibodies obtained from Becton-Dickinson [CD4(Leu3a), CD8(Leu2a), CD16(Leu-11b), CD19(Leu 12) and CD2 (Leu5b)]. In each case staining with the isotype control is shown in the first histogram and the LO-CD2a in the second histogram. Histogram a shows the pattern with the isotype control and b with LO-CD2a.

FIG. 28

Cytofluorograph analysis of the staining of COS cells transfected with wild-type CD2. The left panels show the histograms of staining of a COS cell transfected with the control vector, not containing CD2; the right set of panels staining of a COS cell transiently transfected with a vector containing the entire CD2 molecule. In each set the top histogram shows the staining with murine W632 (antibody to Class I, known to be expressed by COS cells) and 76-2-11 (an isotype control for the murine W632); the middle panel shows staining with Leu5b (anti-CD2 from Becton Dickinson) and 76-2-11. an isotype matched control for Leu5b staining, the bottom panel staining with LO-CD2a and a rat isotype matched control for LO-CD2a.

FIG. 29

Nucleotide (SEQ ID NO:83) and amino acid (SEQ ID NO:84) sequences of the chimeric LO-CD2a $V_l$ chain.

FIG. 30

Nucleotide (SEQ ID NO:85) and amino acid (SEQ ID NO:86) sequences of the chimeric LO-CD2a $V_H$ chain.

FIG. 31

Amino acid sequences of the light chain variable region of rat LO-CD2a (SEQ ID NO:87), human HUM5400 (SEQ ID NO:89), and humanized LO-CD2a (SEQ ID NO:88).

FIG. 32

Nucleotide (SEQ ID NO:90) and amino acid (SEQ ID NO:91) sequences of the humanized LO-CD2a variable region.

FIG. 33

Amino acid sequences of the heavy chain variable region of rat LO-CD2a (SEQ ID NO:92), human Amu 5-3 (SEQ ID NO:94), and humanized LO-CD2a (SEQ ID NO:93).

FIG. 34

Nucleotide (SEQ ID NO:95) and amino acid (SEQ ID NO:96) sequences of the humanized LO-CD2a heavy chain variable region.

FIG. 35

Binding of rat LO-CD2a, humanized LO-CD2a to Jurkat cells.

FIG. 36

Induction of hyporesponsiveness in vitro by rat LO-CD2a, humanized LO-CD2a, and control rat and human immunoglobulins.

FIGS. 37A, 37B, and 37C

Inhibition of primary MLR by LO-CD2a and response of T-cells cultured with LO-CD2a in a primary MLR to an antigen in a secondary MLR or a third party stimulator in an MLR.

Figure 38A:
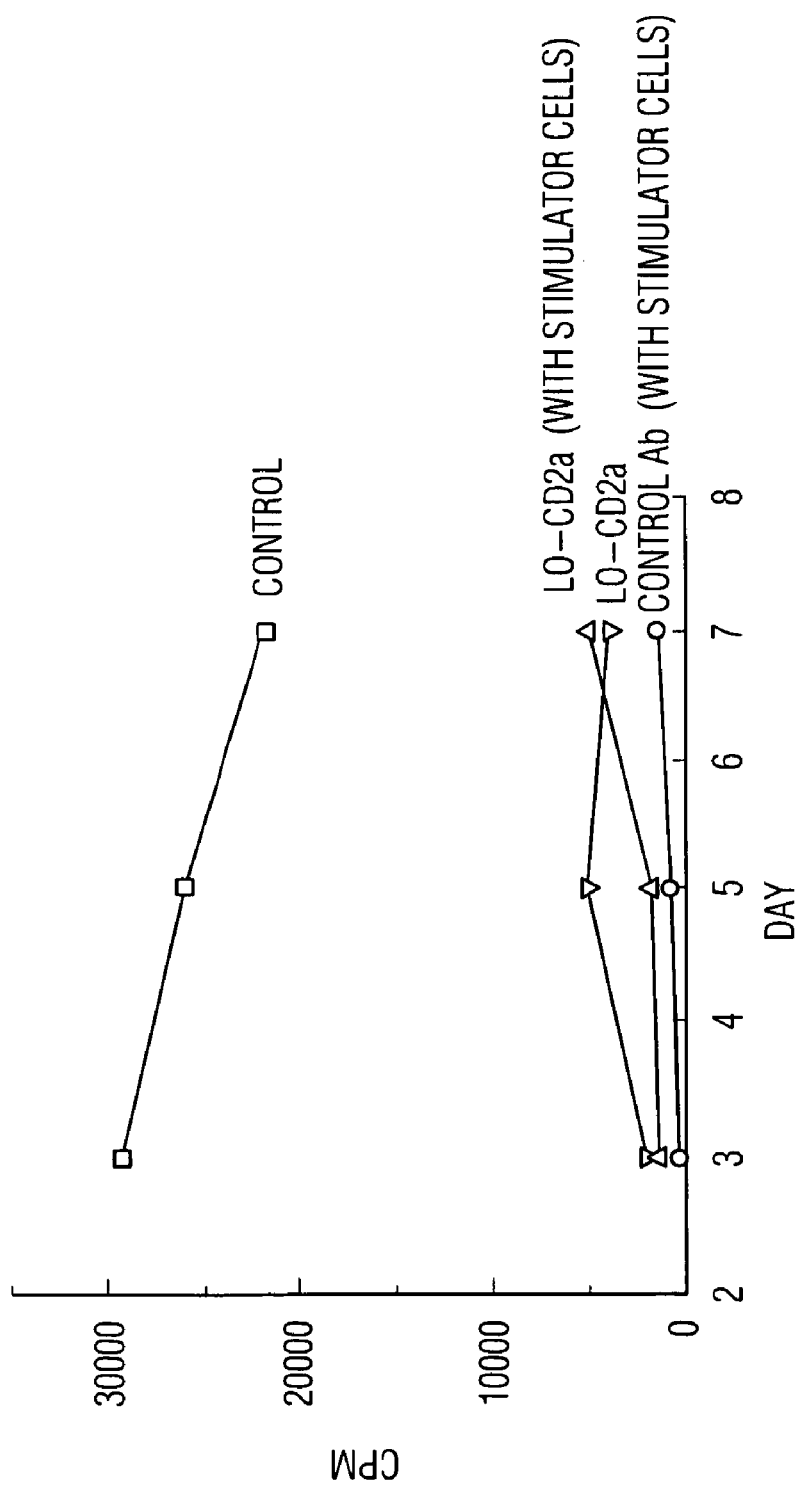
Figure 38B:
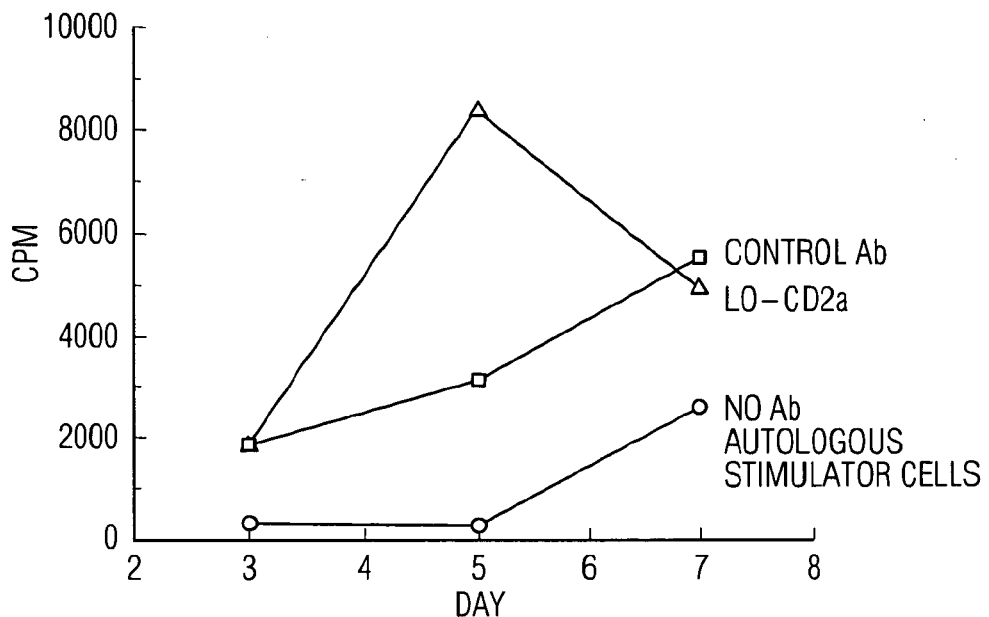

FIGS. 38A and 38B

Response of T-cells cultured with LO-CD2a in a primary MLR to an antigen in a secondary MLR or to tetanus toxoid in secondary cultures.

FIG. 39

Effect of F(ab')$_2$ fragment of LO-CD2a on an MLR.

FIG. 40

Comparison of inhibitory properties of intact LO-CD2a antibody with the F(ab')$_2$ fragment of LO-CD2a on the proliferation of PBMC by soluble OKT3.

FIG. 41

Effect of APCs on inhibitory properties of LO-CD2a on proliferation induced by plate bound OKT3.

DETAILED DESCRIPTION OF THE INVENTION

In accordance with an aspect of the present invention, there is provided a molecule (preferably a monoclonal antibody or fragment thereof) which binds to the same epitope (or a portion thereof) on human lymphocytes as the monoclonal antibody produced by the cell line deposited as ATCC Deposit No. HB 11423. The antibody which is produced by the deposited cell line is hereinafter sometimes referred to as LO-CD2a. The term "molecule" or "antibody that binds to the same epitope as LO-CD2a" includes LO-CD2a. The term "LO-CD2a" includes the antibody produced by the deposited cell line ATCC HB 11423 and those identical thereto which may be produced, for example, by recombinant technology.

The molecules or antibodies of the present invention inhibit human T-cell activation and proliferation and Applicant has found that such inhibition can be effected when adding the molecule or antibody either before or after an agent which stimulates T-cell activation.

The molecules or antibodies of the present invention have the characteristics of binding to an epitope of a CD2 antigen (CD2 positive human T-cells) but it is to be understood, however, that the ability of such molecules or antibodies to inhibit T-cell activation or proliferation may or may not be effected through binding to CD2 positive cells, although Applicant presently believes that the mechanism of action involves binding of the molecule or antibody to CD2 positive cells.

In accordance with another aspect of the present invention there is provided a method of preventing and/or inhibiting on-going immune response in human patients through the administration to the patient of an antibody, hereinafter referred to as LO-CD2a (or fragment or derivative thereof) or any molecule that mimics such antibody or derivative or fragment thereof.

A cell line which produces LO-CD2a, was deposited on Jul. 28, 1993, at the American Type Culture Collection, 10801 University Boulevard, Manassas, Va. 20110-2209, and was given the ATCC accession number ATCC HB11423. Such antibody is a rat monoclonal antibody. Because the strain referred to is being maintained under the terms of the Budapest Treaty, it will be made available to a patent office signatory to the Budapest Treaty.

Although Applicants do not want to limit the invention to any theoretical reasoning, it is believed that the mechanism which enables the monoclonal antibody of this invention to prevent or reduce the severity of an immune response, and to inhibit the activation and proliferation of T-cells, is the fact that the LO-CD2a antibody either decreases the density of CD2 expressed on T cell surfaces and thus decreases the number of CD2$^+$ T lymphocytes; and/or affects signal transduction. It is believed that these mechanisms of action are responsible for not only the prevention of immune response, but also the reduction in severity of on-going immune responses. In addition, the LO-CD2a antibody inhibits natural killer (NK) cell activity in vitro as exemplified herein. This is pertinent to the present invention since it is believed that a non-MHC restricted cytotoxic mechanism such as NK cell activity has been implicated in graft versus host disease.

In accordance with an aspect of the present invention there is provided a process for inhibiting initial or further activation and proliferation of T cells in a human patient by administering to the patient an effective amount of a molecule (preferably an antibody) which binds to the same epitope (or any part thereof) on human lymphocytes as the LO-CD2a antibody. The preferred molecule is LO-CD2a or a chimeric and/or humanized form thereof. Such a molecule would, for example, contain the same complementarity determining region (CDR) as the LO-CD2a antibody.

The term "inhibit" as used herein throughout this Applicant is intended to mean prevention, or inhibition, or reduction in severity, or induction of tolerance to, or reversal of graft rejection. The term "graft" as used herein for purposes of this application shall mean any and all transplantation, including but not limited to, allograft and xenograft transplantation. Such transplantation may by way of example include, but not be limited to, transplantation of cells, bone marrow, tissue, solid-organ, bone, etc.

The term "immune response(s)" as used herein is intended to mean immune responses dependent upon T cell activation and proliferation which includes both cellular effects and T cell dependent antibodies which may be elicited in response to, by way of example and not limitation: (i) grafts, (ii) graft versus host disease, and (iii) autoantigens resulting in autoimmune diseases, which by way of example include but are not limited to rheumatoid arthritis, systemic lupus, multiple sclerosis, diabetes mellitus, etc.

The molecule employed in the present invention is one which binds to the same epitope (or a part of that epitope) as the LO-CD2a monoclonal antibody. The term "binds to the same epitope as LO-CD2a monoclonal antibody" is intended to describe not only the LO-CD2a monoclonal antibody but also describes other antibodies, fragments or derivatives thereof or molecules which bind to the same such epitope as the LO-CD2a monoclonal antibody.

Such other antibodies include by way of example and not limitation rat, murine, porcine, bovine, human, chimeric, humanized antibodies, or fragments or derivatives thereof.

The term "derivative" as used herein means a chimeric or humanized antibody, single chain antibody, bispecific antibody or other such antibody which binds to the same epitope (or a portion thereof) as recognized by the LO-CD2a monoclonal antibody.

The term "fragment" as used herein means a portion of an antibody, by way of example such portions of antibodies shall include but not be limited to CDR, Fab, or such other portions, which bind to the same epitope or any portion thereof as recognized by LO-CD2a.

The term "antibody" as used herein includes polyclonal, monoclonal antibodies as well as antibody fragments, derivatives as well as antibodies prepared by recombinant techniques, such as chimeric or humanized antibodies, single chain or bispecific antibodies which bind to the same epitope or a portion thereof as recognized by the monoclonal antibody LO-CD2a. The term "molecules" includes by way of example and not limitation, peptides, oligonucleotides or other such compounds derived from any source which mimic the antibody or binds to the same epitope or a portion thereof as the antibody fragment or derivative thereof.

Another embodiment of the present invention provides for a method of treating a patient who is to receive or has received a graft transplant with an effective amount of at least one member selected from the group consisting of LO-CD2a antibody, or an antibody, or derivative or fragment thereof or molecules which bind to the same epitope (or a portion thereof) as the LO-CD2a antibody. The treatment is preferably effected with the whole or intact LO-CD2a antibody.

A monoclonal antibody of this invention as hereinabove described may be produced by techniques known in the art such as described by Kohler and Milstein (Nature 256, Pg. 495-497, 1975) as well as the techniques disclosed herein. The preparation of a monoclonal LO-CD2a antibody is described in more detail in Example 1 of this Application. As hereinabove indicated LO-CD2a antibodies may also be produced by recombinant techniques using procedures known in the art. The recombinant antibody may also be in the form of a chimeric antibody wherein the variable regions of a LO-CD2a rat antibody are combined with the constant region of an antibody of another species. Thus, for example, the monoclonal antibody may be humanized by combining the CDR regions of a rat LO-CD2a monoclonal antibody with the V region frameworks and constant regions of a human antibody to provide a chimeric human-rat monoclonal antibody.

In one embodiment, the antibody is a humanized form of LO-CD2a antibody constructed from the constant regions of a human antibody, and the framework and CDR regions of the light and heavy chain variable regions, in which the framework regions of the light and heavy chain variable regions are derived from the framework regions of the light and heavy chain variable region of a human antibody, and the CDR's are the rat LO-CD2a CDR's. In one embodiment, one or more amino acid residues of the framework regions of the light and heavy chain variable regions may be amino acid residues from the rat LO-CD2a framework regions. Such residues from the rat framework regions are retained in the humanized antibody because such residues may maintain the binding specificity of LO-CD2a. Thus, in producing a humanized antibody, in accordance with a preferred aspect of the invention, the CDR's of a human antibody are replaced with the CDR's of LO-CD2a with the added factor that certain amino acids of the light chain variable portion of LO-CD2a in particular from FR1, FR2 and FR3 and certain amino acids of the heavy chain variable portion of LO-CD2a in particular from FR-2 and FR-3 are retained in constructing the humanized antibody; i.e., the corresponding amino acids of the human framework are replaced with the noted amino acids from the rat LO-CD2a framework. As noted with respect to FIG. 31 amino acids 9, 12, 41, 42, 50, 51 and 82 in the framework of the light chain variable region of rat LO-CD2a are retained and as noted in FIG. 33, amino acids 47, 67, 70, 72, 76, 85 and 87 in the framework of the heavy chain variable region of rat LO-CD2a are retained in a humanized antibody. A specific embodiment of the construction of such a humanized antibody is given in Example 7 hereinbelow.

In another embodiment, the present invention is related to a chimeric antibody comprised of a human constant region and the variable regions from rat LO-CD2a and to the use thereof.

The antibody or molecule of this invention preferably: (i) binds to all T lymphocytes and also to null cells but not B lymphocytes as shown by two color staining of lymphocytes analyzed by flow cytometry (FIGS. 26 and 27); (ii) binds to all T cells (as determined by staining with the anti-CD3 antibody Leu4), all CD4 and CD8 positive cells as defined by Leu3a and Leu2b antibodies respectively and some lymphocytes which are CD3 negative (null cells); (iv) binds to null cells as corroborated by the staining of CD16 positive cells as detected with Leu11, a marker for NK cells. (FIG. 26); Staining of B cells, as defined by anti-CD19 binding, was not seen with LO-CD2a. (FIG. 27). LO-CD2a antibody also preferably has the characteristic that the antibody binds to human null cells, and by double staining has a higher intensity of staining to human cells that are both CD2+ and CD4+ than to human cells that are both CD2+ and CD16+, and has a higher intensity of staining of human cells that are both CD2+ and CD8+ than to human cells that are both CD2+ and CD16+.

That Lo-CD2a binds to CD2 was confirmed by transiently expressing CD2 in COS cells.

COS cells were transiently transfected with the δH3MCD2 plasmid containing the gene encoding for the entire CD2 molecule, as described in Peterson A. and Seed B., Nature Volume 329, Oct. 29, 1987, pp 842-846.

Transfection was accomplished by the DEAE-dextran method. Cells were harvested and stained with the anti-CD2 monoclonal antibody Leu5b (Becton-Dickinson) and LO-CD2a, with murine W632 an antibody to MHC class I as a positive control for staining and with the corresponding isotype-matched controls. Specificity of the reactivity was confirmed by assessing binding of the same panel of monoclonal antibodies on COS cells transfected with an irrelevant plasmid.

The staining pattern of these monoclonal antibodies on transiently expressed native CD2 (FIG. 28) indicates that transfection with CD2 led to binding of both antibodies, supporting the ability of LO-CD2a to bind to CD2.

The preparation of LO-CD2a monoclonal antibody suitable for the purposes of the present invention should be apparent to those skilled in the art from the teachings herein.

An antibody or fragment or derivative thereof or molecule of the type hereinabove described may be administered in vivo in accordance with the present invention to inhibit the activation and proliferation of T-cells, and decrease the density of CD2 expression on the cell surface and thereby reduce the number of $CD2^+$ T lymphocytes.

Thus, for example, in an in vivo procedure, such LO-CD2a antibodies are administered to prevent and/or inhibit immune response and thereby inhibit T cell activation and proliferation.

An antibody or fragment or derivative thereof or molecule of the type herein above described may be administered ex vivo in accordance with the present invention to decrease the density of $CD2^+$ expression on the cell surface and thus reduce the number of $CD2^+$ cells of the donor cells. By way of example and not limitation, in an ex vivo procedure, such antibodies or fragments or derivatives thereof or molecules would be infused into donor bone marrow prior to transplantation to prevent the onset of graft versus host disease upon transplantation.

In such an in vivo or ex vivo technique, the antibody or fragment or derivative thereof or molecule will be administered in a pharmaceutically acceptable carrier. As representative examples of such carriers, there may be mentioned normal saline solution, buffers, etc. Such pharmaceutical carriers are well known in the art and the selection of a suitable carrier is deemed to be within the scope of those skilled in the art from the teachings contained herein.

The LO-CD2a antibody or other molecule of the present invention may be administered in vivo intravenously or by intramuscular administration, etc.

As herein above indicated, LO-CD2a antibody or other molecule of the present invention is administered in vivo in an amount effective to inhibit graft rejection. The term "an effective amount" for purposes of this Application shall mean that amount of monoclonal antibody capable of producing the desired effect, i.e., the inhibition of graft rejection or inhibition of the activation of T-cells. In general, such antibody is administered in an amount of at least 1 mg. It is to be understood that lower amounts could be used. In addition after the initial treatment, the herein above described amounts may be reduced for subsequent treatments, if any. Thus the scope of the invention is not limited by such amounts.

In accordance with the present embodiment, such antibodies are administered in order to maintain the inhibition of T-cell activation and graft rejection. Thus, by way of example and not limitation, the antibody may be administered by intravenous infusion over a one to two hour period in amount of from about 1 mg/dose to about 50 mg/dose in a physiologically acceptable carrier suspension once or twice a day for a period of from about eight days or more, as needed. Such treatment for graft rejection is preferably started at, or immediately prior to, or shortly after transplantation or when graft rejection occurs. The treatment could be given once or twice a day for as little as one or two days when started at the time of transplantation to induce a selective hyporesponsive state to the transplant. Such treatment for autoimmune diseases with respect to the administration of the antibody or fragment or derivative thereof or molecule in accordance with the present invention is begun when the attending physician has determined it is desirable to inhibit a pathological immune response.

Thus, in accordance with an aspect of the present invention, by administering an antibody in accordance with the invention at the time of transplantation and in most cases for a short period thereafter there can be induced a hyporesponsiveness to the transplanted tissue or organ, thereby to prevent or inhibit further episodes of rejection.

The techniques of the present invention for inhibiting the activation of T-cells may be employed alone or in combination with other techniques, drugs or compounds for inhibiting the activation of T-cells or inhibiting graft rejection or graft versus host disease.

The invention will be further described with respect to the following examples, which are illustrative and which are not intended to limit the scope of the invention.

The cells, cultures, mAbs and mitogens used in the examples may be prepared and used by processes and procedures known and practiced in by those of ordinary skill in the art. The following is an example of a process or procedure that may be used for the preparation and use of the cells, cultures, mAbs and mitogens used in the examples which follow.

Cells and Cultures

PBMC were obtained by Ficoll-Hypaque (Pharmacia, Sweden) sedimentation of heparinized blood obtained from the local Blood Donor Center. Isolated PBMC were resuspended in enriched medium: RPMI 1640 medium (Gibco, Belgium), supplemented with 100 U/ml penicillin, 100 ìg/ml streptomycin, 20 mM L-Glutamine, and 20% pooled human AB serum or 15% heat-inactivated fetal calf serum. PBMC were cultured at $1 \times 10^5$ cells/well in 96 U-well micro plates (Falcon) in a final volume of 200 ìl of culture medium/well. Bidirectional MLC were performed with $1 \times 10^5$ cells of each donor/well in the same volume of culture medium as noted above. All cultures were made in triplicate. Eight hours before the times indicated in the results, cultures were pulse-labelled with 2.0 ìCi/well of $3_H$-T (Amersham, Belgium; 247.9 GBq/mmol; 6.7 Ci/mmol) and the radioisotope incorporated in cultures was quantified by liquid scintillation in a Beta-counter (Beckman L5 6000 SE). The percentage of inhibition was calculated as follows: % Inhibition=[1−(mean cpm of tested culture/mean cpm control culture)]×100. All results are expressed as the mean of three independent cultures. Standard deviation was always less than 15% of the mean, except for those cases where these values are indicated on the graphics.

Cytofluorometric analyses were performed using a FACScan cytofluorograf (Becton Dickinson) with Hewlett-Packard hardware equipped with the CONSORT 30 program. Independent analysis of staining of lymphocytes and blast-cells was possible using differential gating as defined by size and granularity. 25,000 events were analyzed for each sample. In these experiments, LO-CD2a final concentration was 200 ng/ml, except when indicated.

Mabs and Mitogen

LO-DRA and LO-Tact-1 (both FITC-labelled), are rat mAbs produced in our laboratory (op. cit. H. Bazin (Ed) 1990 p. 287). LO-Tact-1 is directed against the p55 chain of the IL-2 receptor (op. cit. H. Bazin Immunol. 1984 and Janszen, M., Buck, D. and Maino, V. C. in Leucocyte Typing IV White Cell Differentiation Antigens, W. Knapp (ED), Oxford University Press, 1989, p. 403). Mouse anti-human-CD2 and anti-CD3 mAbs (Leu-5b and Leu-4a-FITC-labelled) were obtained from Becton Dickinson (Belgium). Mouse anti-human-CD4 or anti-human-CD8 mAbs (phcoerythrine-labelled), and mouse IgG FITC- or phcoerythrine-labelled (negative controls) were obtained from Coulter. OKT3 (Ortho-Cilag, Belgium) was used at a final concentration of 100 ng/ml. Phytohemagglutinin A (PHA; Wellcome Labs, UK) and Concanavalin A (Con A; Calbiochem Co., USA) were used at a final concentration of 1 and 10 ìg/ml, respectively.

Biotinylation of LO-CD2a. The concentration of purified LO-CD2a was adjusted to 1 mg/ml in 0.1M sodium bicarbonate buffer, pH 8.4. NHS-biotin (Boehringer Mannheim 1008 960) was dissolved in DMSO at a concentration of 1.5 mg/ml. For each MAB, 0.1 ml of NHS-biotin solution was added. The mixture was rotated for 2 hrs. at ambient temperature. The reaction was completed by adding 0.1 ml of 2M Tris-HCl, pH 8.0, for each ml of antibody (10 minutes at ambient temperature), followed by 1 ml of 1% BSA in phosphate buffered saline (PBS) for each ml of antibody. To remove free biotin, the solution was dialyzed overnight at 4° C. in 1000 volumes PBS. Both the biotinylation reaction and the conjugated mAb were shielded from light by covering with aluminum foil.

Lysis of red blood cells (RBC). RBC were removed from whole blood by lysis with ammonium chloride. A 10× stock solution was prepared which consisted of 90 g $NH_4Cl$, 10 g $KHCO_3$, 370 mg EDTA, and $H_2O$ to a volume of 100 mls. Forty mls of 1× ammonium chloride was added to each 10 mls of blood and incubated for 10 min. at room temperature. The mixture was then centrifuged at 1200 rpm for 10 min and the pellet resuspended in 10 ml PBS with 0.1% azide.

Staining of peripheral blood. Staining was carried out in round-bottom 96 well cluster plates (Costar #3790) at 4° C. For single color staining, ten ìl of mAb was appropriately diluted in PBS containing 0.2 mg human immunoglobulin and added to each well. Red blood cell depleted blood was distributed into plates at a volume of 90 ìl per well. Cells and mAb were mixed by gentle tapping and incubated 30 min. Fifty ìl of cold PBS was added to each well and plates were centrifuged at 1900 rpms for 2 min. Supernatant was discarded by inversion and gentle flicking of the plate. Cells were dispersed by tapping the plate on the counter. The wash procedure was repeated twice by adding 200 ìl of cold PBS. Ten ìl of a 1/20 dilution of goat F(ab')$_2$ anti-rat 1 g-FITC was added to the dispersed cells in each well and incubated for 30 min. in the dark. Cells were washed by the addition of 180 ìl of cold PBS to each well followed by centrifugation at 1900 rpms for 2 min. Supernatant was discarded, cells dispersed, and 200 ìl of cold 0.5% paraformaldehyde was added to each well. Cells were transferred to tubes (Falcon #2054) and diluted to approximately 0.5 mls with 0.5% paraformaldehyde. Samples were evaluated on a Becton-Dickinson FAC-Scan machine using LYSIS II software.

Dual color staining was carried out by a similar protocol. After cells were incubated with the primary mAb and the FITC-conjugated anti-rat reagent, a 1/5 dilution of normal mouse serum was added to block any remaining sites on the anti-rat reagent. Following a 15 min. incubation (no wash), 20 ìl of a PE-labeled mAb specific for a known CD determinant was added and incubated for 30 min. Cells were washed and fixed as described for single staining.

EXAMPLE 1

Figure 2A:
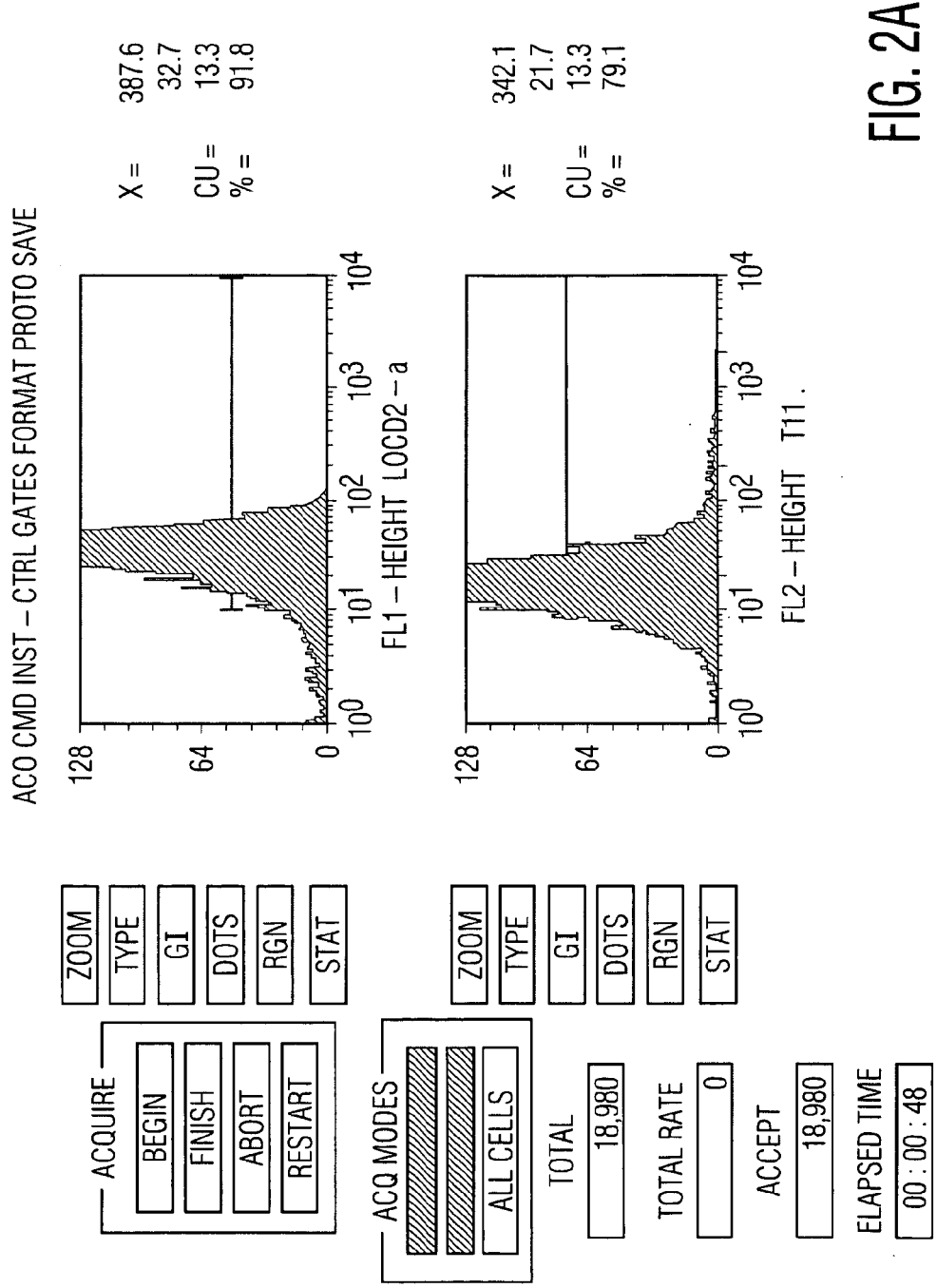
Figure 2B:
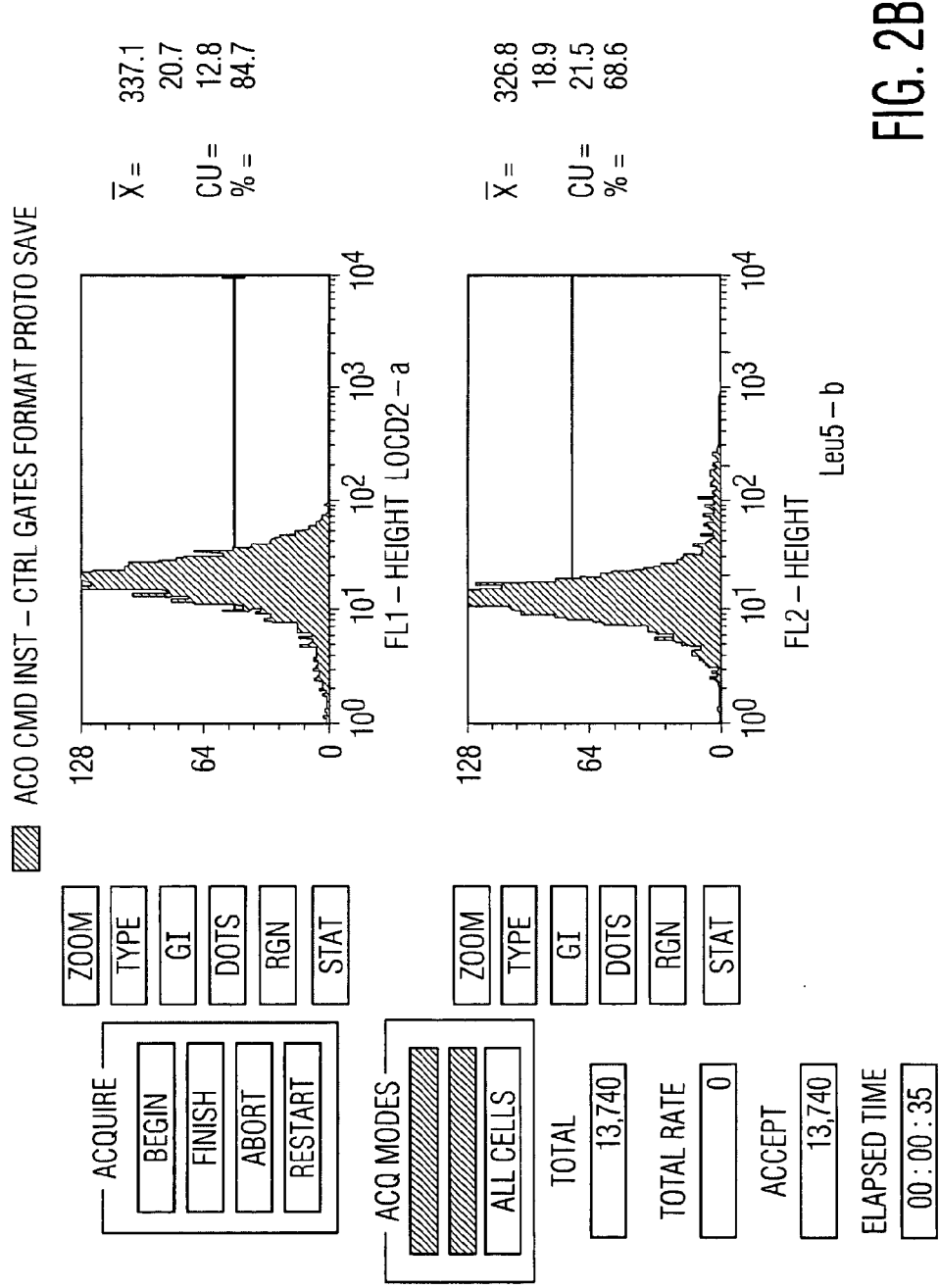

LO-CD2a is a rat (IgG2b-Kappa) anti-CD2 monoclonal antibody produced and characterized in our laboratory as indicated elsewhere (See the following references: Xia, H., Ravoet, A. M., Latinne, D., Ninanne, J., De Bruyere, M., Sokal, G. and Bazin, H., in H. Bazin (Ed), *Rat Hybridomas and Rat Monoclonal Antibodies*, CRC Press, Inc., Boca Raton, Fla. 1990, p. 309 and Ravoet, A. M., Latinne, D., Seghers, J., Manouvriez, P., Ninanne, J., DeBruyere, M., Bazin, H. and Sokal, G.—in H. Bazin (Ed) *Rat Hybridomas and Rat Monoclonal Antibodies*, CRC Press Inc., Boca Raton, Fla., 1990, p. 287). LO-CD2a was purified from ascitic fluid by immunoaffinity chromatography taking advantage of the allotypic difference existing between the immunoglobulins of the rat receiving the producing hybridoma and the mAb secreted by the latter (Bazin, H., Cormont F. and DeClercq, L. *J. Immunol. Method.*, 1984, 71:9). It recognizes the total population stained by the mouse mAb Leu-5b (FITC-labelled) FIG. 1 and roughly 90% of the population marked by the mouse T11 (Rhodamine-labeled) mAb ((data not shown). The epitope recognized by LO-CD2a on the CD2 molecule, is different from the epitopes recognized by the anti-CD2 mouse mAbs Leu-5b and T11 (FIG. 2).

EXAMPLE 2

LO-CD2a Exhibits Modulatory but not Mitogenic Effects on PBMC

In order to determine the effects of the rat mAb LO-CD2a on resting lymphocytes, PBMC were incubated in the presence of increasing concentrations of this mAb.

TABLE 1

EFFECT OF LO-CD2a ON PBMC

| Culture | $^3$H-thymidine incorporation-cpm (mean ± S.D. | | | |
|---|---|---|---|---|
| Medium | Donor 1 | Donor 2 | Donor 3 | Donor 4 |
| RPMI alone +LO-CD2-a | 215 ± 7 | 203 ± 3 | 1195 ± 27 | 1114 ± 204 |
| 2.500 µg/ml | 207 ± 18 | 106 ± 2 | | |
| 1.250 µg/ml | 265 ± 29 | 89 ± 21 | | |
| 0.750 µg/ml | 360 ± 3 | 147 ± 5 | | |
| 0.375 µg/ml | 415 ± 63 | 135 ± 2 | | |
| 0.250 µg/ml | | | 747 ± 63 | 1143 ± 393 |
| 0.125 µg/ml | | | 967 ± 137 | 2332 ± 249 |
| 0.075 µg/ml | | | 1164 ± 61 | 1058 ± 182 |
| 0.037 µg/ml | | | 1197 ± 75 | 1131 ± 93 |

As can be seen in Table 1, PBMC incubated for 6 days in the presence of LO-CD2a show no significant variations in the rate of $^3$H-T incorporation as compared with control cultures. Cell viability at the end of this period was variable but averaged around 80% as assessed by trypan blue exclusion. When resting PBMC were incubated in the presence of LO-CD2a, there was no significant variation in the phenotypic expression of several membrane markers, as assessed by flow cytometry. Cellular markers of resting mature T-cells (such as CD3, CD4 and CD8) show the same pattern of variation during 6 days of culture in the presence or in the absence of LO-CD2a, and activation molecules such as CD25 (IL-2R/p55) are not expressed in these experimental conditions or are not modified by LO-CD2a as is the case of DR antigenic determinants. (FIG. 3)

Figure 4:
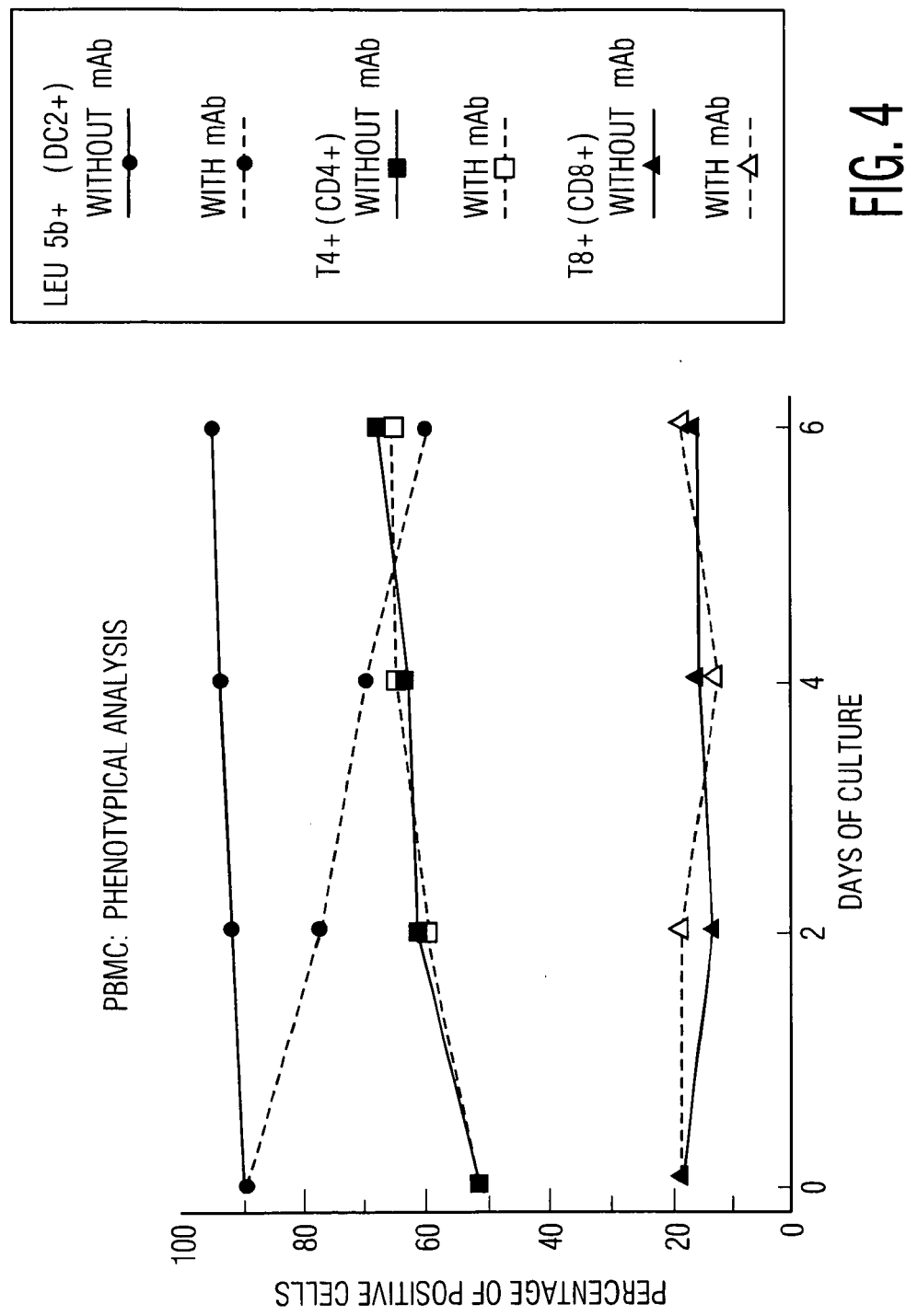

When PBMC were incubated for 6 days in the presence of LO-CD2a, a significant decrease was observed in the percentage of Leu-5b+ gated lymphocytes. (FIG. 4) The percentage of CD4– and CD8– lymphocytes is not affected during a 6-day period of cultures by the presence of LO-CD2a, indicating that the observed decrease of CD2–bearing lymphocytes cannot be attributed to an elimination of these cells but rather to a disappearance of the CD2 molecule or to a conformational change in this glycoprotein produced by the binding of LO-CD2a.

In order to verify if the observed decrease in Leu-5b– lymphocytes was due to a conformational change of CD2 or to a disappearance (internalization or release) of this molecule after the binding of LO-CD2a, PBMC were cultured in the presence of 500 ng/ml of LO-CD2a and analyzed through 6 days in flow cytometry using Leu-5b (FITC-labelled), T11-RD1 (Rhodamine-labelled) and MARK-3 (FITC-labelled). As shown in FIG. 5a, Leu-5b or T11 mabs are not able to bind to PBMC after 2 to 4 days of culture in the presence of LO-CD2a. Under these conditions, the mouse anti-rat kappa chain mAb MARK-3 labelled 50% of cells at day 6 of culture indicating that only 35% of the original CD2–bearing cells show no LO-CD2a on their surfaces, yet Leu-5b–FITC and T11-RD1 staining have decreased markedly at day 2. This suggests that a conformational alteration of CD2 rendering the epitope of Leu5b and T11 unavailable for binding occurs in response to LO-CD2a.

The analysis of the mean fluorescence of CD2+ cells indicated that the density of expression of this marker decreased with time in the presence of LO-CD2a. The same phenomenon was observed whether Leu-5b FITC-labelled or LO-CD2a (revealed by MARK-1 FITC-labelled) were used to detect the CD2+ lymphocytes. Aliquots of the same PBMC were cultured in parallel in the presence of Leu-5b (commercially available mAb, dialyzed against PBS, 1:2 final dilution in culture medium). As shown in FIG. 5b, in those experimental conditions all the CD2–bearing cells are coated by the Leu-5b mAb (as revealed by goat anti-mouse-FITC). Staining by T11-RD1 was markedly reduced, whereas a smaller, slower decrease was observed in the percentage of cells presenting the epitope recognized by the LO-CD2a-FITC mAb. Taken together these results indicate that CD2 molecules have partially changed their conformation in response to LO-CD2a, and that a slow modulation of CD2/LO-CD2a occurs.

LO-CD2a Inhibits MLR

Figure 6A:
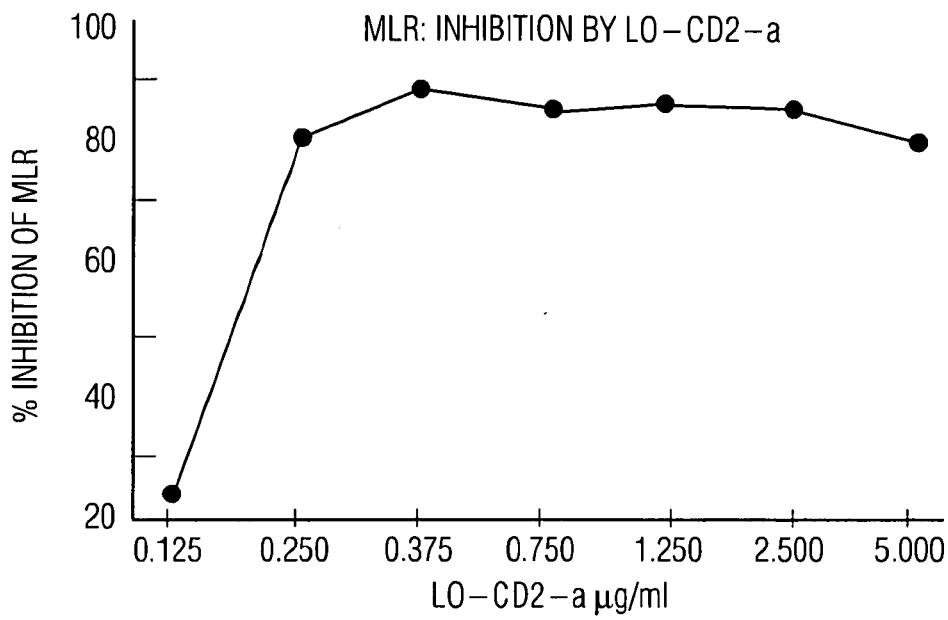
Figure 6B:
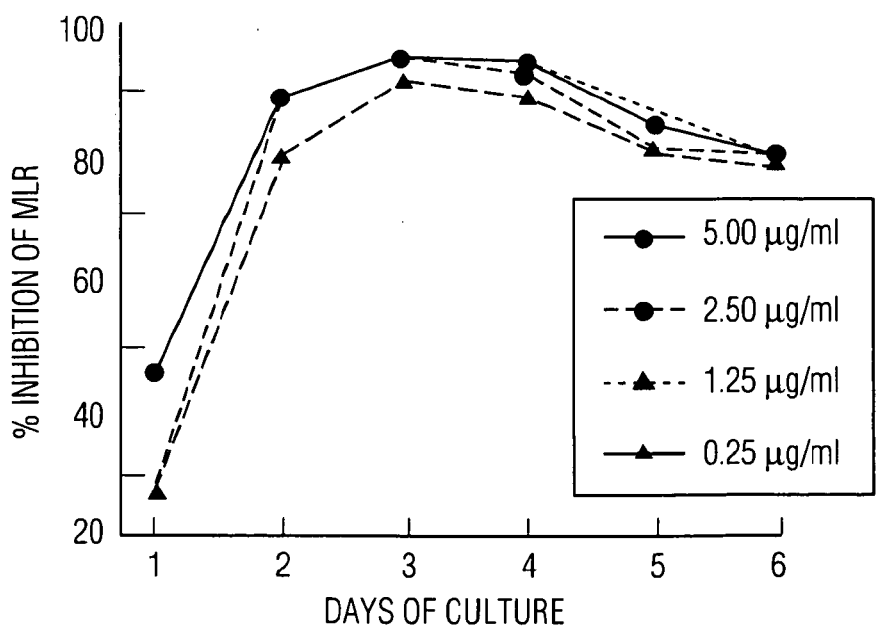
Figure 6C:
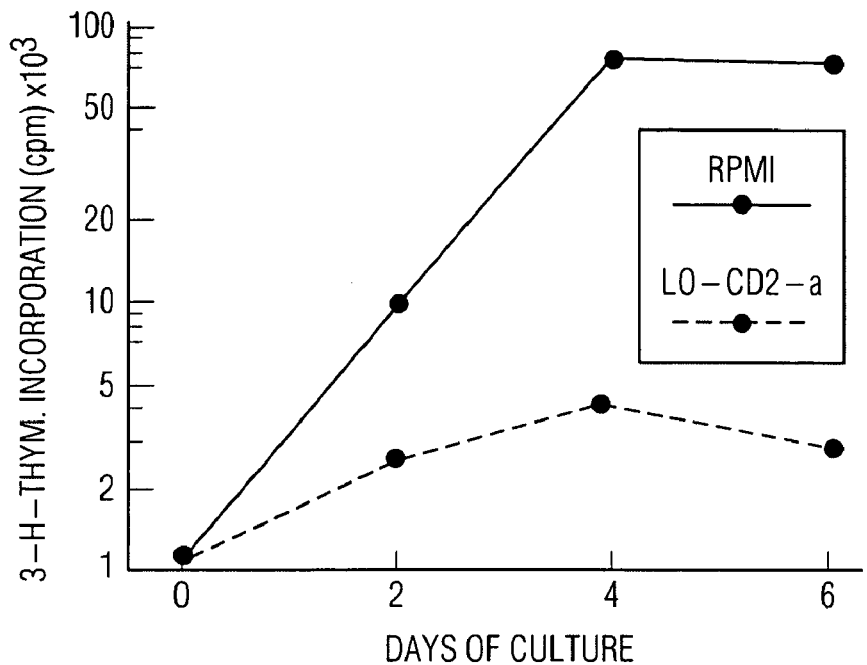

When MLC were performed (over a period of 6 days) in the presence of increasing concentrations of rat mAb, a significant inhibition of the MLR (as measured by $^3$H-Thymidine ($^3$H-T)-incorporation), was observed at concentrations of mAb as low as 125 ng/ml. In FIG. 6a, we show a typical example of a dose-response curve of MLR inhibition by LO-CD2a. As can be seen in this FIG. 6a, LO-CD2a induces 80% inhibition of MLR (6 days of culture) at 250 ng/ml and this percentage of inhibition remains almost constant or higher than 80% over a wide range of concentrations (0.25 to 5.0 ig/ml of mAb). FIG. 6b shows a time-course of the inhibitory effects of different concentrations of LO-CD2a on MLR from day 0 to day 6 of culture. A typical example of $^3$H-T-incorporation on MLC (in the presence or in the absence of LO-CD2a) is shown in FIG. 6c, where LO-CD2a was added at a final concentration of 200 ng/ml.

Figure 6D:
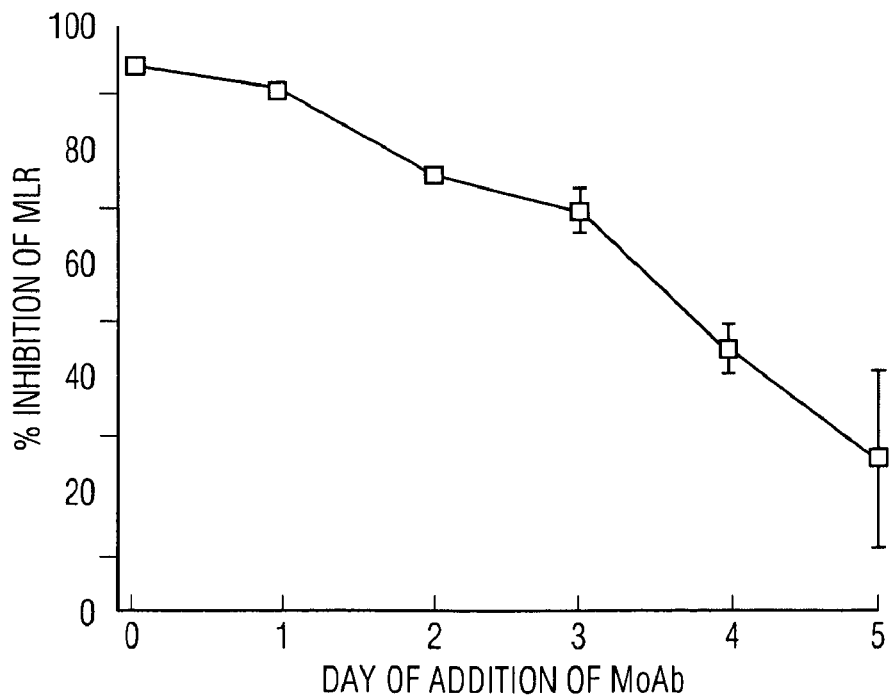

In FIG. 6d we show the effects of LO-CD2a on MLR, when this mAb (at 200 ng/ml) is added at varying times after initiation of MLC. More than 90% inhibition of MLR (as measured by $^3$H-T incorporation) is obtained when this mAb is added at day 0, and this inhibitory effect is still present (45% inhibition in this example) when LO-CD2a is added 4 days after the beginning of MLC. Similar results (not shown) were obtained with higher concentrations (from 0.20 to 5.0 ig/ml) of LO-CD2a.

LO-CD2a Blocks the Pathway of IL-2R Expression

When cytofluorograph analyses were performed on the lymphoblast subset of a MLC (FIGS. 7a and b), the following observations were made: a) the number of blast cells (around 300-500 blast cells of 25,000 events analyzed) already present at initiation of MLC rose sharply from day 4 to day 6 in control cultures (more than 1200 blast cells from 25,000 events analyzed); b) in MLR performed in the presence of LO-CD2a, there was no significant variation in the number of blast cells during the whole period of culture and at day 6 the number of blast cells is always lower or nearly the same as the initial number of blasts at day 0 (FIG. 7a); c) the percentage of CD25 blasts rose sharply among cells incubated without LO-CD2a (FIG. 7b); d) this percentage remains below 20% in the small number of blasts from the MLC incubated in the presence of mAb (FIG. 7b), and the mean fluorescence (as a measure of CD25 expression) decreased by 75% as compared with blasts present in control cultures (results not shown); e) in the absence of mAb the percentage of CD3– blasts remains constant during the first 4 days of culture (FIG. 7b) and on day 6 the percentage of CD3– cells increased to 90%, while in the presence of LO-CD2a the percentage of CD3– rises slowly to reach only about 45% at day 6. These results indicate that the presence of LO-CD2a inhibits the entrance of these cells in the pathway of activation characterized by the expression of IL-2 receptor (CD25). The number of CD2+ blasts remains constant or decreases in the presence of LO-CD2a, and the density of expression of this membrane marker is strongly diminished under these conditions (data not shown).

When phenotypic analyses were performed through 6 days on the resting (non blast) lymphocyte subset of MLC, results similar to those described in FIG. 3 were obtained: in the presence of LO-CD2a, no significant variation could be detected in the percentage of CD3+, CD4+ or CD8+ lymphocytes, as compared with control cultures; no CD25 expression (activation marker) could be detected whether in the presence or in the absence of LO-CD2a during 6 days of culture (FIG. 8a). These results suggest that LO-CD2a has a very weak, if any, effect on the resting subset of T-lymphocytes in MLC; that is to say, in T-cells not committed in the process of activation. At the same time, as shown in FIG. 8b, LO-CD2a induces a significant decrease in the percentage of CD2+ lymphocytes during MLC. These results suggest that in both the unstimulated cultures (FIG. 5) and in the MLC, the effect of LO-CD2a is to reduce the expression of CD2 and/or to induce a conformational change in its structure.

LO-CD2a can block the pathways of T-cell activation dependent on the TcR/CD3 complex or on mitogen receptors.

When LO-CD2a was added to mitogen-activated PBMC, a significant inhibition of $^3$H-T incorporation was observed. In one of three experiments of PBMC incubated with mitogens (OKT3, ConA and PHA) in the presence or in the absence of LO-CD2a added either at time 0 or 1 hour after the start of cultures. In the first case, mitogens were added 1 hour later.

Figure 9:
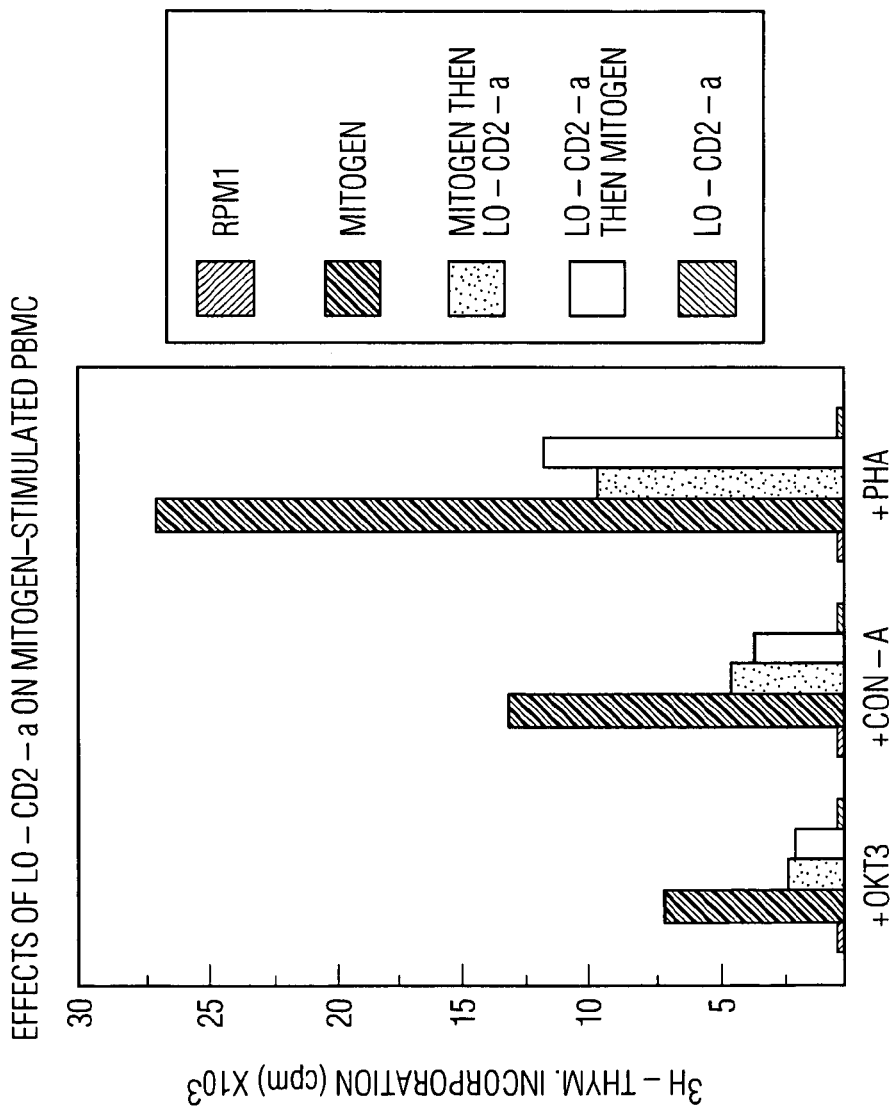

When LO-CD2a was added 1 hour after the initiation of culture, mitogens were added at time 0. This was done in order to know whether, preincubation of PBMC with mitogens or LO-CD2a could trigger events that could be affected by the addition of the second reagent. Cultures were harvested at 96 h, after a pulse-labelling (6 h) with $^3$H-T. More than 50% inhibition of $^3$H-T. incorporation was observed in the presence of LO-CD2a, whether it is added first or after mitogens. (FIG. 9) The same effect was observed when cells were harvested 4 days after the onset of MLC and exposed to mitogens (results not shown). A drastic decrease in $^3$H-T incorporation was observed two days after the onset of MLC, in those cultures receiving both the mitogen and LO-CD2a, as compared with the same cultures receiving only mitogen (results not shown). Preincubation of MLC with LO-CD2a before addition of mitogen, lowered the $^3$H-T-uptake to values comparable with MLC without OKT3.

Figure 10:
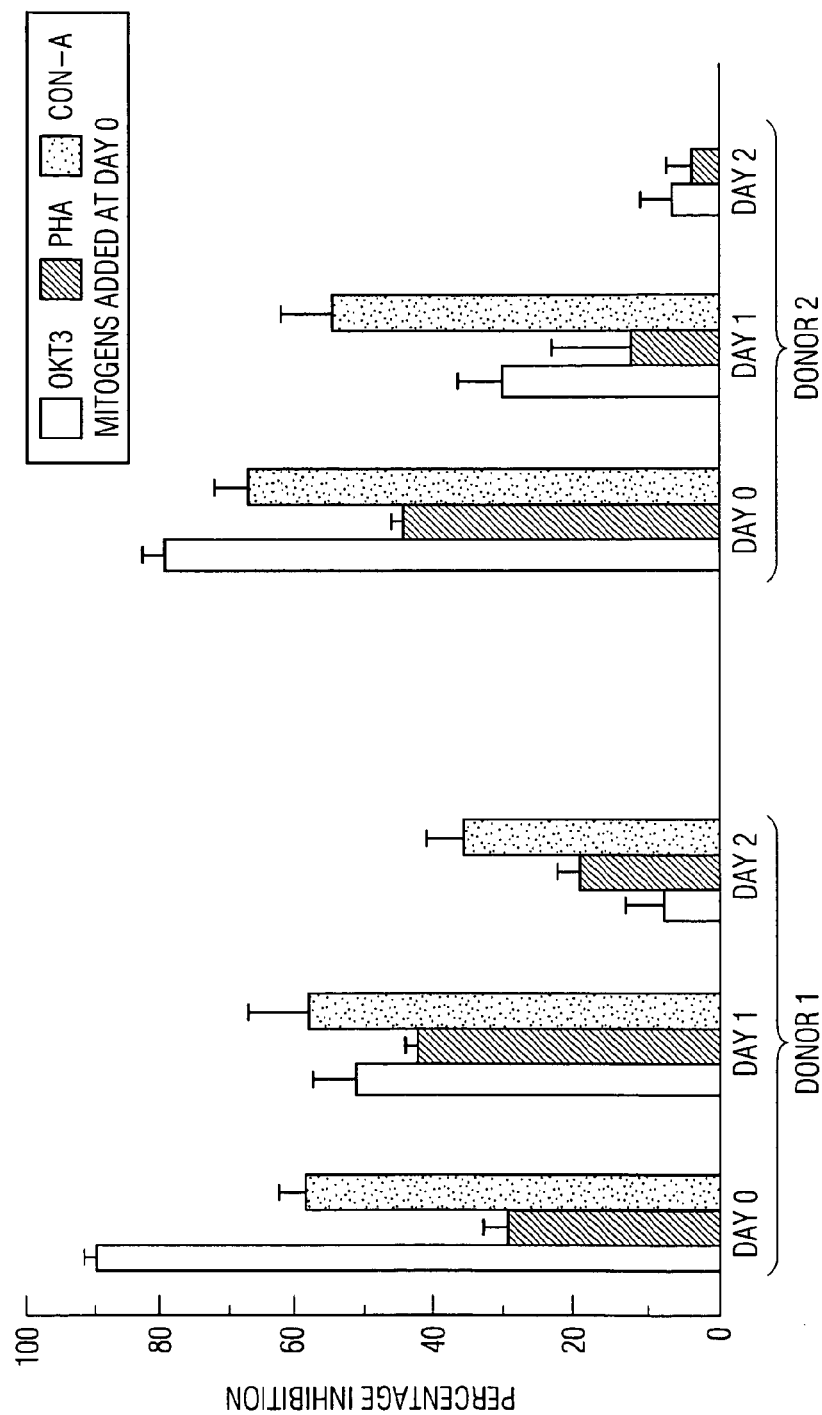

LO-CD2a was also able to inhibit mitogen induced proliferation if added one day after the initiation of mitogen induced proliferation. The results of experiments performed with two donors are shown in FIG. 10. PMBC were incubated along with mitogens (OKT3, ConA and PHA). In these experiments, LO-CD2a was added either at time 0 (Day 0), 24 h (Day 1) or 48 h (Day 2) after the start of the cultures. The inhibition of proliferation in response to OKT3 and ConA by LO-CD2a was significant if added 24 hours after the addition of mitogen at time 0.

EXAMPLE 3

Inhibition of Natural Killer Cell (NK) Activity.

PBMC were isolated from heparinized blood by Ficoll Hypaque Sedimentation. After washing, the effector cells, suspended in enriched medium, were incubated overnight at a concentration of 1×10$^6$/ml in a Falcon plate to eliminate the monocytes (by adherence).

The target cells (K562 cell line) were labeled by overnight incubation with $^{51}$chromium $^{51}$Cr (0.9 ml of a cell suspension at 3×10$^6$/ml+0.02 ml from a solution of 5mCi/ml$^{51}$Cr, Amersham).

After a 16-hour incubation, effector and target cells were washed four times, counted and incubated in a 96 V bottom microplate at different E/T ratios: 200/1 (100 ul of a suspension of 4×10$^6$/ml effector cells with 100 ul of 2×10$^4$/ml target cells) 100/1, 50/1 and 25/1.

After a four-hour incubation, the $^{51}$Cr release was measured by counting 100 ìl supernatant from each well in a gamma counter.

Maximum (target cells+1NHCl) and spontaneous release (target cells+enriched medium) were used to calculate the specific lysis:

---
test- spontaneous release
---

Inclusion of LO-CD2a at 5, 1 and 0.5 ug/ml in the NK assay with two normal donors (FIGS. 10a and 10b) led to an inhibition of cytotoxicity of approximately 50% with all tested concentrations of antibody and over all tested E/T ratios. This is in comparison with essentially complete inhibition of proliferation in the MLR at doses at or above 0.25 ug/ml.

EXAMPLE 4.

IN VIVO STUDIES IN NON-HUMAN PRIMATES

Material and Methods

Monoclonal Antibodies

MARK3-FITC is a mouse mAb directed against the rat Ig kappa 1b allotype conjugated with FITC. MARG2b-biotin is a mouse anti-rat IgG2b immunoglobulin mAb conjugated with biotin. These two mAbs were produced and labeled in our laboratory. For immunofluorescent tests they were used at a final concentration of 2.5 ìg/ml. Leu-5b–FITC (Becton-Dickinson) and T11 Rhodamine (COULTER) are two mouse anti-human CD2 mAbs. T4– and T8– Rhodamine-labeled (COULTER) are mouse anti-human CD4 and CD8 mAbs, respectively.

Phenotype Analysis

Anti-human T-cell mAbs (anti-CD2, -CD4, -CD8, see above) were added to 100 ìl samples of whole blood and incubated at 4° C. for 45 min. Red blood cells were lysed with a Tris-buffered ammonium chloride-lysing buffer (144 mM NH$_4$CL$_1$/17 mM Tris, pH 7.2) and lymphocytes were washed with PBS/2% FCS/0.2% NaN$_3$. For detection of non-labeled mAbs, a second mAb (FITC- or biotin-conjugate) was added to a final concentration of 2.5 ìg/ml. After 45 min. incubation at 4° C., cells were washed with PBS/FCS/NaN3. For biotinylated mAbs, a further incubation (15 min) with Streptavidin-Phycoerythrin conjugate was done. Labeled human or monkey lymphocytes were resuspended in a 2% formalin solution and analyzed in a FACScan cytofluorometer (Becton-Dickinson) equipped with the LYSIS II program for gating lymphocytes as a function of size-vs-granularity. As a control for nonspecific staining, aliquots of cells were incubated with FITC- or Phycoerythrin-conjugated mouse Igs (Coulter).

Level of Circulating Abs

LO-CD2a in serum was quantified by ELISA using a mouse anti-rat IgG2b mAb (MARG2b-8, produced in our laboratory ) as first layer (coating) and a mouse anti-rat kappa chain (MARK-3) mAb coupled to horseradish peroxidase for detection. Briefly, microtiter plates (Falcon) were incubated overnight with 100 ìL/well of MARG2b-8 (5 ìg/ml) and unoccupied sites on plastic were saturated with PBS containing 5% powdered milk (bovine). After 1 h incubation at room temperature, plates were washed with PBS with 0.1% Tween-20, and incubated 1 h with 100 ìl/well of diluted monkey or human serum. After washing out unbound material, plates were incubated 1 h with 100 ìl/well MARK3-peroxidase (2 ìg/ml in PBS). After washing again, plates were incubated with OPD (o-phenylenediamine dihydrochloride, 0.4 mg/ml, Sigma Chemicals), in citrate-phosphate buffer containing 0.03% H$_2$O$_2$. The colored reaction product was detected at 492 nm. A standard curve was made in parallel with a known concentration of purified LO-CD2a serially diluted in a pool of control monkey or human serum.

The detection of monkey or human anti LO-CD2a antibodies was performed by ELISA using 96 well microtiter plates coated with LO-CD2a (5 ìg/ml). Anti-LO-CD2a human or monkey antibodies bound on the plates, were revealed by horse-radish peroxidase labeled rat anti-human IgM (LO-HM-7) or IgG (LO-HG-22) mAbs.

A. Cynomolgus Monkeys

One Cynomolgus monkey received 10 mg/day of LO-CD2a for three consecutive days. The monoclonal antibody was well tolerated.

Lymphocyte depletion was observed after the first injection but a very little additional depletion was obtained after the 2d and 3d injections.

The second monkey received 20 mg/d for 10 days. The mAb was also well tolerated. No side effects were observed after dosing in that the animals were active, alert, eating well with no evidence of nausea or gastrointestinal disturbance.

Figure 12:
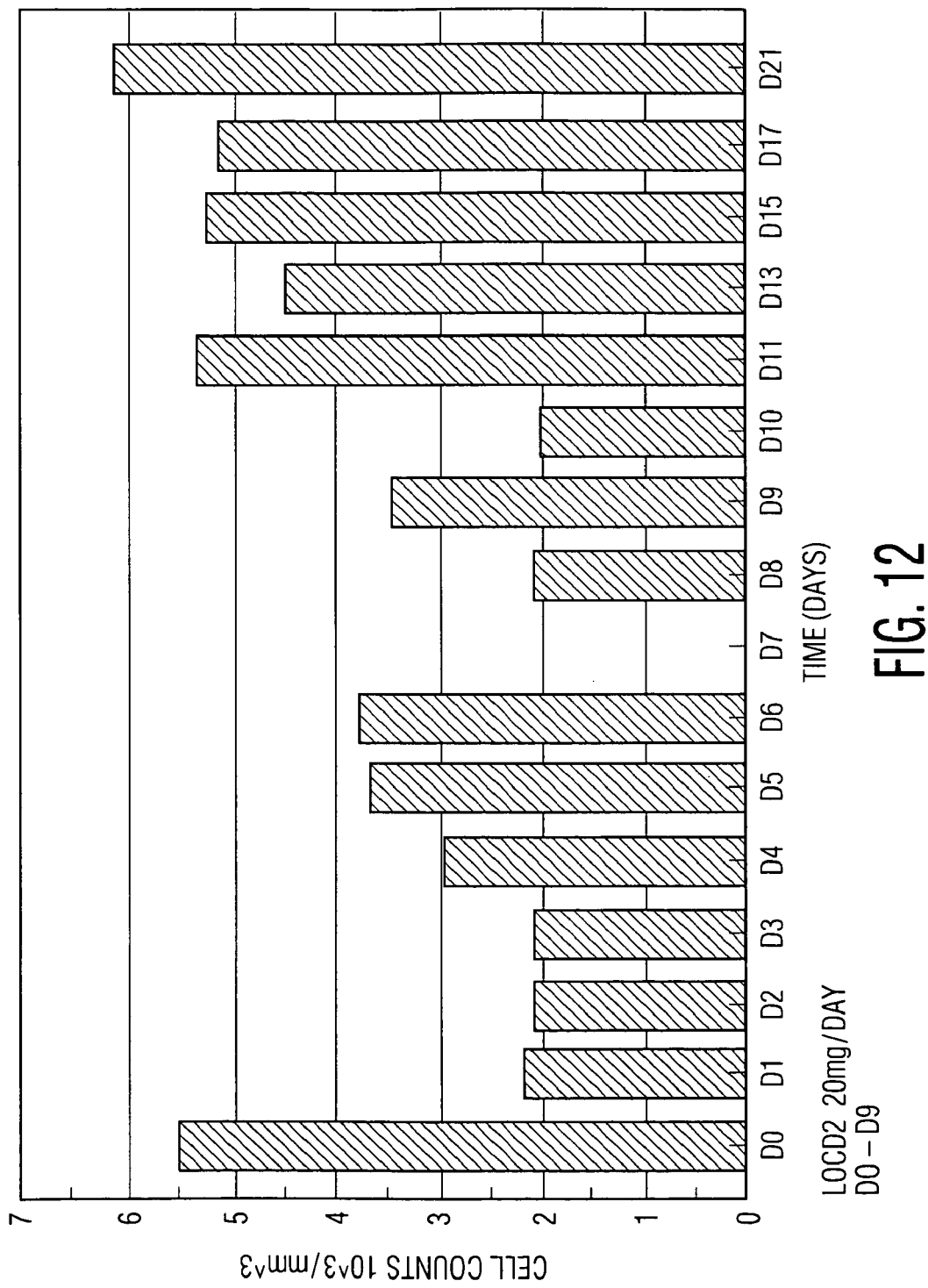
Figure 13:
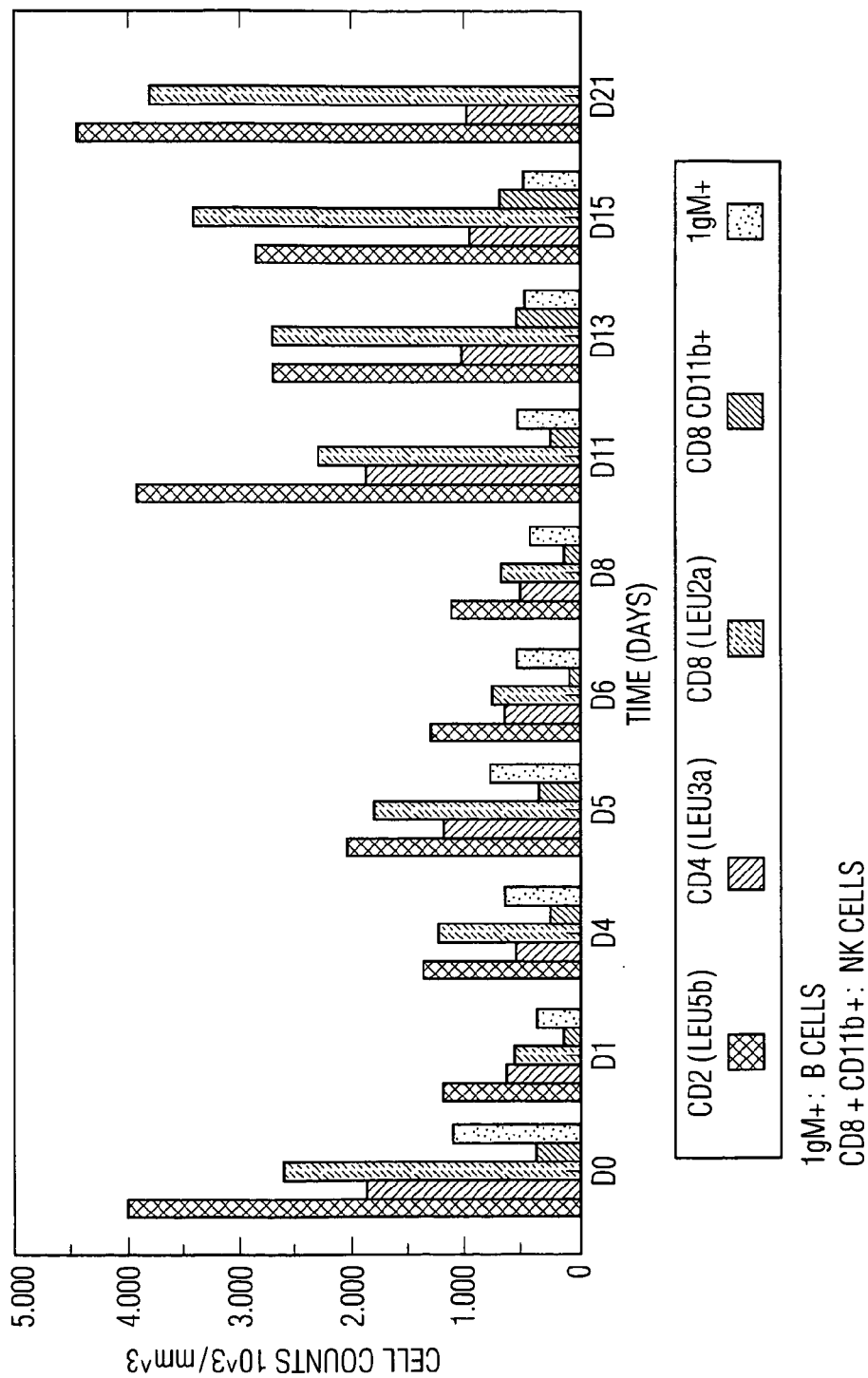
Figure 14:
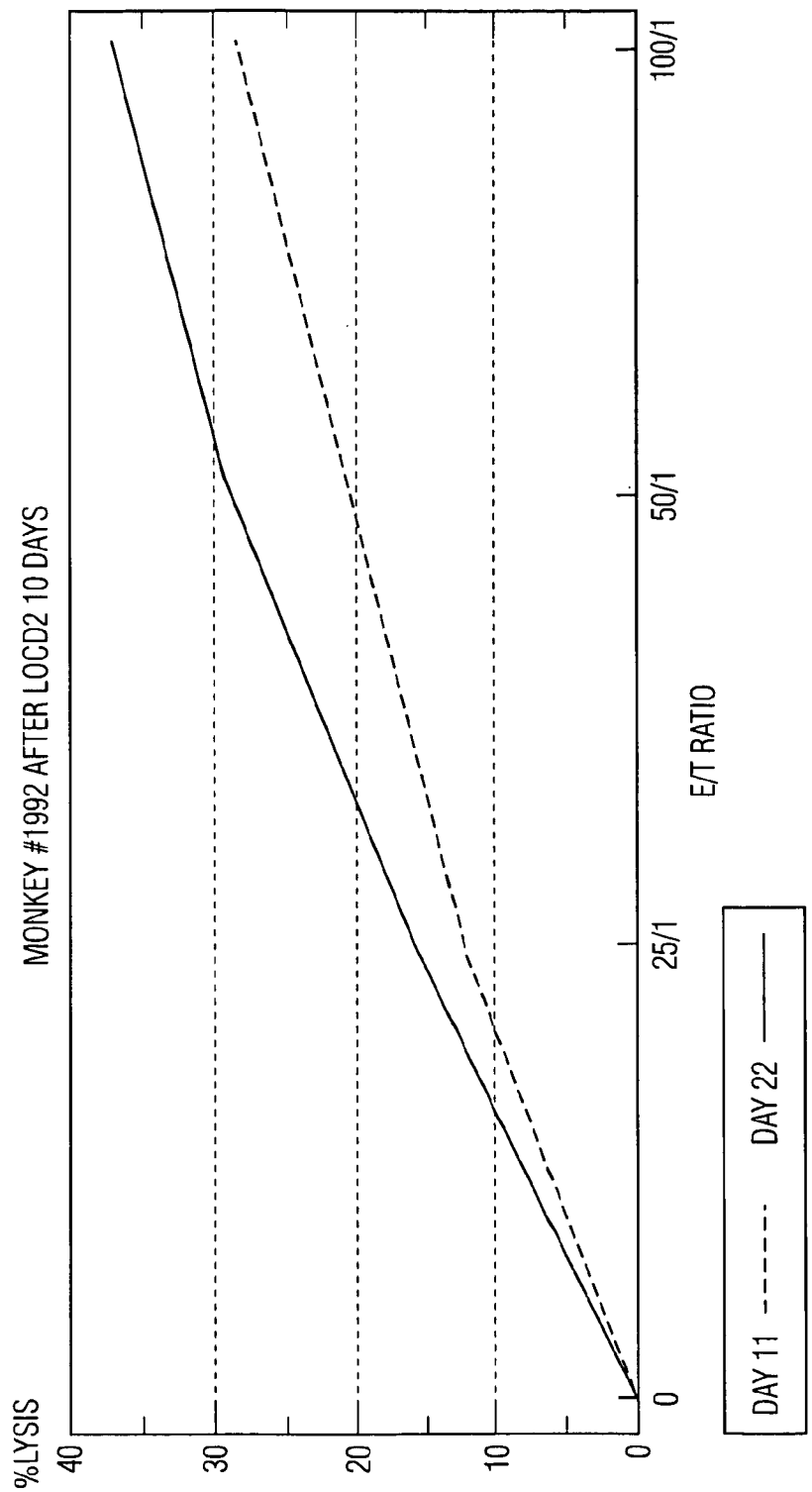
Figure 15:
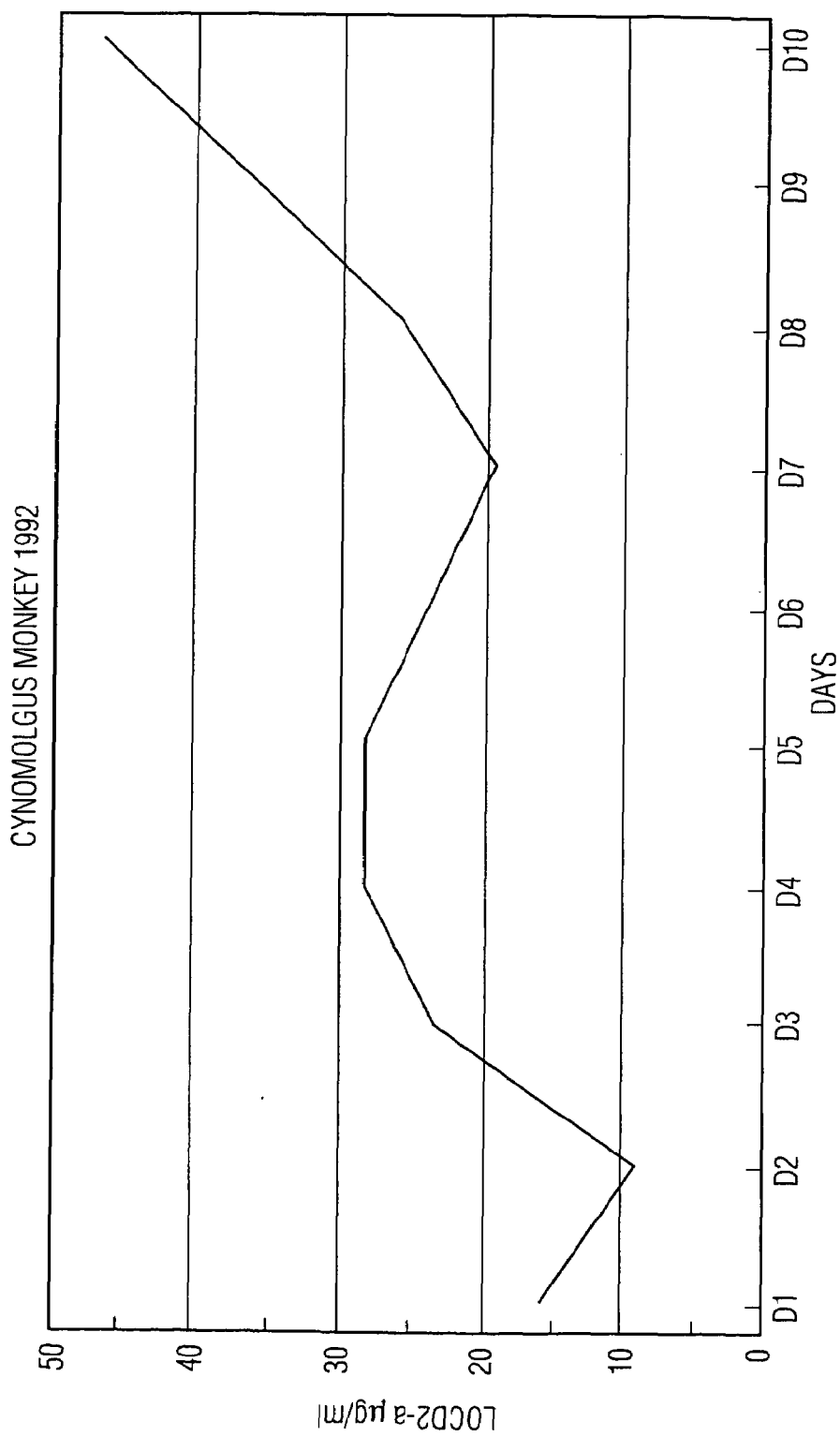
Figure 16:
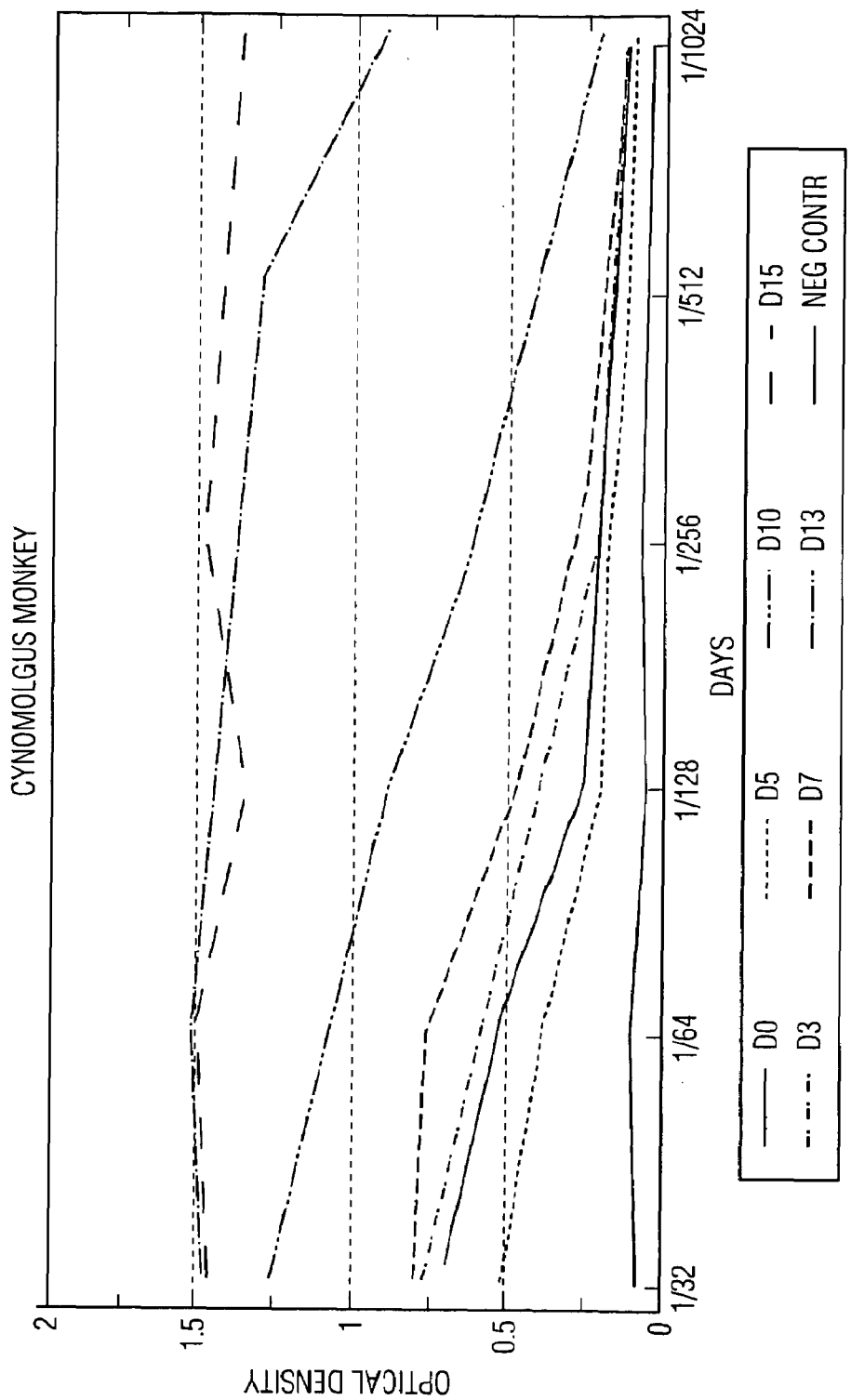

The lymphocyte counts and cell populations in the second monkey are summarized in FIGS. 12 and 13. The NK activity was slightly reduced after the 10 injections (FIG. 14). The circulating levels of MAb were very high (FIG. 15) and immunization occurred at the end of the treatment (FIG. 16).

B. Baboon

The experiment described here was undertaken to determine the tolerance of a baboon to LO-CD2a, to analyze the effects of this mAb on some of the membrane markers of baboon lymphocytes and to determine the half-life of LO-CD2a in serum.

Staining of baboon cells with LO-CD2a results in <20% positive cells at a mean fluorescence intensity significantly lower than that of stained human cells. This staining pattern may reflect weak cross-reactivity or binding via Fc interaction with baboon cells.

The study was done on a male baboon (papio mormon) weighing 8.8 Kg. Before each injection of LO-CD2a the monkey was anesthetized; the first time with KETALAR (2 ml) and PRAZINE (0.5 ml), the second time with KETALAR only and the subsequent times with KETALAR and PRAZINE (0.3 ml). LO-CD2a was injected intravenously (i.v. in 10 min.), diluted in 100 ml of physiological saline. For phenotypic analysis of lymphocytes and measurement of circulating antibodies (injected LO-CD2a, newly formed anti-LO-CD2a antibodies, and preexisting cross-reacting baboon anti-LO-CD2a antibodies), blood samples (10 ml) were taken in two tubes. The tube for lymphocyte typing contained EDTA. Samples were taken prior to the first treatment to determine baseline levels.

The first dose (10 mg) of LO-CD2a was administered on day 0 of the study; the four following doses (10 mg/dose) were administered on days 7, 8, 9, and 10. Blood samples were taken a few minutes after each LO-CD2a dose. On days 7 and 9 a supplementary blood sample (in an EDTA-containing tube) was also taken before the LO-CD2a injections. Blood samples were taken on days 1, 2, 11, 12, 13, 16 and 24.

No abnormal reactions in activity or feeding habits were observed during LO-CD2a injections or throughout the period of study. The weight of the animal remained around the 8.8 Kg measured at day 0 (see table below).

Weight of baboon (in Kg) from day 0 to day 24

| Day | 0 | 7 | 8 | 9 | 10 | 12 | 13 | 16 | 24 |
|---|---|---|---|---|---|---|---|---|---|
| Weight | 8.8 | 8.9 | 9.1 | 9.1 | 8.8 | 9.0 | 9.1 | 8.9 | 8.9 |

Analysis of Phenotype and Circulating mAb

Figure 19:
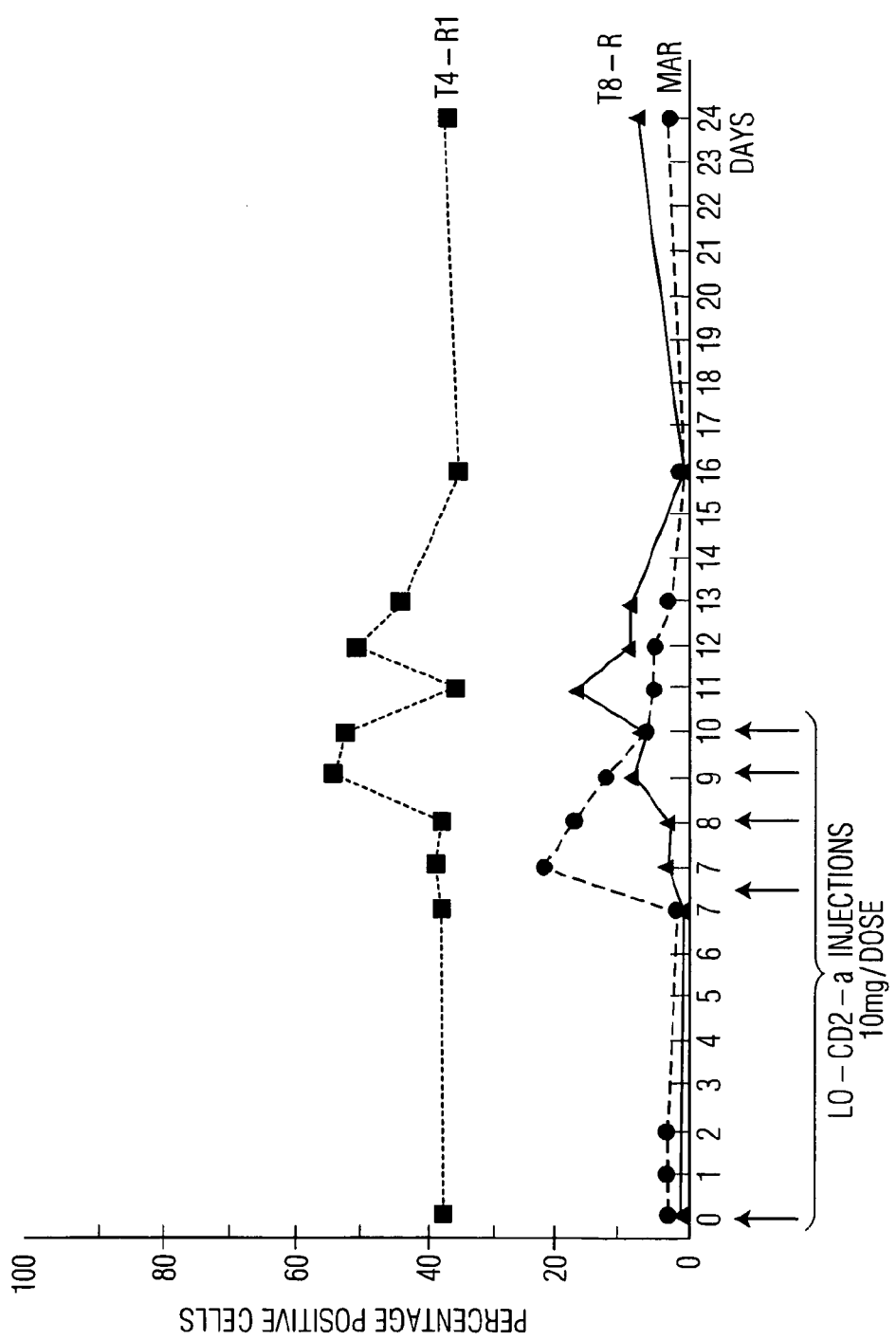

The fluorescent staining of this baboon's peripheral blood lymphocytes revealed some interesting features:

a) Under the effect of LO-CD2a the CD2–positive subset of lymphocytes decreased significantly (as revealed by two different anti-CD2 mAbs) at the end of the 5th dose of LO-CD2a, that is at the time of a maximal accumulation of mAb in blood (see FIGS. 17*a* and 17*b*). Given that the CD4+ and the CD8+ subsets of lymphocytes do not decrease during this period (FIG. 19), and because the CD4+ and CD8+ cells comprise most of CD2 bearing lymphocytes, the decrease in $CD2^+$ cells indicates that it is the membrane marker expression that is decreasing or altered in conformation, rather than the lymphocytes.

As can be seen in (FIG. 17*a*), a slight decrease of CD2+ ($Leu-5b^+$ or $T11^+$) positive lymphocytes is observed after the first dose of LO-CD2a. Two days after this first dose, the level of CD2 positive cells ($Leu 5b^+$ of $T11^+$) rose to the starting values.

At the end of the four 24-hour spaced doses of LO-CD2a (days 7-10) the percentage of CD2 positive cells ($Leu 5b^+$ or $T11^+$) decreased sharply and began to rise slowly 3 days after the end of the LO-CD2a administration.

b) At the same time, the percentage of LO-CD2a positive cells, that is, the percentage of cells bound by the circulating mAb rose to 22% after the 2nd dose of LO-CD2a (day 7) and then decreased as did the $CD2^+$ cells revealed by the anti-CD2 mAbs Leu-5b and T11 (FIG. 17). The decrease of LO-CD2a+ cells was revealed by the MARK-3FITC mAb (FIG. 18).

The decrease of LO-CD2a+ cells was determined by detection of the LO-CD2a present on cells as detected by MARK3-FITC or by the MARG2b-8-biotin conjugated mAbs (FIG. 18*a*). The same phenomenon was observed if cells were first incubated with LO-CD2a at 2.5 ig/ml to saturate all the sites unoccupied by circulating mAb. LO-CD2a was detected by MARK-3-FITC or MARG2b-8-biotin (FIG. 18).

c) As can be seen in (FIG. 19), the T4 positive subset of baboon lymphocytes showed a moderate rise during days 9 to 12 after which the percentage of $T4^+$ lymphocytes returned to its initial value. Concomitantly with the rise in $T4^+$ cells, the percentage of T8 positive lymphocytes rose from day 9 to day 11. After that day this percentage returned to initial values.

d) The levels of circulating mAb LO-CD2a decreased to background values 3 days after the first injection (see FIG. 17*b*). When LO-CD2a is applied in four short-time spaced doses (days 7 to 10), the levels of serum LO-CD2a (around 3.7 mg/ml, maximal value in this period) decreased slowly after the last dose (days 10 to 16), indicating a relatively long half-life of the Ab in this animal model. No baboon anti-LO-CD2a antibodies were detected in the blood samples collected on days 11, 12, 13, 16 and 24.

Conclusion

LO-CD2a seems to be well tolerated by non-human primates, as demonstrated by the absence of apparent reactions in cynomolgus monkey baboon. LO-CD2a seems to have a relatively long half-life in the baboon. Twenty-four hours after the first dose of LO-CD2a (day 1 in FIG. 24*b*), 50% of the maximal detectable level of MAb was still present in serum. Three days after the last dose of LO-CD2a (day 13 in FIG. 24*b*), 50% of the maximal detectable level of mAb was still present in serum.

Although the staining pattern in non-human primates is not consistent with that observed for CD2 on human cells, the decrease in the percentage of CD2 positive lymphocytes followed by a slow rise of this percentage of cells is similar to that observed in human PBMC mononuclear cells cultured in the presence of LO-CD2a.

EXAMPLE 5

Patients Treated with LO-CD2a

Patients Treated with LO-CD2a on a Compassionate Basis

PATIENT #1 (Mb.E.)

This was a female patient with chronic pyelonephritis, who was treated with a renal allograft for end-stage renal failure. A rejection crisis occurred and was treated with 10 days of OKT3. The creatinine level dropped from 2 to 1.4 mg/dl. Approximately four (4) months later a rejection crisis was diagnosed by a creatinine level of 2 mg/dl and a biopsy indicating moderate rejection. The patient was treated with 1.5 g SOLUMEDROL and a course of ATG for the following eight (8) days at which time the creatinine level was 1.65 mg/dl. Seven days after treatment a biopsy was performed and indicated cellular rejection and moderate vascular rejection. Two days after the biopsy (day 0) the patient was anuric with a creatinine level of 2.4 mg/dl. That same day the patient received 10 mg of LO-CD2a, 1.5 g of the corticosteroid SOLUMEDROL, plus 1 g POLARIMIN (an anti-histamine) and 1 g DAFALGAN (acetaminophen). The treatment with the corticosteroid, dexchlorpheniramine and acetaminophen is referred to by the transplant community as "coverage". No side effects were noted. By the end of 23 hours, the patient produced 700 ml of urine and the creatine was 2.72 mg/dl. For the next 9 days she received 10 mg/day of LO-CD2a. The patient left the hospital without a follow-up biopsy at that time, Day 11.

Measurement of serum creatinine level during ATG treatment and during the following LO-CD2a treatment indicated the creatinine level rose despite ATG treatment and fell and stabilized with LO-CD2a (FIG. 27).

Figure 20:
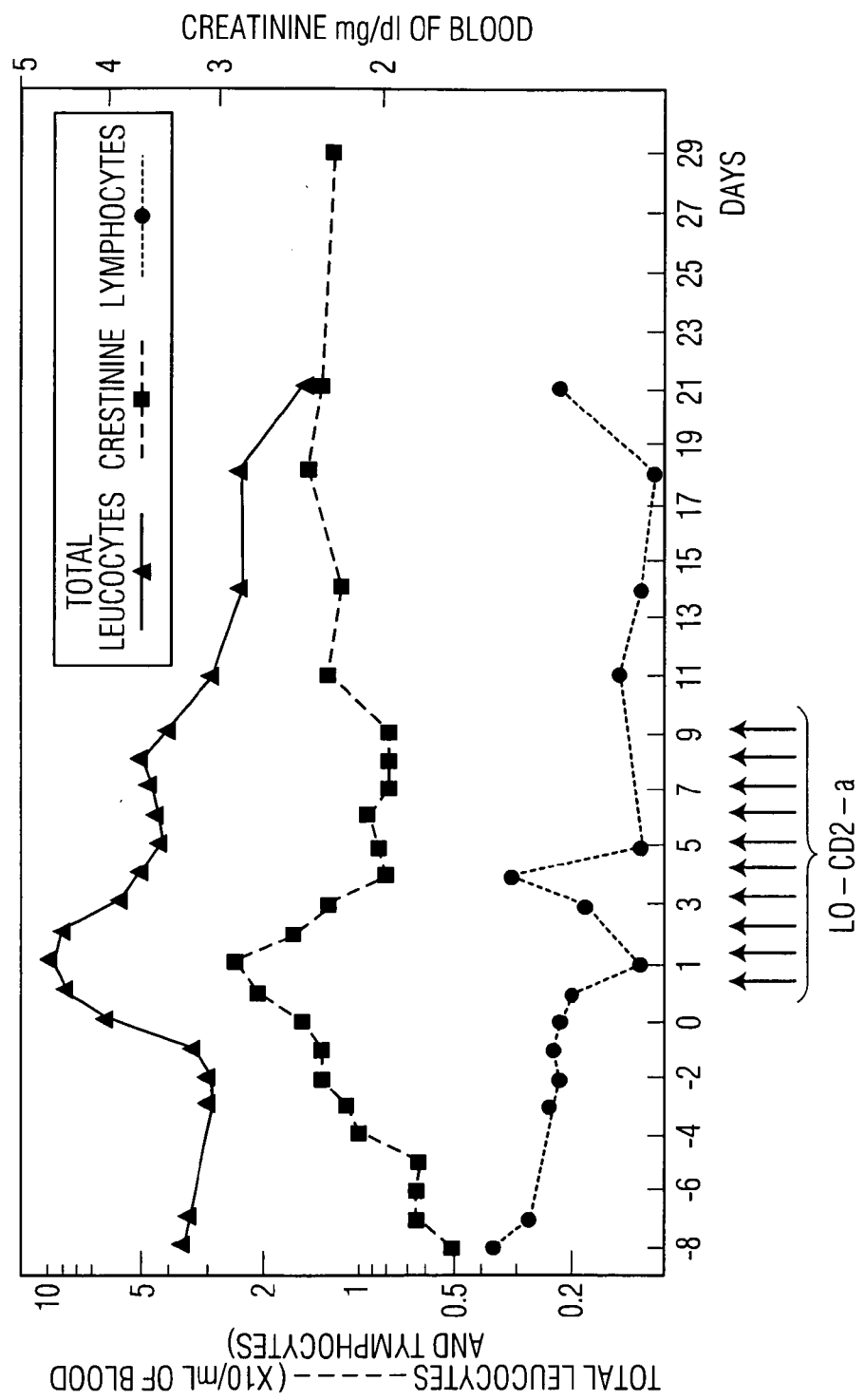

The leukocyte count fell from a high of 10,000 to 2,000 during the treatment with LO-CD2a and continued to fall until the last measurement on day 21 (FIG. 20). The lymphocyte count was low and variable during the period of observation.

Figure 21:
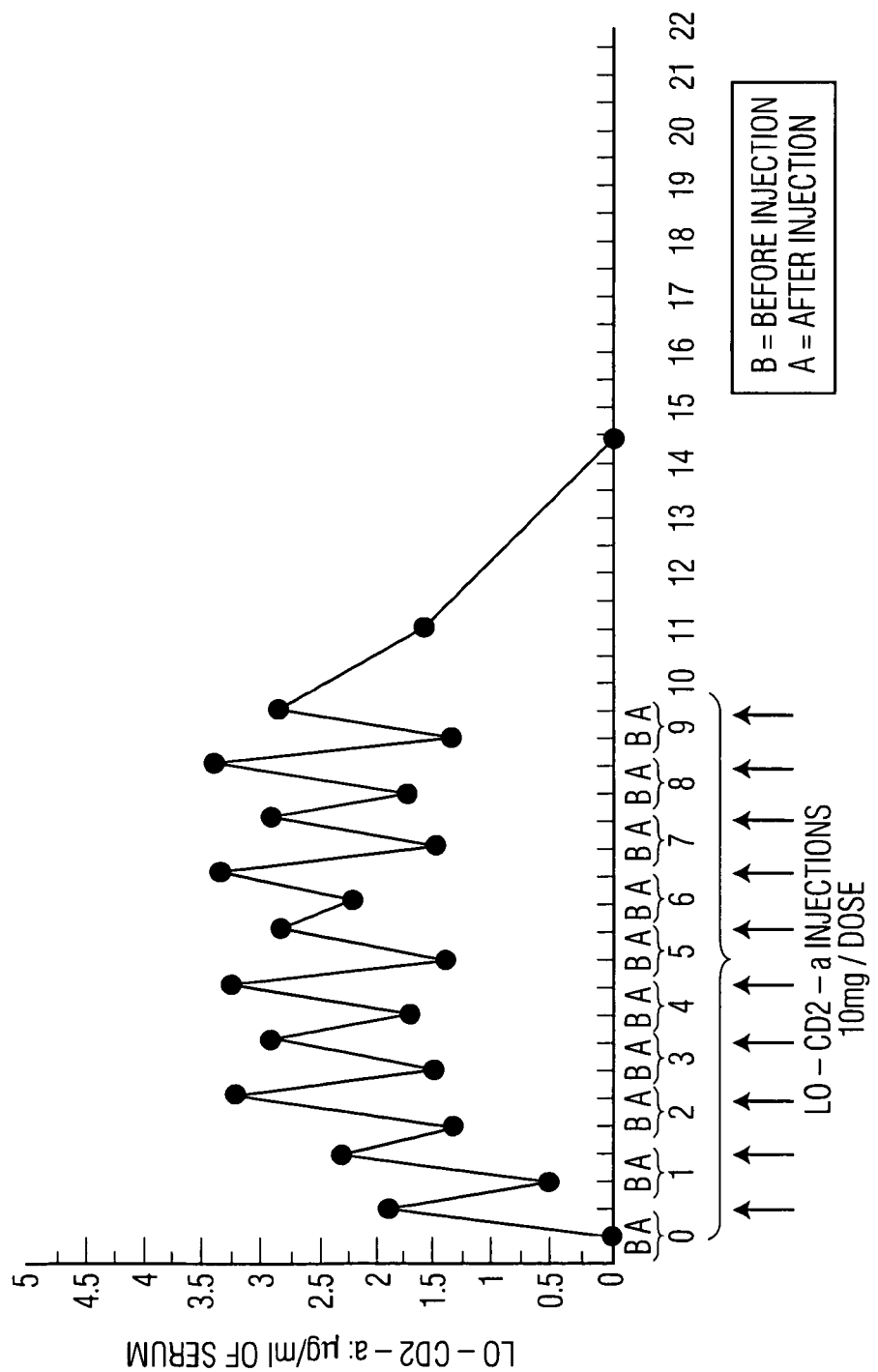

The serum levels of LO-CD2a rose to peaks of 2.0-3.0 ig/ml immediately following each treatment and fell to lows of approximately 1.0 ig/ml between each treatment (FIG. 21). With the last treatment on day 9, the level fell by 50% in 24 hours and to 0 by day 14. This patient returned to the clinic on day 40.

The patient's creatinine level was 2.27 on day 40, 2.48 on day 50 and rose to 3.11 by day 66 at which point a biopsy was obtained, with the initial report consistent with severe cellular rejection and interstitial hemorrhage (see below). The patient was treated with 150R of irradiation to the kidney, 3×125 mg SOLUMEDROL, while continuing on maintenance therapy of cyclosporin plus 12.5 mg/day of steroids. The creatinine level continued to rise during the subsequent period. On day 70 the creatinine level was 3.3; day 80, 5.63; day 84, 8.35. By day 86 the creatinine level was 10.8 and a transplant nephrectomy was performed on day 88. This patient's compliance with maintenance immunosuppression during the period between her discharge on day 10 and her biopsy on day 66 is in question and the loss of the kidney despite the evidently successful rescue must factor in the uncertain compliance.

(ii) Patient #2

The patient was a 38 year old male who was Hepatitis C⁺. He had received a renal allograft for the treatment of end stage renal failure due to chronic interstitial nephropathy. One year and three months later, he underwent a transplant nephrectomy due to acute cellular and vascular rejection resistant to a course of OKT3.

One year and ten months from the transplant nephrectomy, he received a second renal allograft. Three days later his creatinine level was 1.4 mg/dl. Three days later he received 500 mg SOLUMEDROL; the patient's creatinine later that day was 1.8 mg/dl. On the following day he received 500 mg of SOLUMDROL; creatinine was 3.25 mg/dl. The following day he received 500 mg SOLUMEDROL; his creatinine was 2.95 mg/dl. Three days later his creatine level was 2.3 mg/dl and he underwent a biopsy which demonstrated 3 plus cellular rejection. Three days later he received 10 mg LO-CD2a, plus 200 mg SOLUMEDROL. POLARAMIN and DALFAGAN. Side effects observed were limited to sleepiness; no hyperthermia or hypertension were noted. For the next 9 days he received daily treatments of 10 mg of LO-CD2a. The day following the end of such treatments a biopsy showed no signs of rejection.

The patient tolerated the course of LO-CD2a well with no evidence of clinical side effects, including no fever or hypertension with any dose. Routine hematological and clinical chemistry laboratory tests (including LFTs) obtained during the course of treatment demonstrated no alterations attributable to the administration of the antibody, except for a decrease in the lymphocyte count from 290/cubic mm to a low of 100/cubic mm and the reduction in creatinine level associated with resolution of the rejection crisis (from 2.7 mg/dl at the initiation of treatment with LO-CD2a to 1.10 at the end of the course).

Figure 22:
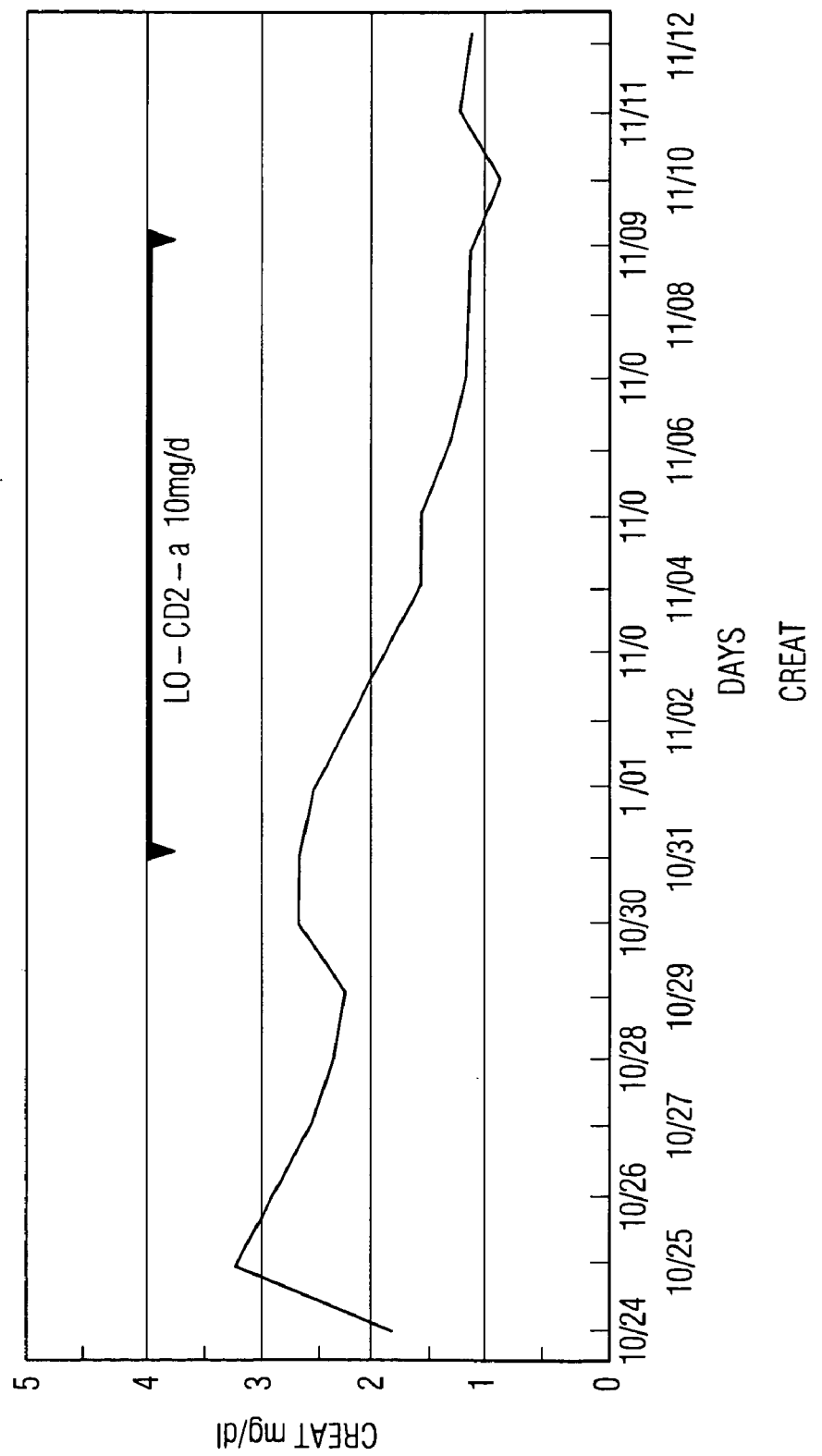
Figure 23:
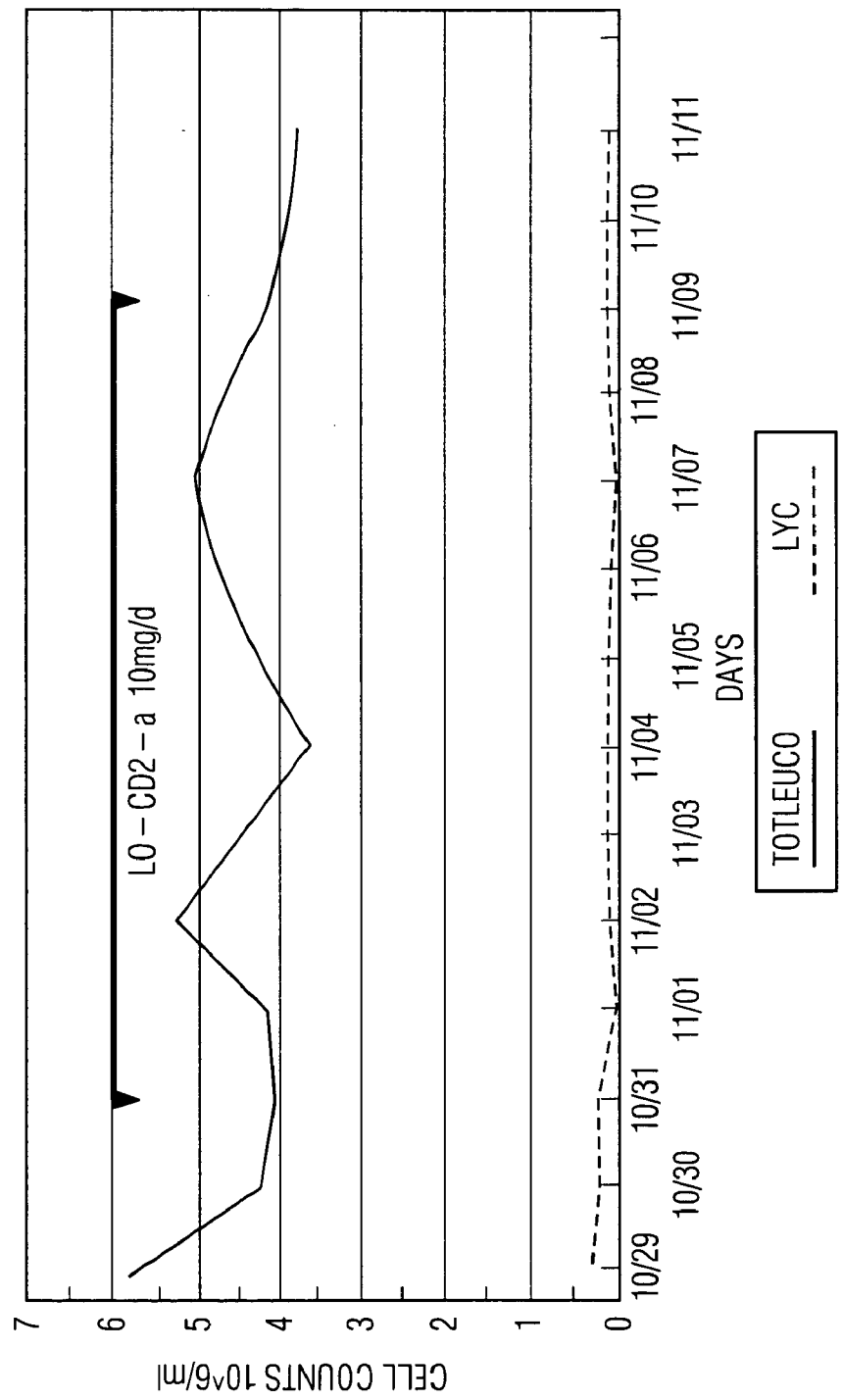
Figure 24:
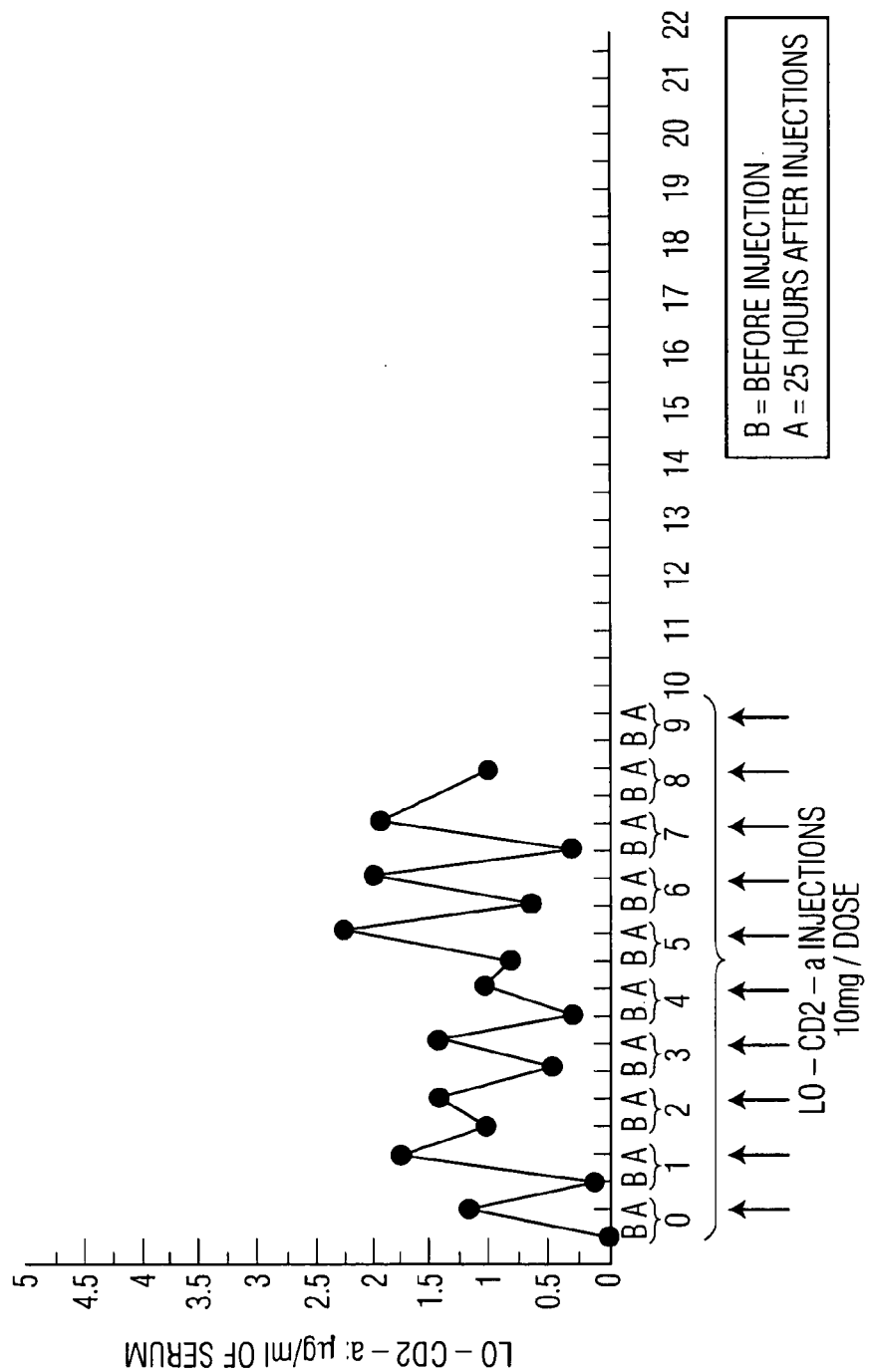

FIG. 22 shows the serum creatinine level of this patient, as falling from 2.5 to approximately 1.0 on the days following treatment with LO-CD2a. The patient was lymphopenic prior to and during treatment and the leukocyte count showed no dramatic alteration with treatment (FIG. 23). In this patient the serum levels of LO-CD2a did not rise above 2.0 ig/ml after each treatment and fell to lows of 1.0 to less than 0.25 ig/ml (FIG. 24). Eight months after the first treatment with LO-CD2a the patient was doing well with normal renal function and no evidence of recurrent rejection.

Patient 2—Biopsy #1—Diagnosis: Indeterminate.

The biopsy contained about 20 glomeruli which are unremarkable. There was a sparse mononuclear infiltrate with a minor degree of interstitial edema. Only minor degrees of tubular invasion were found and no vascular lesions. These findings are insufficient for the diagnosis of acute cellular rejection. There were rare mononuclear cells in small arteries, which were suspicious, but did not meet the criteria for the diagnosis of rejection.

Patient 2—Biopsy #2 Approximately 2 weeks after the first biopsy—No diagnostic abnormality recognized.

The biopsy looked similar to the previous biopsy and contained about 10 glomeruli. The infiltrate was very sparse and no vascular lesions were identified.

(iii) Patient #3

The patient was a 19 year old with von Willebrand disease who received a renal allograft for the treatment of end stage renal failure due to chronic pyelonephritis. The transplant was removed on 17 days later due to acute vascular rejection with secondary hypertension after failure of a 6 day course of OKT3.

Five and one-half months later he received a second renal allograft. Ten days later his creatinine level was 6 mg/dl. The next day the creatinine level was 7 mg/dl and a biopsy indicated 3 plus cellular rejection and vascular rejection (proliferative endarteritis without necrosis or thrombosis). That same day he received 10 mg of LO-CD2a, 40 mg SOLUMEDROL and POLARAMIN and DAFALGAN. No side effects were observed. For the next 9 days he received daily treatments of 10 mg of LO-CD2a, with no other drugs and no side effects. Two days after completion of the treatment, his creatinine level was 1.75 mg/dl and a biopsy indicated no sign of acute rejection, with interstitial necrosis and one focal spot of chronic rejection.

No clinical side effects (alteration in BP or temperature) were observed. Routine hematological and clinical chemistry laboratory tests (including LFTs) showed no changes attributable to administration of the antibody except the decrease in creatinine level associated with the resolution of the rejection crisis (from 7.10 mg/dl on the initiation of treatment with LO-CD2a to 1.75 mg/dl at the end of the 10 day course). The lymphocyte count was 340/cubic mm prior to treatment and fell to a low of 220/cubic mm during treatment, rose to 690/cubic mm 9 days after cessation of treatment with the LO-CD2a and had risen to 1000/cubic mm 23 days after the end of treatment.

Figure 25:
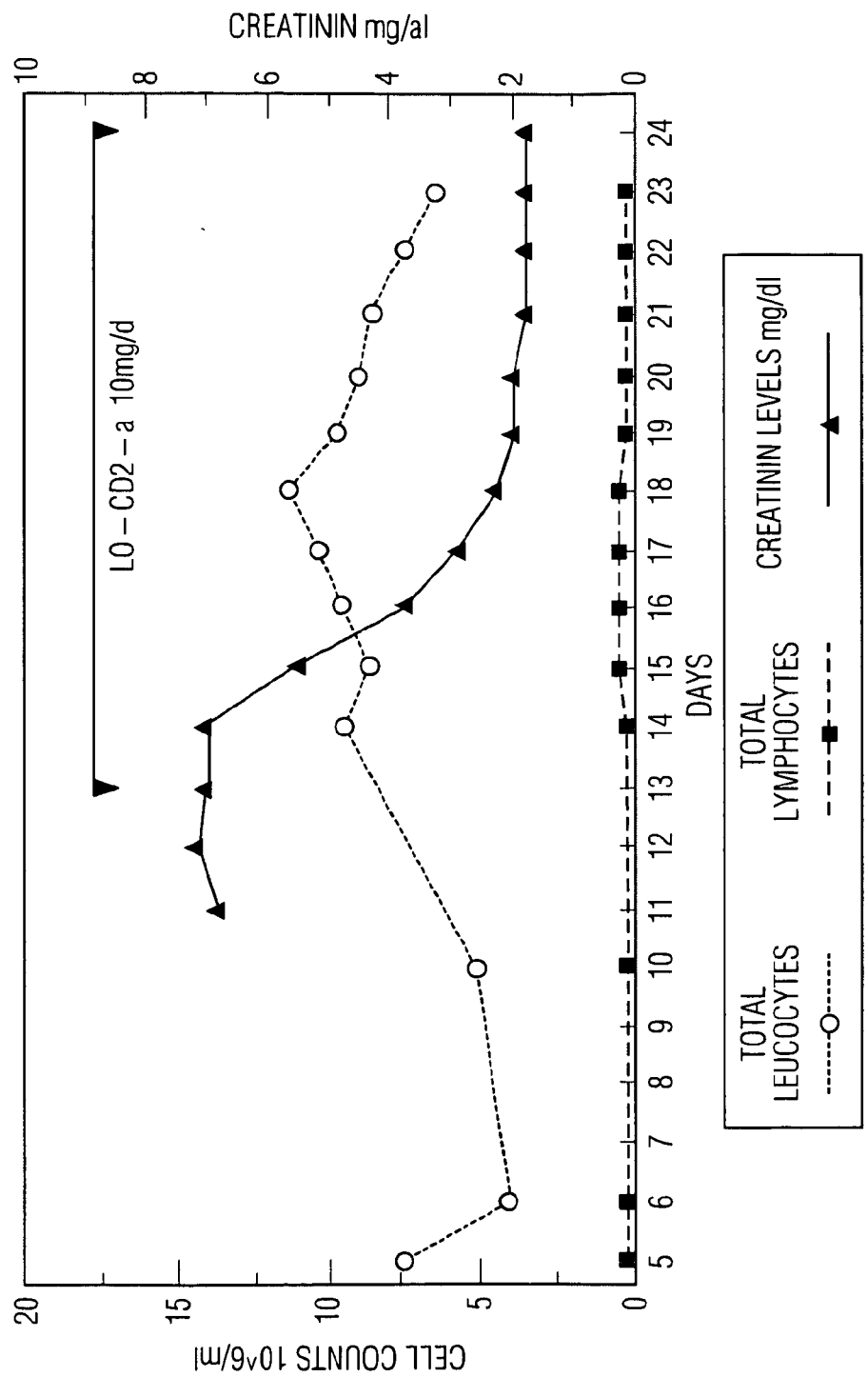
Figure 26A:
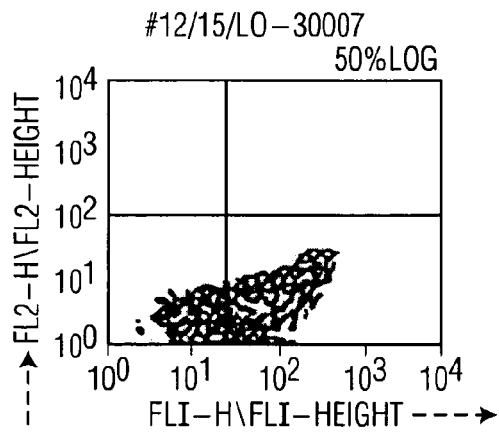
Figure 26B:
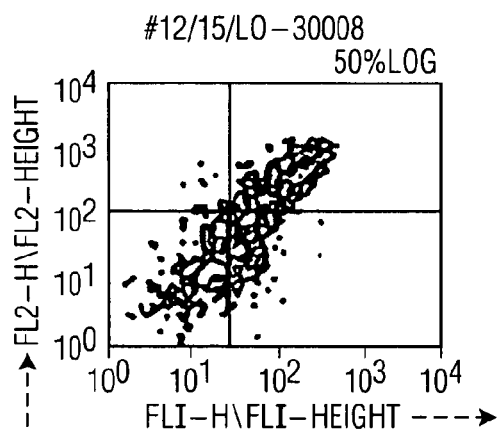
Figure 26C:
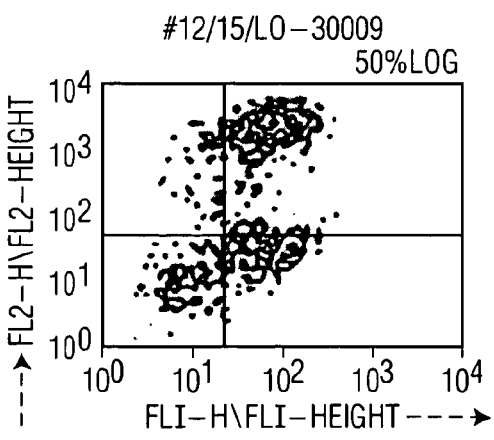
Figure 26D:
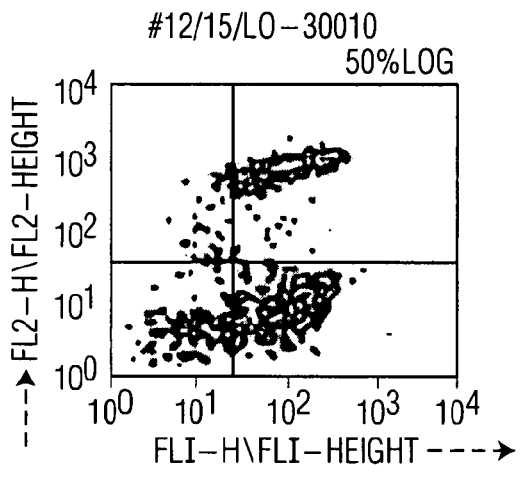
Figure 26E:
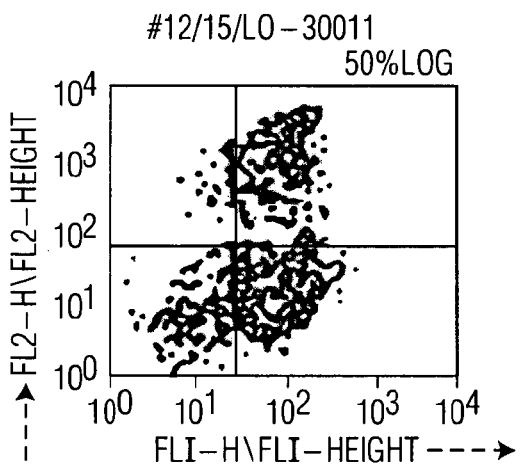
Figure 26F:
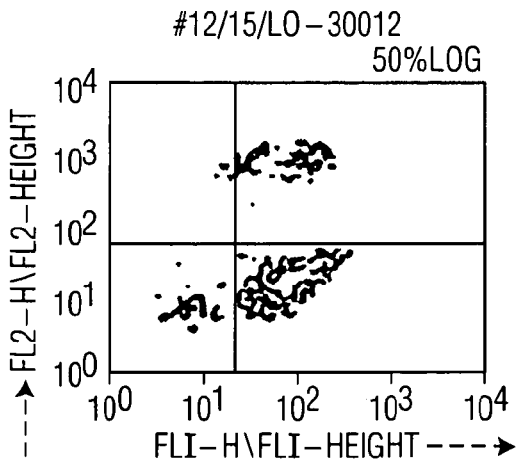
Figure 26G:
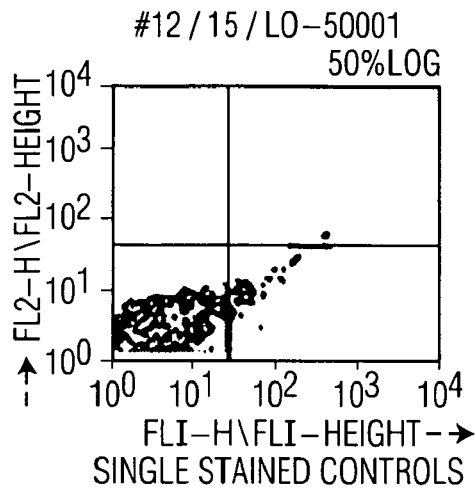
Figure 26H:
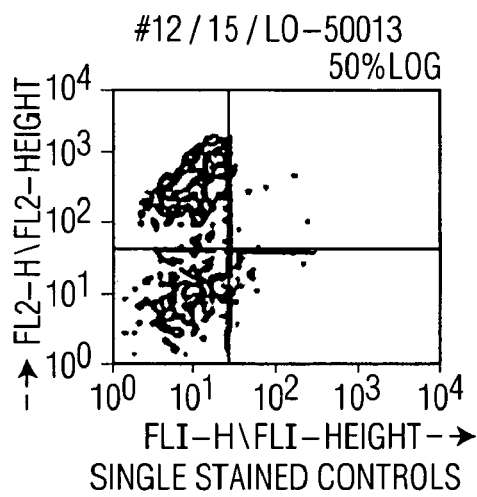
Figure 26I:
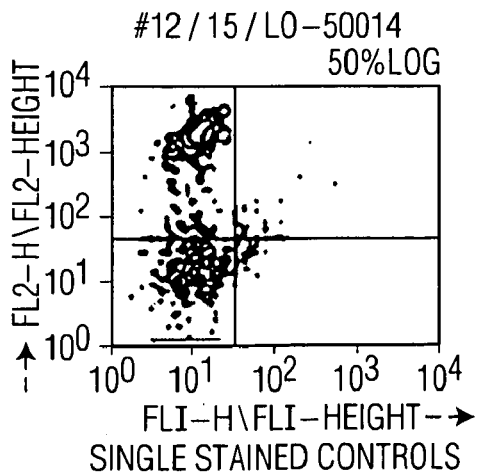
Figure 26J:
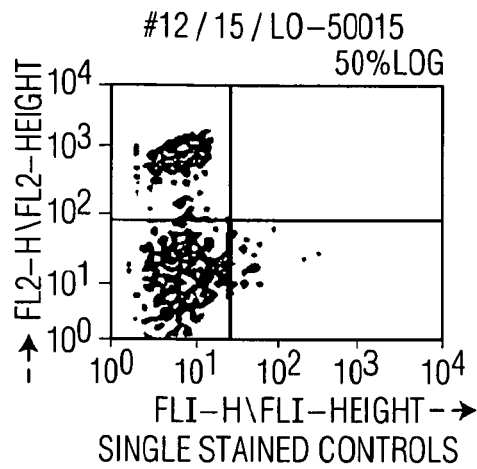
Figure 26K:
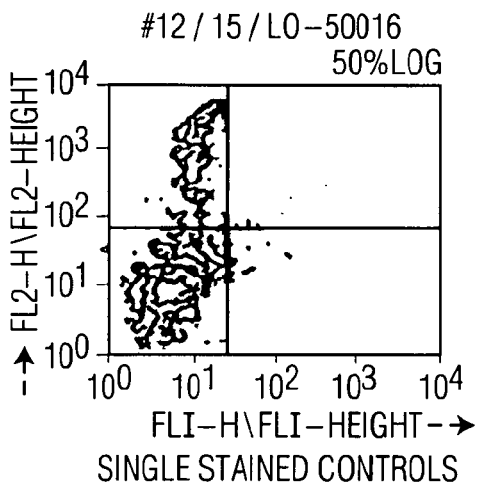
Figure 26L:
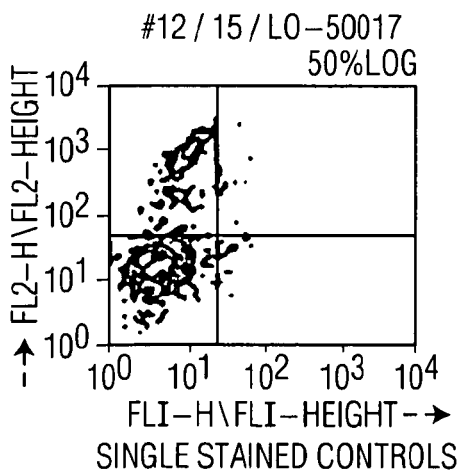
Figure 27A:
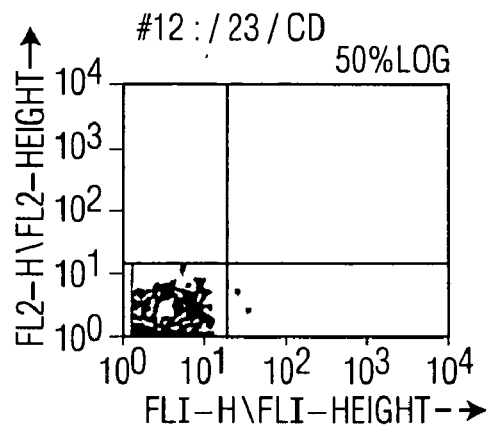
Figure 27B:
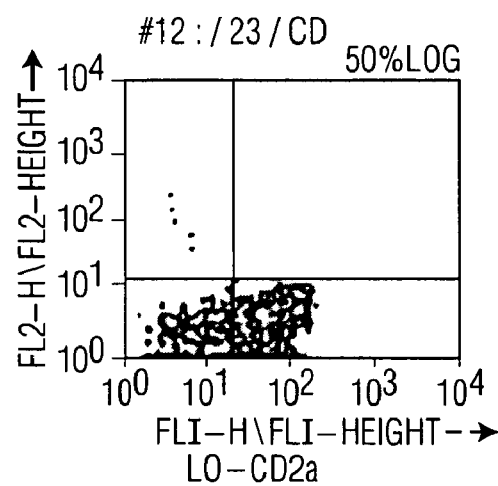
Figure 27C:
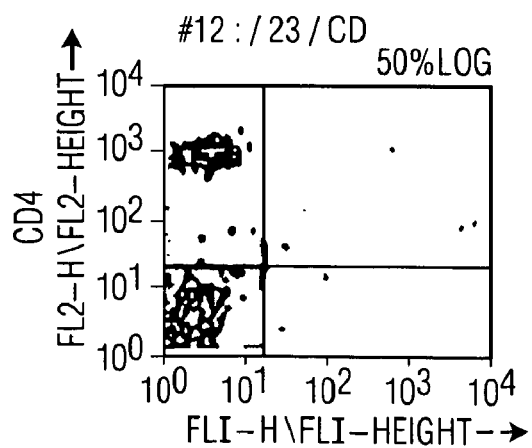
Figure 27D:
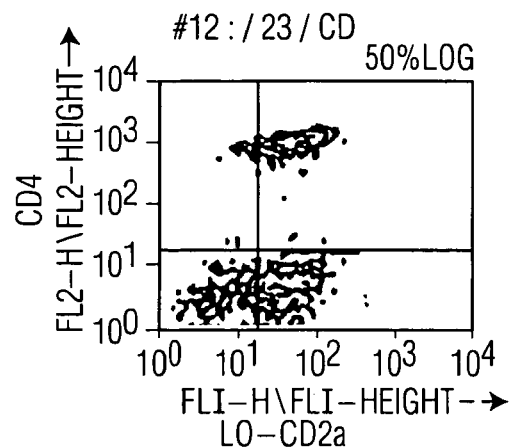
Figure 27E:
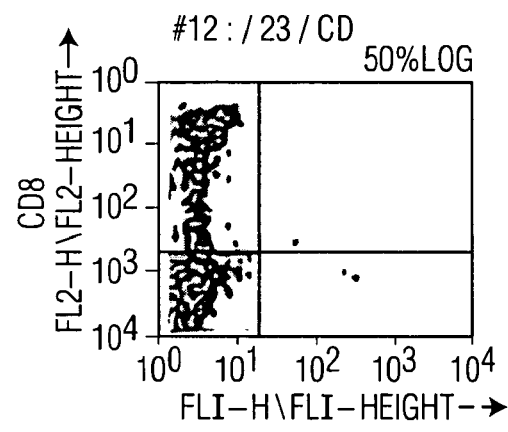
Figure 27F:
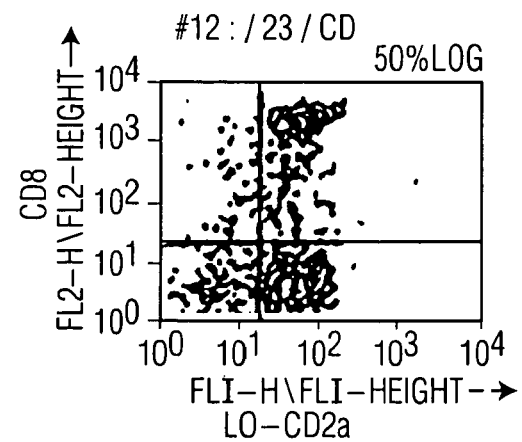
Figure 27G:
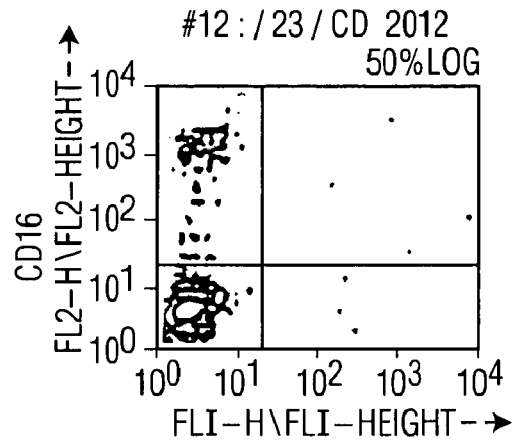
Figure 27H:
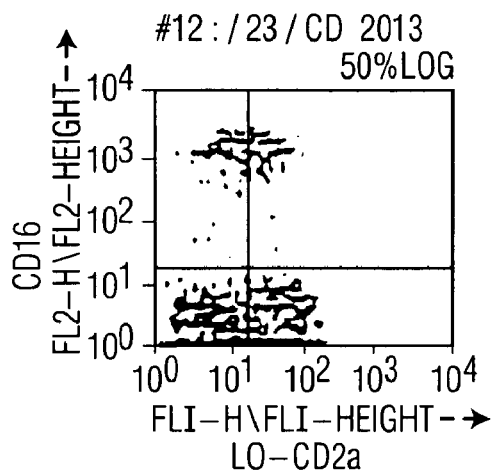
Figure 27I:
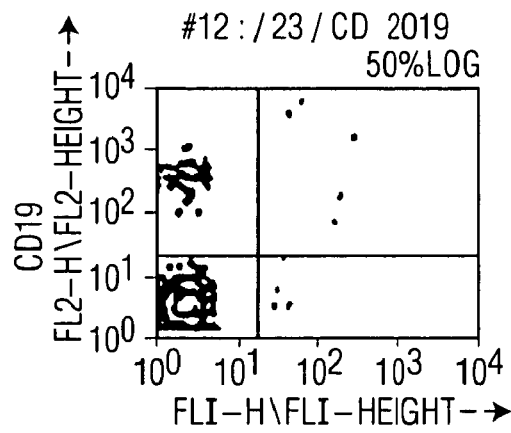
Figure 27J:
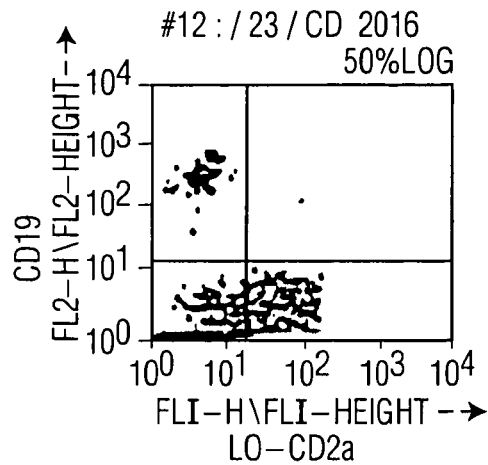
Figure 27K:
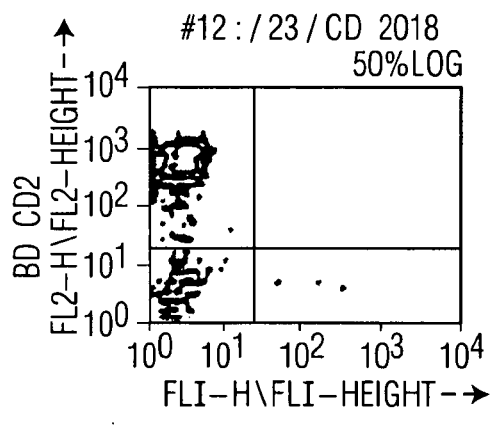
Figure 27L:
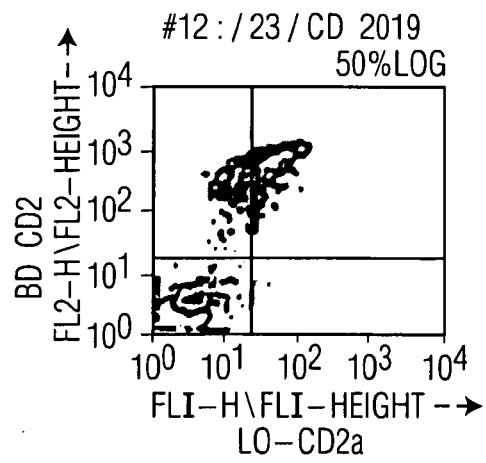
Figure 28A:
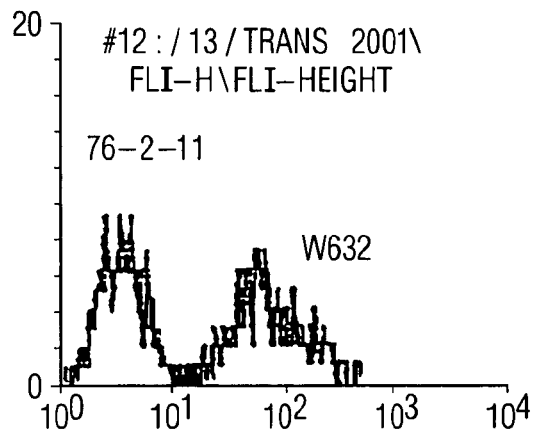
Figure 28B:
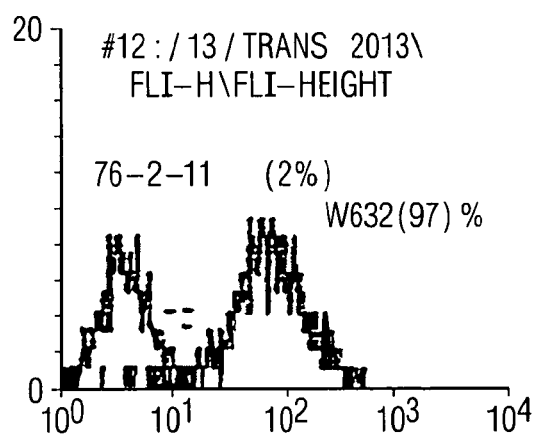
Figure 28C:
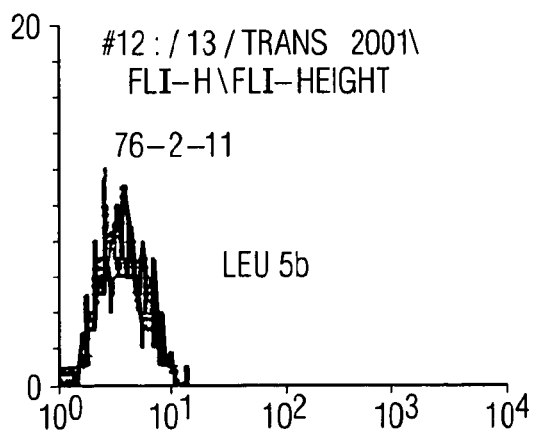
Figure 28D:
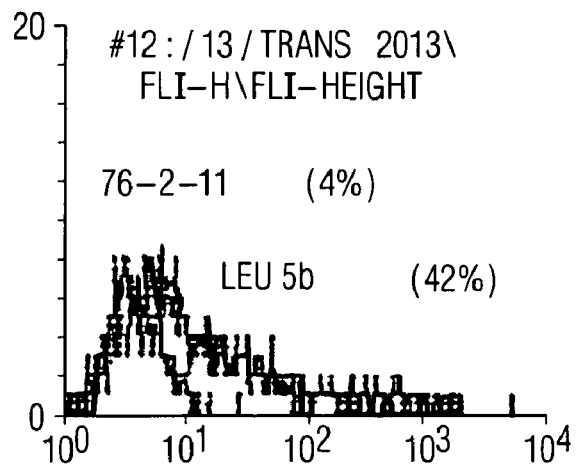
Figure 28E:
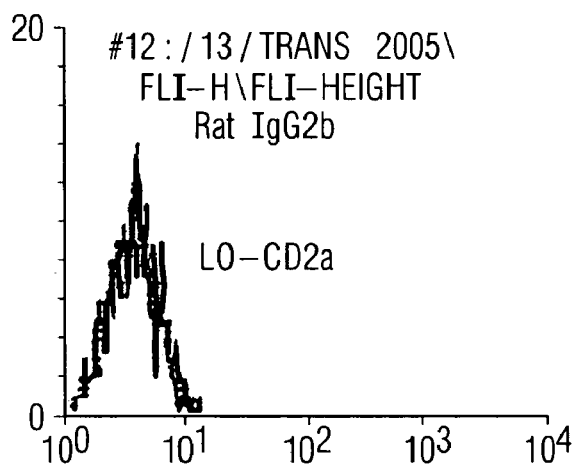
Figure 28F:
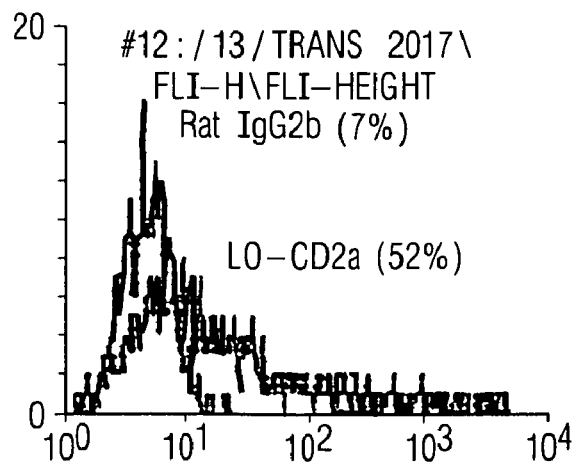

The leukocyte count in this patient was not significantly altered by treatment (FIG. 25). The serum creatinine level fell dramatically with treatment (FIG. 25). Seven months after the first treatment with LO-CD2a the patient was doing well with normal renal function and no evidence of recurrent rejection.

Patient 3—Biopsy #1—Diagnosis: Severe cellular rejection affecting small arteries and to a lesser degree the interstitium and glomeruli.

An arcuate sized artery showed a marked mononuclear infiltration of the intima with disruption of the elastica. There was sparse infiltrate in the interstitium, which occasionally invaded tubules. The interstitium showed diffuse, mild interstitial edema. There were about 7 glomeruli present. These show hypercellularity with mononuclear cells and endothelial swelling. Overall, this pattern was diagnostic of severe, acute cellular rejection.

Patient 3—Biopsy #2 Approximately 2 weeks after the first biopsy—Diagnosis: Consistent with treated rejection.

The biopsy showed a few small arteries, which show intimal fibrosis sometimes with a mucoid material but a very minimal cellular infiltrate. The interstitium showed a fine diffuse fibrosis and a minimal mononuclear infiltrate. Tubules were locally atrophic but otherwise unremarkable. There was no evidence of active cellular rejection.

No subsequent rejection episodes have been reported during 28 months of follow-up of the second and third patients who remained compliant with their immunosuppressive therapy.

(iv) Patient #4

The patient who was suffering from severe graft versus host disease (severe skin, gut, renal and CNS toxicity resistant to high dose prednisone) after an allogeneic bone marrow transplant received 12 days of LO-CD2a at 10 mg/day. His symptoms improved; renal function returned to normal, diarrhea ceased, skin improved and confusion resolved. Four days after the antibody was stopped the symptoms recurred and the patient died despite the initiation of a second course of antibody.

LO-CD2a thus could be used to reverse ongoing immune responses to foreign tissues (allogeneic and xenogeneic, since it inhibits the xeno MLR as well as the allo MLR). The antibody would be given by i.v. infusion once or twice a day for 10 days to 14 days. It may also be used prophylactically to prevent activation of T cells as part of the induction protocol immediately following organ transplantation.

In a second experiment, a Phase I safety, pharmacokinetic and dose-finding clinical trial was initiated in renal allograft recipients undergoing an initial biopsy proven acute rejection episode. The antibody preparation used in this trial is LO-CD2a, produced in cell culture.

Compassionate use of the antibody showed no side effects and suggested efficacy in reversing acute graft rejection at a dose of 10 mg/day for 10 days. Preclinical studies with chimpanzees suggested that similar in vivo effects were observed with doses equivalent to human doses ranging from 0.1-100 mg/day with no obvious adverse effects. Therefore an objective of this Phase I trial was to investigate decreasing dose levels of LO-CD2a starting at 10 mg/day for ten days (with an optional extension for an additional five days) in order to obtain indications of the minimal effective dose. Because no side effects had been observed with steroid 'coverage' in the compassionate use patients described above, it was decided to administer the antibody with no steroid coverage and only minimal pretreatment with analgesics and antihistamine. This was done to characterize predictably the side effects induced by LO-CD2a.

Eleven patients have been enrolled under this protocol to date. Four patients were treated with 10 mg/day, five patients were treated at 5 mg/day and two patients were treated with 2.5 mg/day.

Among the eleven patients enrolled, nine patients experienced reversal or partial reversal of acute rejection confirmed by biopsy: all four patients treated with LO-CD2a at mg/day, three of the patents treated with 5 mg/day, and both patients treated with 2.5 mg/day. One of the patients treated with 5 mg/day (Patient 8, see below) withdrew from the study voluntarily after the first dose and a second patient treated with 5 mg (Patient 9) showed a poor response.

Table 2 summarizes results obtained with renal rejection patients treated with LO-CD2a under this protocol.

TABLE 2

| Patient | Dose (mg/day) | Number of rejections | Rejection Reversed? | Recurrent Rejection? |
|---|---|---|---|---|
| #1 | 10 | 1st | Yes | No (13 mo.) |
| #2 | 10 | 1st | Yes | Yes$_{noncompliant}$ (13 mo.) |
| #3 | 10 | 1st | Yes | Yes (1 mo.) |
| #4 | 10 | 1st | Yes | No |
| #5 | 5 | 1st | Yes | No (10 mo.) |
| #6 | 5 | 1st | Yes | No (10 mo.) |
| #7 | 5 | 1st | Yes | No (9 mo.) |
| #8 | 5 | 1st | N/A[1] | N/A |
| #9 | 5 | 1st | No | N/A |
| #10 | 2.5 | 1st | Yes | Yes (5 mo.) |
| #11 | 2.5 | 1st | Yes | No (4 mo.) |

[1] withdrew at patient's request

Adverse events observed during treatment with LO-CD2a without steroid coverage included nausea, vomiting, fever, chills, and hypertension, possibly as a result of a transient release of cytokines. The majority (greater than 70%) of these events were observed during administration of the first dose and were of limited extent and duration. For example, no fevers greater than 40° C. were observed and most of the events resolved within hours of onset. No hypotension or severe diarrhea was observed. There was no clear relationship between the intensity and incidence of these events and antibody dose. Despite the obvious discomfort of these symptoms, no events required emergent resuscitative measures.

In a third experiment, ten patients with acute renal allograft rejection were treated on a compassionate basis without steroid coverage with LO-CD2a as follows:

Two were treated with 10 mg/day, four were treated with 5 mg/day, and four were treated with 2.5 mg/day. All compassionate use patients treated with 10 mg/day and 5 mg/day, and all but one at treated with 2.5 mg/day showed evidence of complete or partial resolution of rejection by biopsy and other clinical signs. The adverse event profile with these compassionate use patients resembled that seen hereinabove with predominantly first-dose symptoms of limited duration and extent.

In a fourth experiment, six patients with steroid resistant graft versus host disease, and one liver transplant recipient have received LO-CD2a on a compassionate use basis. No adverse events were reported for these patients. Brief narratives for these patients follow.

All six GvHD patients were treated by 10 consecutive daily doses of 10 mg of LO-CD2a, administered intravenously over one hour. Concomitantly, cyclosporin and steroids were continued. All but one patient showed an improvement over their GvHD symptoms. The resolution of the GvHD symptoms began on day 3-6 after starting mAb therapy. A progression of signs of hepatic GvHD under mAb therapy has been observed in two patients. Relapse of signs of GvHD was seen in 2 out of 3 evaluable patients.

A seventh patient had received a donor liver, but unfortunately had developed sepsis as a result of a surgical complication accompanied by renal failure due to cyclosporin toxicity and severely depressed bone marrow function. Because of her condition, the surgeon did not wish to risk the patient or a second liver that had been allocated by using currently available immunosuppressive agents (OKT3, MOFETIL, FK506, cyclosporin and ATG) for induction. The patient received the liver transplant and treatment with LO-CD2a for seven days at 5 mg/day with the first dose infused during surgery beginning prior to declamping of the transplanted organ. The subsequent doses were given with low dose steroids. During the treatment period, the patients renal function improved sufficiently for a conventional immunosuppressive regimen to be initiated. The patient has not shown any signs of rejections at eight weeks post transplant.

Although the present invention, in a preferred embodiment, is directed to inhibition of graft rejection, it is to be understood that the scope of the invention is not limited thereto and is generally useful for the inhibition of T-cell activation for any and all purposes.

EXAMPLE 6

Construction and Expression of Chimeric Antibody

A. Cloning and Sequencing of $V_H$ and $V_L$ of LO-CD2a

Total RNA was isolated from the cell line LO-CD2a (ATCC HB 11423) according to the method of Chirgwin (*Biochemistry*, 18:5294, 1979). mRNA was then prepared using The OLIGOTEX-dT mRNA kit (Qiagen, Chatsworth, Calif.). Approximately 200-300 ng mRNA was reverse transcribed using the RNA-PCR kit from Perkin-Elmer Cetus (Norwalk, Conn.). The reaction was carried out at 42° C. for 1 hour. Oligonucleotide primers required for amplification of $V_H$ and $V_L$ genes were chosen using the following references: 1) *Sequences of Proteins of Immunological Interest*, Kabat et al., 5th ed., 1991, 2) Orlandi et al., *Proc. Nat'l. Acad. Sci., (USA)* 86:3833-3837 (1989).

```
V_L sense

Sma 1    #1  2   3   4   5   6   7   8
      5'                                              3'
              AA CCC GGG GAC ATT CAG CTG ACC CAG TCT CAA (SEQ ID NO:1)

C_L antisense

Sal 1   #115 114 113 112 111 110 109
      5'                                              3'
              CA GTC GAC TAC AGT TGG TGC AGC ATC AGC (SEQ ID NO:2)

V_H sense

Sma 1    #1  2   3   4   5   6   7   8
      5'                                              3'
              AA CCC GGG GAG GTC CAG CTG CAG CAG TCT GG (SEQ ID NO:3)

CH_1 antisense

Sal 1    #124 123 122 121 120 119
      5'                                              3'
              AAG TCG ACC CAG TGG ATA GAC CGA TGG (SEQ ID NO:4)
```

The numbers refer to amino acid residues, as shown in Kabat, et al., 1991.

Polymerase chain reactions (PCR) were carried out in a Perkin-Elmer DNA Thermal Cycler 480 using the following conditions: 5 minutes at 94° C., 30 cycles consisting of 1 minute at 94° C., 2 minutes at 60° C., and 2 minutes at 72° C. This was followed by 5 minutes at 72° C. DNA fragments were gel purified from 1% agarose using the Qiaex gel extraction kit (Qiagen, Chatsworth, Calif.). The fragments were then blunt-ended according to the method of Kanungo and Pandey, *BioTechniques*, 14:912-913 (1993) and ligated into the Sma I site of Bluescript KSII+ (Stratagene, La Jolla, Calif.). Multiple clones were sequenced by the dideoxy chain termination method using the Sequenase™ T7 Polymerase Kit (U.S. Biochemical, Cleveland, Ohio).

Figure 29:
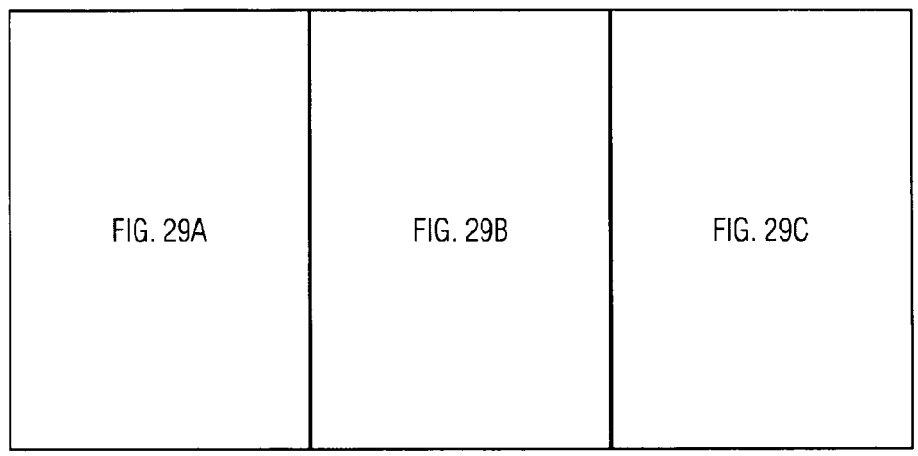
Figure 30:

Due to the potential error rate inherent in PCR, at least three separate reactions were performed. The most commonly observed sequences for LO-CD2a $V_L$ and $V_H$ genes are shown in FIGS. 29 and 30, wherein FIG. 29 shows the nucleotide and amino acid sequences of the LO-CD2a $V_L$ chain including the native leader sequence. FIG. 30 shows the nucleotide and amino acid sequences of the LO-CD2a $V_H$ chain including the native leader sequence.

As shown in FIG. 29, the leader sequence is from amino acid residues -20 to -1. Framework 1 is from amino acid residues 1 to 23. CDR1 is from amino acid residues 24 to 39. Framework 2 is from amino acid residues 40 to 54. CDR2 is from amino acid residues 55 to 61. Framework 3 is from amino acid residues 62 to 93. CDR3 is from amino acid residues 94 to 102. Framework 4 is from amino acid residues 103 to 112.

As shown in FIG. 30, the leader sequence is from amino acid residues -19 to -1. Framework 1 is from amino acid residues 1 to 30. CDR 1 is from amino acid residues 31 to 35. Framework 2 is from amino acid residues 36 to 49. CDR2 is from amino acid residues 50 to 66. Framework 3 is from amino acid residues 67 to 98. CDR3 is from amino acid residues 99 to 107. Framework 4 is from amino acid residues 108 to 118.

B. Insertion into Vectors for Transient Expression

Two vectors were licensed from The Medical Research Council (MRC) in London for expression of chimeric light and heavy chains of LO-CD2a respectively. The 9.2 kb light chain vector (hcmv-vllys-kr-neo) contains the genomic clone of the human kappa constant region and humanized $V_L$ domain of anti-lysozyme as a Hind III-Bam HI fragment. The 8.6 kb heavy chain vector (hcmv-VhLys-gammal-neo) contains the genomic clone of human ã1 constant region and the humanized $V_H$ domain of anti-lysozyme as a Hind III-Bam H1 fragment. These vectors are more fully described in Maeda, et al., *Hum. Antibod. Hybridomas* 2:124-134, (1991).

Since DNA fragments containing the native signal peptides were unavailable, the V regions of LO-CD2a were cloned behind the signals already present in the MRC vectors. The light chain V region with signal fragment was constructed from two fragments, each derived from a separate PCR reaction as follows:

Reaction 1: The DNA template was the MRC light chain vector. The fragment amplified contained the signal peptide plus a portion of framework (FR)1. The two oligonucleotides used were:

```
                      Hind III
5'VLlyssig (sense):   5' CCGCAAGCTTCATGGGATGGAG 3'        (SEQ ID NO:5)

TthIII
3'VLlyssig (antisense): 5' GCTGCTTGGGGACTGGGTCAGCTGGAT 3' (SEQ ID NO:6)
```

The antisense primer contained the FR 1 sequence of LO-Cd2a, not that found in the MRC vector for anti-lysozyme. The PCR reaction produced a 0.15 Kb Hind III - Tth III fragment.

Reaction 2: The DNA template was the LO-CD2a $V_L$ clone in Bluescript. The fragment amplified included LO-CD2a FR 1 (from the Tth III site) to the end of FR 4. The 3' untranslated region found in the MRC light chain vector was added to the 3' end of LO-CD2a using the antisense oligonucleotide. The 2 oligonucleotides used were: 5' $V_L$ LO-CD2a (sense):

```
                    Tth III
        5'ATTCAGCTGACCCAGTCTCCA 3'  (SEQ ID NO:7)

3'VL LO-CD2a (antisense):
                    BamHI
5'GATCGGATCCACCTGAGGAAGCAAAGTTTAAATTCTACTCACGTTTCAG
TTCCAGCTT 3'  (SEQ ID NO:8)
```

This reaction yielded a 0.35 Kb TthIII-Bam HI fragment. Both PCR products were gel purified using Qiaex and restricted with the appropriate enzymes. The Hind III-Tth III fragment plus the Tth III-Bam HI fragment then were ligated between the Hind III and Bam HI sites of Bluescript in a 3-way ligation. This construct, containing the entire $V_L$ region of LO-CD2a plus the MRC signal peptide was then sequenced.

The heavy chain LO-CD2a V region construct contains the MRC signal sequence at its 5' end and the long 3' untranslated region, also derived from the MRC H chain vector. The final construct was made from 3 separate PCR reactions as follows:

Reaction 1: The DNA template was the MRC H chain vector. Since $V_L$ and $V_H$ genes of anti-lysozyme use the same signal, the sense primer was the same as that used for the LO-CD2a $V_L$ construct, i.e., 5' $V_1$ lyssig. The antisense primer was 3'$V_H$lyssig:

```
              Pst 1
5'TCTCCTGCAGTGGGACCTCGGAGTGGACACC3'  (SEQ ID NO:9)
```

This reaction produced a 0.16 Kb Hind III-Pst I fragment containing the MRC signal plus a portion of FR 1 of LO-CD2a. The fragment was gel purified, restricted, and ligated into Hind III-Pst I cut Bluescript for sequencing.

Reaction 2: The DNA template was the LO-CD2a $V_H$ region in Bluescript. This reaction yielded a 0.3 Kb Pst I-Sty I fragment containing most of the $V_H$ region. Because there was an internal Pst 1 site in FR 3 of LO-CD2a, the Pst I-Sty I fragment had to be constructed from 2 PCR reactions as follows:

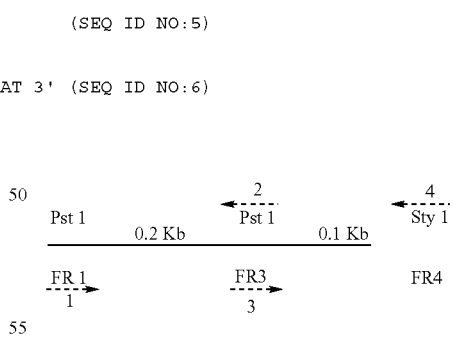

The template DNA shown above is clone 82-8, LO-CD2a $V_H$ in Bluescript.

Reaction A: Yields a 0.2 Kb fragment, using olignucleotides, also referred to as oligos 1 and 2, as primers:

Oligo 1 is: 5'Pst I 82-8 (sense):

```
             Pst I
5'GAGGTCCAGCTGCAGCAGTCT3'  (SEQ ID NO:10)
```

Oligo 2 is: 3'int. Pst I (antisense): 5'CGATGTATCAGCTGT-CAGTGTGGC3' (SEQ ID NO:11)

Reaction B: Yields a 0.1 Kb fragment, using oligos 3 and 4 as primers. Oligo 3 is 5'int. Pst I (sense):
5'GCCACACTGACAGCTGATACATCG3' (SEQ ID NO:12)

Oligo 4 is 3'Sty I 82-8 (antisense):

```
         Sty I
5'CAGAGTGCCTTGGCCCCAGTA3' (SEQ ID NO:13)
```

Oligos 2 and 3 above contain changes in nucleotide sequence which remove the internal Pst I site without changing the amino acid sequence of LO-CD2a. Aliquots (2-5 µl) of the overlapping products of reactions A & B above were combined and served as templates for a third PCR reaction. The oligonucleotide primers for this reaction were numbers 1 and 4 from the previous diagram. The 0.3 Kb product was gel purified by Qiaex and restricted with Pst I and Sty I. Since the fragment remained intact, the internal Pst 1 site had been successfully mutated.

Reaction 3: The final $V_H$ fragment was produced using the MRC heavy chain vector as template. This 0.23 Kb Sty I-Bam HI fragment contained a portion of FR4 of Lo-CD2a, and the entire 3' untranslated region from the MRC vector. The primers used were:

5'$V_H$lys Sty I (sense):

```
         Sty I
5'TACTGGGGCCAAGGCACCCTCGTCACA3' (SEQ ID NO:14)

3' V_Hlys Bam HI(antisense):     Bam HI
                      5'GATCGGATCCCTATAAATCTCTGGC3' (SEQ ID NO:15)
```

The resulting fragment was gel purified and restricted with Sty I and Bam HI. The Pst I-Sty I and Sty I-Bam HI fragments were then ligated into Pst I-Bam HI cut Bluescript for sequencing.

All oligonucleotides were synthesized on an Applied Biosystems synthesizer. All sequencing reactions were carried out using The Sequenase™ T7 Polymerase Kit (U.S. Biochemical, Cleveland, Ohio). All PCRs were carried out using the following protocol: 5 min. at 95° C., 35 cycles consisting of 1 min. at 94° C., 1 min. at 50° C., 2 min. at 72° C., a final extension of 5 min. at 72° C.

LO-CD2a $V_L$ and $V_H$ fragments containing the correct sequences were removed from Bluescript and cloned between the Hind III and Bam HI sites of the MRC light and heavy chain vectors, respectively. For the H chain, the 5' Hind III-Pst I fragment was first joined to the remainder of the construct (PstI-Bam HI) in Bluescript; the entire Hind III-Bam HI fragment was then cloned into the MRC vector.

C. N-Terminal Amino Acid Sequencing of $V_H$ and $V_L$

N-terminal amino acid sequence analysis was performed by Harvard Microchemistry Laboratory in Cambridge, Mass. on samples of LO-CD2a heavy and light chains in order to confirm the sequences obtained using RNA-PCR. The samples were prepared as follows:

200 ìg of LO-CD2a was applied across a 12% SDS polyacrylamide gel run in the presence of B-mercaptoethanol. Following electrophoresis, the protein was transferred to a PVDF membrane using a Western transfer apparatus. The membrane was stained briefly with Ponceau S, destained in 1% acetic acid, and the light and heavy chain bands were dried under vacuum and sent for amino acid analyses and N-terminal sequencing.

The amino acid sequence of the first 20 residues of LO-CD2a $V_H$ agreed completely with the cloned sequence; however, the sequence of $V_L$ indicated that residues 2, 3 and 7 in FR1 were different than those encoded by the cloned genes. These differences all reside in the PCR primer used for cloning purposes, based on a best guess sequence obtained from the previously cited literature.

D. DNA Sequence Confirmation of N-Terminal Amino Acid Sequence and its Correction In order to correct this sequence and simultaneously clone the native signal peptides of both $V_L$ and $V_H$ of LO-CD2a, RACE-PCR was employed was employed (Rapid Amplification of cDNA Ends): mRNA from LO-CD2a cells was reverse transcribed and the resulting cDNA was G-tailed at its 3' end using terminal transferase in the presence of dGTP. The cDNA was then amplified using a specific 3' oligonucleotide and a 5' oligonucleotide complementary to the G-tail. To simplify subcloning, a suitable restriction site was added to the 5' end of each oligonucleotide.

The oligonucleotides used for preparation of cDNA were as follows:

```
                              Bam H1 Not I    Sal I
3' oligo Vk(VKA)  (SEQ ID NO:16) TTGGATCCGCGGCCGCGTCGACTACAGTTGGTGCAGCATCAGC Bam H1 Not 1    Sal 1
3' oligo Vh(CHA)  (SEQ ID NO:17)  ATGGATCCGCGGCCGCGTCGACCCAGTGGATAGACCGATGG
```

The oligonucleotides for RACE-PCR were as follows:

```
                         Xho I
5' Primer (TV1):  5' CCA TGG CCT CGA GGG CCC CCC CCC CCC CCC C 3'  (SEQ ID NO:18)

Stu I
3' oligo Vh (BHA) 5' CCT GTT TAG GCC TCT GCT TCA CCC AGT AC 3'     (SEQ ID NO:19)

Sph I
3' oligo Vk (BKA) 5' GGA TAA TGG GTA AAT TGC ATG CAG TAA TA 3'     (SEQ ID NO:20)
```

RACE-PCR reactions were carried out using the following protocol: 5 min. at 94° C., 40 cycles of 30 sec. at 94° C., 30 sec. at 50° C., and 50 sec. at 72° C., followed by a 5 min. extension at 72° C.

PCR products obtained for LO-CD2a $V_L$ and $V_H$ were gel extracted using Qiaex. The $V_H$ fragment was restricted with Xho I and Stu I and ligated into Xho I-Sma I cut Bluescript. The $V_L$ fragment was blunt-ended and ligated into Sma I cut Bluescript. A number of clones were sequenced for both light and heavy chain V regions and the signal sequences were identified.

Since signal sequences found in immunoglobulin genes generally have introns, these may be important for expression. Genomic clones containing the $V_L$ and $V_H$ leader sequences were identified as well. Genomic DNA was prepared as follows: 4×10$^7$ LO-CD2a cells were spun down, washed in cold PBS, spun down, and washed with PBS again. Cells were resuspended in 0.4 ml digestion buffer (with freshly added proteinase K). This mixture was incubated with shaking at 50° C. for 12-15 hours, extracted with an equal volume of phenol/chloroform/isoamyl alcohol, and spun at 1700×g. The aqueous phase was transferred to a clean tube and ½ volume of 7.5 M ammonium acetate and 2 volumes of 95% ethanol were added. The DNA was pelleted by spinning 2 minutes, 1700×g. The pellet was washed with 70% ethanol and air dried. The pellet was resuspended in 80 ml TE, pH 8.0.

Using genomic DNA obtained from the cell line LO-CD2a as a template, the following oligonucleotides were designated in order to amplify the genomic leader sequences of both $V_L$ and $V_H$ as well as portions of the framework regions ending at unique restriction sites (Sph I for $V_L$, Pst I for $V_H$).

LVL #430 TGC AAGCTTCATGATGAGTCCTGTCCAGTC (SEQ ID NO:21)

Leader $V_L$ sense/Hind III

LVH #429 AGTAAGCTTCATGAAATGCAGGTGGATC (SEQ ID NO: 22)

Leader $V_H$ sense/Hind III

PVHA # 428 GGGAGATTGCTGCAGCTGGACTTC (SEQ ID NO:23)

$V_H$ antisense/Pst I

PCR reactions were carried out as follows: 100 ng genomic DNA from LO-CD2a cells, 200 pmol each of oligos LVL and BKA (for $V_L$ fragment) or 200 pmol each of LVH and PVHA (for $V_H$ fragment), 10 ìl mm dNTPs, 10 ìl 10×Pfu buffer. 1 ìl (2.5 units) Pfu DNA polymerase (stratagene, La Jolla, Calif.) deionized water to 100 ìl. Pfu was used because of its greater accuracy than Taq polymerase.

The reaction conditions were as follows: 5 min. 94° C., 5 min. 50° C., 35 cycles of 1 min. 94° C., 1 min. 50° C., 1 min. 72° C., followed by 5 min. at 72° C. The PCR products were gel purified, restricted and ligated into Bluescript for sequencing. Once clones containing the correct sequence were identified, Bluescript vectors containing these clones were cut with Hind III and Sph I ($V_L$) or Hind III and Pst I ($V_H$) and the fragments were gel isolated. The 0.75 Kb Hind III-Sph I fragment was then ligated into Bluescript containing the original LO-CD2a $V_L$ construct from which the Hind III-Sph I fragment had been removed. The new construct contained the native LO-CD2a signal plus intron and a corrected FR1 sequence (in agreement with the N-terminal sequence). The 0.16 Kb Hind III-Pst I fragment was ligated into Bluescript containing the original LO-CD2a $V_H$ construct from which the Hind III-Pst I fragment had been removed. The new construct contained the native signal+intron. The newly constructed $V_L$ and $V_H$ fragments were then removed from Bluescript by digestion with Hind III and Bam HI and cloned into the MRC light and heavy chain vectors, respectively, for expression in COS cells.

E. Transient expression in COS cells. COS 7 cells were obtained from the ATCC (Accession No. CRL-1651) and were grown in Dulbecco's Minimal Essential Medium (DMEM) with 10% fetal bovine serum (FBS). Optimal transfection was achieved at approximately 50% confluency of adherent cells. In preparation for transfection, plasmid DNA was added to DMEM containing NuSerum and DEAE-Dextran/chloroquine diphosphate. COS cell medium was removed, the DNA mixture was added and the cells incubated for 3 hours at 37° C. This medium then was removed, and 10% DMSO in PBS was added to the cells for 2 minutes and then removed. DMEM with 10% FBS was added to the cells. After overnight incubation, the medium was replaced and the cells were incubated for 2 days at 37° C. Supernatants were collected for assay by ELISA for the secretion of chimeric antibody.

F. Detection of secreted chimeric antibody by ELISA. Secretion of chimeric antibody was confirmed by assay of supernatants from the transfected COS cells in an ELISA designed to detect the presence of human antibody (or a portion thereof). Goat anti-human IgG (H+ L) was diluted in phosphate buffered saline (PBS) to a concentration of 5 ìg/ml and bound to the wells of ELISA microtiter plates by overnight incubation at 4° C. Plates were washed 3 times using an ELISA plate washer.

Remaining free sites were blocked by the addition of 200 il PBS containing 1% bovine serum albumin (PBS-BSA) for ½ hr. at room temperature. Two-fold dilutions were prepared in PBS-BSA of the supernatants and of a positive control reference standard (purified human IgG1k). Media alone and/or PBS-BSA alone constituted negative controls. Antibody dilutions and controls were added to the wells and incubated at room temperature for 1½ hours. Plates were then washed 3 times with a plate washer in PBS containing 0.05% Tween20. The appropriate dilution of a goat anti-human IgG (gamma chain specific)-horseradish peroxidase (HRP) conjugated antibody or goat anti-human kappa light chain -HRP conjugated antibody was added to each well and incubated at room temperature for 1 hour. Plates were washed with PBS-Tween20 as described above, after which the developing substrate, (ABTS) containing hydrogen peroxide, was added. Bound antibody was detected by reading absorbance at a wavelength of 405 nm.

G. Binding specificity of secreted chimeric antibody. Binding specificity of the chimeric antibody was evaluated by flow cytometric analysis of antibody binding to the CD2– expressing mutant Jurkat cell line JRT3-T3-5. The binding profile of the chimeric antibody (human IgG1) was compared with those of the native rat antibody (IgG2b) and the isotype-matched control MABs (human IgG1 and rat IgG2b) which exhibit irrelevant (non-CD-2) binding specificities.

Preparation of JRT3-T3-5 (Jurkat) cell line. The Jurkat cell line was obtained from the ATCC (Accession No. TIB-153) and was propagated in D-MEM containing 10% fetal bovine serum (FBS), 10% amino acid supplement (NCTC), and 6 mM L-glutamine (complete medium). The cells were maintained at 37° C. with 10% $CO_2$ and were passaged three times per week at a ratio of 1:4 (the cell concentration at passage being approximately $3 \times 10^6$/ml). Jurkat cells were harvested, centrifuged to remove spent medium, and washed in DMEM. The cells were then resuspended in phosphate buffered saline (PBS) with 0.1% sodium azide (NaAz), and an aliquot was removed for cell quantification. The number of viable cells was determined by trypan blue exclusion.

Indirect staining of Jurkat cells. Cell surface staining was carried out in a 96 well U-bottom microtiter plate. Approximately $6 \times 10^5$ cells in a volume of 90 il were distributed into each well of the microtiter plate. Dilutions of the antibodies to be tested were prepared in PBS with 0.1% NaAz and distributed into the appropriate wells in a volume of 10 il. Cells were incubated with antibody for 15 minutes at room temperature, after which the cells were washed 3 times by adding PBS with 0.1% NaAz to each well and by centrifuging for 2 minutes at 1900 rpm (Sorvall RT6000D). Resuspension of cells was accomplished by gently tapping the plates. Ten ul aliquots of the appropriate fluorescein-isothiocyanate (FITC)-conjugated secondary antibody (anti-human Ig or anti-rat Ig) was added to the appropriate wells and incubated at room temperature for 15 minutes in the dark. Plates were washed 3 times in PBS with 0.1% NaAz as described above. Stained cells were fixed by the addition of 200 il of 0.5% paraformaldehyde in PBS and were stored at 4° C. (up to 1 week).

Flow cytometric analysis of stained Jurkat cells. Stained cells were transferred to 12×17 mm polystyrene tubes for acquisition of data using a Becton-Dickinson FACScan. Data acquisition and analysis were carried out using LYSIS-II software. CD2– expressing Jurkat cells were incubated with the LO CD2a (rat IgG2b)MAB, the chimeric version of LO-CD2a (human IgG1), and the corresponding isotype matched controls. Bound antibody was detected using the appropriate FITC-conjugated secondary antibody according to the protocol described above. Analysis shows similar binding patterns of the native rat LO CD2a and the chimeric human-rat LO-CD2a.

H. Stable Expression in NSO Cells

In order to express the chimeric antibody in a stable transfectant, the glutamine synthetase gene amplification system was obtained from Celltech Limited (Berkshire, UK). This system is described in Bebbington, et al., *Biotechnology*, Vol. 10, pgs. 169-175 (1992). The expression vectors used were pEE6hCMV-B and pEE12. Such vectors are described in published PCT Application Nos. WO86/05807, WO87/04462, WO89/01036, and WO89/10404. Since neither of these vectors contains C kappa or C gamma 1, genomic clones for these genes were obtained from the MRC light and heavy chain vectors, respectively. Both constant region clones were sequenced in order to obtain restriction maps. Two constructs were made in pEE12: the first contained the light chain (V+C) 5' to the heavy chain (V+C); the second construct contained the heavy chain 5' to the light chain.

The strategy involving the light chain was as follows:
1. pEE6hCMV-B and pEE12 each were digested with Xma I and Eco RI.
2. The 5' 1.93 Kb portion of the chimeric light chain was removed from the MRC vector using HindIII and Eco RI. This fragment was used as a template for PCR mutagenesis as follows:

PCR oligos
LC 5' Xma 1:
5'-GATC CCCGGGCCACCATGATGAGTCCTGTCCAG-3' (SEQ ID NO:24)
LC 3' Msc 1:
5'-AGAA TGGCCACGTCATCCGACCCCCTCAGAGTTTACT ATTCTACTATCCAACTGAGGAAGC-3' (SEQ ID NO: 25)

The restriction sites are underlined.

The PCR was performed in order to change the 5' restriction site from HindIII to Xma I and to add a Kozak consensus sequence at the 5' end of the construct. This is essential for efficient translation (Kozak, M. *J. Cell. Biol.* 108: 229, 1989). The 3' PCR oligo is used to remove internal Bam HI and Eco RI sites which would interfere with subsequent cloning steps. The final product of the PCR mutagenesis is an 0.85 Kb Xma I-Msc I fragment. PCRs were carried out following instructions supplied with the TA cloning kit (Invitrogen, San Diego, Calif.). The following conditions were used for PCR: 2 min. at 94° C. followed by 30 cycles of 1 min. at 94° C., 2 min. at 55° C. and 2 min. at 72° C. This was followed by a 5 min. extension at 72° C. Ligations and transformations were carried out according to kit instructions. A number of clones were sequenced by the dideoxy chain termination method, as described previously. A correct clone was removed from the TA cloning vector by digestion with Xma I and Msc I. This fragment was gel purified using Qiaex.

3. The 2.7 Kb C kappa fragment was removed from the MRC vector by digestion with Msc I and Eco RI. The fragment was gel purified using Qiaex.

Using two separate 3-way ligations, the entire chimeric light chain, i.e., 0.85 Kb Xma I/Msc I fragment+2.7 Kb Msc I/Eco RI fragment was ligated into both pEE6hCMV-B and pEE12, each of which were cut with Xma I/Eco RI.

The strategy involving the heavy chain was as follows:
1. Both pEE6hCMV-B and pEE12 were transfected into the *E. coli* strain DM1. Both vectors were digested with Eco RI and BclI (BclI will only cut if plasmids are propagated in methylase minus bacteria).
2. The chimeric heavy chain was removed from the MRC vector by digestion with HindIII and Eco RI. The resultant 2.7

Kb fragment was gel purified using Qiaex. This fragment was digested with Nhe I and Bgl II. This produces a 0.7 Kb HindIII/Nhe I fragment and a 2 Kb Nhe I/Bgl II fragment. Both fragments were gel purified. The 0.7 Kb fragment was then used as a template for PCR mutagenesis.

PCR oligos

HC 5' Eco RI:

5'-GATC GAATTCGCCACCATGAAATGCAGGTGGATC-3' (SEQ ID NO:26)

HC 3' Nhe 1:

5'-CCAGAAA GCTAGCTTGCCATCCCTATAAATCTCTGGC-3' (SEQ ID NO:27)

The restriction sites are underlined.

This PCR is performed in order to change the 5' restriction site from HindIII to Eco RI and to add a Kozak consensus sequence. The 3' oligo is used to remove an internal Bam HI site which would interfere with subsequent cloning steps. PCRs, ligations and transformations were carried out as described previously.

Using two separate 3-way ligations, the entire chimeric heavy chain, i.e. 0.7 Kb Eco RI/Nhe I fragment+2.0 Kb Nhe I/Bgl II fragment was ligated into both pEE6hCMV-B and pEE12, each cut with Eco RI/Bcl I.

(Bcl I and Bgl II are Compatible Restriction Sites.)

Final constructs in pEE12, containing both the chimeric light and heavy chains were made as follows:

Light chain 5' to heavy chain: pEE6hCMV-B, which is carrying the chimeric heavy chain, was digested with Bgl II/Bam HI. The 5.1 Kb fragment containing the heavy chain plus the hCMV promoter, was gel purified and ligated into the Bam HI site of pEE12 which contains the chimeric light chain. Correct orientation was checked by digestion with Sal I/Bam HI. The presence of a 0.28 Kb fragment indicates correct orientation.

Heavy Chain 5' to light chain: pEE6hCMV-B, which is carrying the chimeric light chain, was digested with Bgl II/Bam HI. The 5.9 Kb fragment which contains the light chain plus the hCMV promoter was gel purified and ligated into the Bam HI site of pEE12 which contains the chimeric heavy chain. Orientation was checked by digestion with Sal I/Bam HI, as indicated above.

NS/O cells (Galfre, et al., Meth. in Enzymol., Vol. 73(B) pgs. 3-46 (1981), and deposited with the European Collection of Animal Cell Cultures as ECACC Catalog No. 85110503. were transfected by electroporation. Transfected cells were selected by growth in glutamine-free medium. Antibody production and binding activity on CD2–expressing Jurkat cells were confirmed as described above.

Functional analysis of the human-rat chimeric antibody shows that its functional properties are similar to those of the rat LO-CD2a antibody. Both inhibit a primary mixed leukocyte reaction (MLR) when nanogram quantities of antibody up to 120 ng/ml are added to the culture. Furthermore, addition of the chimeric antibody to a primary MLR induces a state of hyporesponsiveness in the responder population to challenge with the original alloantigen or with a third party alloantigen. The hyporesponsiveness is alloantigen-specific in that challenge with mitogen or tetanus toxoid elicits a proliferative response.

EXAMPLE 7

Construction and Expression of Humanized Antibody

A. Construction of Humanized Light Chain

The framework regions from a human V kappa gene designated as HUM5400 (EMBL accession X55400), which shares homology with LO-CD2a, were chosen for humanization of the light chain V region. Below is a comparison between the frameworks of LO-CD2a and HUM5400:

```
Framework 1

*       *
LO-CD2a:  D V V L T Q T P P T L L A T I G Q S V S I S C (SEQ ID NO:28)

HUM5400:  - - - M - - S - L S - P V - L - - P A - - - - (SEQ ID NO:29)

Framework 2

* *               * *
LO-CD2a:     W L L Q R T G Q S P Q P L I Y (SEQ ID NO:30)

HUM5400:     - F Q - - P - - - - R R - - - (SEQ ID NO:31)

Framework 3

*
LO-CD2a:     G V P N R F S G S G S G T D F T L K I S G V E A E
           D L G V Y Y C (SEQ ID NO:32)

HUM5400:     - - - D - - - - - - - - - - - - - - - R - - - -
           - V - - - - - (SEQ ID NO:33)

Framework 4

LO-CD2a:     F G A G T K L E L K (SEQ ID NO:34)

HUM5400:     - - Q - - - - - I - (SEQ ID NO:35)
```

A comparison of the light chain variable region sequences of the rat LO-CD2a, the homologous human variable region, HUM5400, and humanized LO-CD2a is shown in FIG. 31. The complete amino acid sequence is given for the LO-CD2a variable region and residues are numbered according to the rat sequence. Residues identical to those of the rat in the corresponding positions in the humanized and HUM5400 sequences are indicated by horizontal dashed lines, whereas non-identical residues are given by letter code. The humanized LO-CD2a light chain variable region is comprised of the HUM5400 framework regions, the rat LO-CD2a CDR's (underlined), and seven rat LO-CD2a framework residues (designated by an * above the rat sequence) which were selected because such residues may be relevant for maintaining the binding specificity of LO-CD2a.

Figure 32:
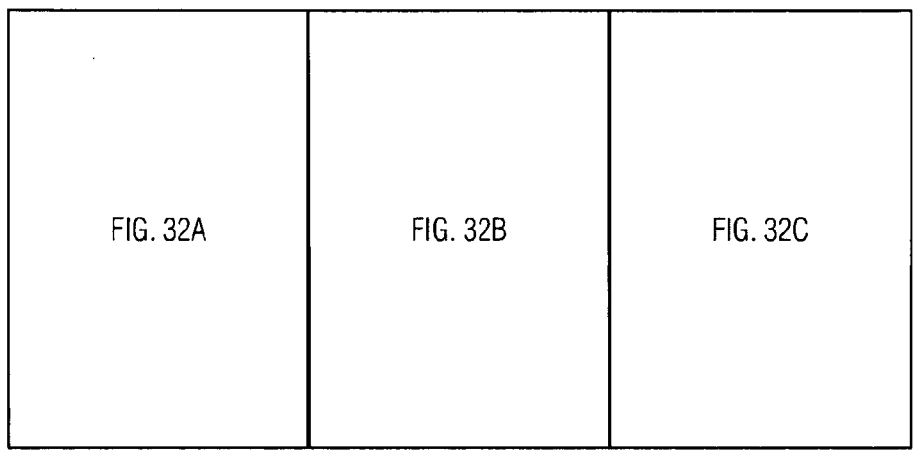

As shown in FIG. 31, Framework 1 is from amino acid residues 1 to 23. CDR1 is from amino acid residues 24 to 39. Framework 2 is from amino acid residues 40 to 54. CDR2 is from amino acid residues 55 to 61. Framework 3 is from amino acid residues 62 to 93. CDR3 is from amino acid residues 94 to 102. Framework 4 is from amino acid residues 103 to 112. The leader sequence is from amino acid residues -20 to -1. (FIG. 32). The rat amino acid residues which are retained in the framework regions are amino acid residues 9 and 12 in Framework 1; amino acid residues 41, 42, 50, and 51 in Framework 2; and amino acid residue 82 in Framework 3.

A humanized light chain was constructed which contains the CDRs of LO-CD2a and the variable region frameworks of HUM5400 except for 7 unusual residues (*) which were retained from the frameworks of LO-CD2a. The 5' region was taken from the chimeric light chain construct. This 0.43 Kb Hind III/Hph I fragment contains the native signal plus intron and the sequence encoding the first 3 amino acid residues of framework 1 which are identical in the rat and human frameworks. The remainder (i.e., the 3' end) of the construct (0.37 Kb), containing the nucleotides encoding all but the first three amino acids of the variable region, was synthesized by PCR from 7 overlapping oligonucleotides, ranging in size from 63-81 nucleotides. These long oligonucleotides served as templates for shorter 5' and 3' outside PCR oligonucleotides (21-26 nucleotides in length). In all cases, 5 pmol of template was used along with 100 pmol of each outside PCR oligonucleotide. All PCRs were carried out using Pfu polymerase in order to achieve greater fidelity. The procedure was as follows: 5 min at 95° C., followed by 25 cycles which included 2 min at 94° C., 2 min at 55° C. and 2 min at 72° C. This was followed by an additional 5 min extension at 72° C. The entire synthesis was accomplished in 4 steps. In the first step, the first long oligonucleotide was added on to the 0.43 Kb Hind III-Hph I fragment. The next 3 sets of overlapping oligonucleotides were then added sequentially using PCR. After synthesis of the entire 0.8 Kb construct was completed, it was gel purified using Qiaex, restricted with Hind III and Bam HI, gel purified again with Qiaex, and ligated to Hind III/Bam HI cut Bluescript KS II. A number of clones were sequenced until a correct version was obtained. The clone was then removed from Bluescript by digestion with Hind III and Bam HI. The resultant fragment was gel purified using Qiaex and ligated into the MRC light chain vector which had been cut with Hind III/Bam HI. The nucleotide and amino acid sequences of the humanized LO-CD2a light chain V region are shown in FIG. 32.

The overlapping oligonucleotides used in the synthesis of the humanized light chain and a description of their use follows:

Oligonucleotide #1 (SEQ ID NO:36):

5'GCAAGAGATGGAAGCTGGTTGTCCCAAG-GTTACCAATAATGAAGGTGGACTCTGGGTCATCAC AACATCACCATTGGTTCC3'

Oligonucleotide #2 (SEQ ID NO:37):

5'CAACCAGCTTCCATCTCTTGCAGGT-CAAGTCAGAGTCTCTTACATAGTAGTG-GAAACACCTAT TTAAATTGG3'

Oligonucleotide #3 (SEQ ID NO:38):

5'AGATTCCAGTTTGGATACCAAATAAATT-AGCGGCTGTGGAGATTGGCCTGGCCTTAGCAACCA ATTTAAATAGGTGTTTCC3'

Oligonucleotide #4 (SEQ ID NO:39):

5'TTGGTATCCAAACTGGAATCTGGGGTC-CCCGACAGGTTCAGTGGCTCAGGGAGTG-GAACAGAT TTCACACTCAAAATCAGT3'

Oligonucleotide #5 (SEQ ID NO:40):

5'ATGGGTAAATTGCATGCAGTAATAAAC-CCCCACATCCTCAGCTTCCACTCCACTGATTTTGAG TGTGAAATC3'

Oligonucleotide #6 (SEQ ID NO:41):

5'TACTGCATGCAATTTACCCATTATCCG-TACACGTTTGGACAAGGGACCAAGCTG-GAAATCAAA 3'

Oligonucleotide #7 (SEQ ID NO:42):

5'GATCGGATCCAACTGAGGAAGCAAAGTT-TAAATTCTACTCACGTTTGATTTCCAGCTTGGTCC CTTG3'

Oligonucleotides 1, 3, 5, and 7 are inverse complementary sequences.

Oligonucleotides 2, 4, and 6 are sense strand sequences.

Oligonucleotide #1 overlaps the 0.43 Kb Hind III/Hph I fragment derived from the chimeric light chain construct. This oligonucleotide was added to the 0.43 Kb fragment by PCR, using the following PCR oligos:

(5') PCR 1A (sense): 5'GATCAAGCTTCATGAT-GAGTCCT3' (SEQ ID NO:43)

(3') PCR 1A' (inverse complement): 5'GCAAGAGATG-GAAGCTGGTTG3' (SEQ ID NO:44)

In a similar manner, oligonucleotides #2 and #3 were stitched together by PCR using the following PCR oligos:

5' PCR 2B (sense): 5'CAACCAGCTTCCATCTCTTGC3' (SEQ ID NO:45)

3' PCR 2B' (inverse complement): 5'AGATTCCAGTTTG-GATACCAA3'. (SEQ ID NO:46)

After PCR, both products were gel purified using Qiaex, and then joined together using a third PCR. The third PCR required the following oligos:

(5') PCR 1A (3') PCR 2B'.

The resultant fragment was gel purified by Qiaex. Oligonucleotides #4 and #5 were then joined together by PCR using the following oligos:

(5') PCR 3C (sense): 5'TTGGTATCCAAACTG-GAATCTGGG3' (SEQ ID NO:47)

(3') PCR 3C' (inverse complement):5'ATGGGTAAATTG-CATGCAGTAATA3' (SEQ ID NO:48)

The fragment was gel purified and added to the previous construct using PCR oligos:

(5') PCR 1A (3') PCR 3C'.

The final piece was constructed using oligonucleotides #6 and #7 and PCR oligos:

(5') PCR 4D (sense): 5'TACTGCATGCAATTTACCCAT-TAT3' (SEQ ID NO:49)

(3') PCR 4D' (inverse complement): 5'GATCGGATCCAACTGAGGAAGCAAAG3' (SEQ ID NO:50)

After gel purification, this fragment was added to the remainder of the humanized light chain construct by PCR using oligos:
(5') PCR 1A
(3') PCR 4D'.

B. Construction of the Humanized Heavy Chain

The framework regions of the human antibody clone Amu 5-3 (GenBank accession number U00562) were used for the generation of the humanized heavy chain. Below is a comparison between the frameworks of LO-CD2a and those of Amu 5-3:

```
Framework 1

LO-CD2a (SEQ ID NO:51):  E V Q L Q Q S G P E L Q R P G A S V K L
                         S C K A S G Y I F T

Amu 5-3 (SEQ ID NO:52):  Q - - - V - - - A - V K K - - - - - - V
                         - - - - - - - T - -

Framework 2
                                     *
LO-CD2a (SEQ ID NO:53):  W V K Q R P K Q G L E L V G Amu 5-3 (SEQ ID NO:54):  - - R - A - G - - - - W M -

Framework 3

*   *   *       *               *
LO-CD2a (SEQ ID NO:55):  K A T L T A D T S S N T A Y M Q L S S L
                         *
                         T S E D T A T Y F C A R

Amu 5-3 (SEQ ID NO:56):  R V - M - R - - - I S - - - - E - - R -
                         R - D - - V - Y - - - -

Framework 4

LO-CD2a (SEQ ID NO:57):  W G Q G T L V T V S S

Amu 5-3 (SEQ ID NO:58):  - - - - - - - - - - -
```

FIG. 33 shows the heavy chain variable region sequences of the rat LO-CD2a, the homologous human variable region, Amu5-3, and the humanized LO-CD2a (humanized Vh). The complete amino acid sequence is given for LO-CD2a and residues are numbered according to the rat sequence. Residues identical to those of the rat in the corresponding positions in the humanized and Amu5-3 sequences are indicated by horizontal dashed lines whereas non-identical residues are given by letter code. The humanized LO-CD2a Vh is comprised of the Amu5-3 framework regions, the rat LO-CD2a CDRs, and seven rat LO-CD2a framework residues (designated by an * above the rat residue) which were selected because they may be relevant for maintaining the binding specificity of LO-CD2a. The vertical lines in CDR3 of the rat and humanized sequences represent spaces which were required to align the three sequences because the Amu5-3 has a longer CDR3 than the rat and humanized regions.

Figure 34:
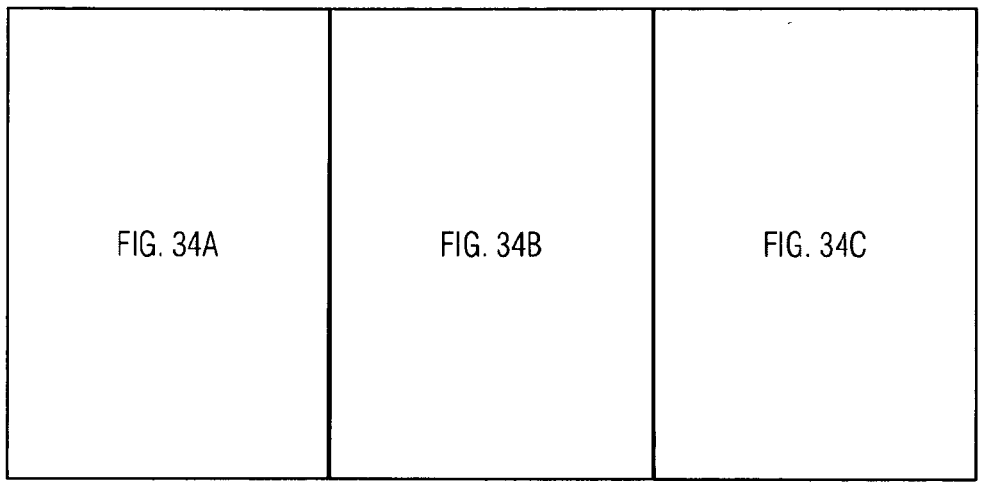

As shown in FIG. 33, Framework 1 is amino acid residues 1 to 30. CDR1 is amino acid residues 31 to 35. Framework 2 is amino acid residues 36 to 49. CDR2 is amino acid residues 50 to 66. Framework 3 is amino acid residues 67 to 98. CDR3 is amino acid residues 99 to 107. Framework 4 is amino acid residues 108 to 118. The leader sequence is amino acid residues -19 to -1. (FIG. 34).

The rat LO-CD2a amino acid residues which are retained in the framework regions are amino acid residue 47 in Framework 2; and amino acid residues 67, 70, 72, 76, 85 and 87 in Framework 3.

A single humanized heavy chain construct was made. This construct contains the CDRs of LO-CD2a and the frameworks of Amu 5-3, with the exception of 7 residues (*) retained from LO-CD2a. This construct was produced in a manner similar to that of the humanized light chain. In this case, there were 12 overlapping template oligonucleotides, ranging in size from 69-88 nucleotides. The 12 outside PCR oligonucleotides ranged in size from 21-26. The synthesis was accomplished in 6 steps, adding on a pair of overlapping template oligonucleotides at each step. The final construct (0.7 Kb) was gel purified using Qiaex, digested with Hind III and Bam HI, gel purified again, and ligated into Bluescript for sequencing, as described previously. When a correct clone was identified, it was removed from Bluescript by restriction with Hind III/Bam HI, and then ligated into the MRC heavy chain vector which had been digested with the same enzymes. The nucleotide and amino acid sequences of the humanized LO-CD2a heavy chain V region is shown in FIG. 34.

The overlapping oligonucleotides used in the synthesis of the humanized heavy chain and a description of their use follows:

Oligonucleotide #1 (SEQ ID NO:59) (sense):

5'GATC AAGCTTCATGAAATGCAGGTGGATCATCCTCTTC TTGATGGCAGTAGCTACAGGTAAGG CACTC- CCAAGTCCTAAACTTGAGAG3' (Hind III site underlined)

Oligonucleotide #2 (SEQ ID NO:60) (antisense):

5'CACCTGTGAGTTGACCCCTGTTGAAA- GAAATCCAAAGATAGTGTCACTGTCTC- CCAAGTGTAT GATCTCTCAAGTTTAGGACTTGGG3'

Oligonucleotide #3 (SEQ ID NO:61) (sense):

5'ACAGGGGTCAACTCACAGGTGCAGCTG- GTGCAGTCTGGGGCTGAGGTGAAGAAGC- CTGGGGCC TCAGTGAAGGTCTCC3'

Oligonucleotide #4 (SEQ ID NO:62) (antisense):

5'GGCCTGTCGCACCCAGTACATATAG-TACTCGGTGAAGGTGTATCCAGAAGCCT-TGCAGGAGAC CTTCACTGAGGCCCC3'

Oligonucleotide #5 (SEQ ID NO:63) (sense):

5'ATGTACTGGGTGCGACAGGCCCCTGGA-CAAGGGCTTGAGCTGATGGGAAGGATC-GATCCTGAA GACGGTAGTATTGAT3'

Oligonucleotide #6 (SEQ ID NO:64) (antisense):

5'TGTGCTAGAGGACGTGTCAGCGGT-CAGGGTGACCTTTTTCTTAAACTTCT-CAACATAATCAAT ACTACCGTCTTCAGG3'

Oligonucleotide #7 (SEQ ID NO:65) (sense):

5'GCTGACACGTCCTCTAGCACAGCCTA-CATGGAGCTGAGCAGCCTGACCTCTGAC-GACACGGCC GTGTATTACTGTGCGAGAGGA3'

Oligonucleotide #8 (SEQ ID NO:66) (antisense):

5'GGACTCACCTGAGGAGACGGTGAC-CAGGGTTCCTTGGCCCCAGTAAGCAAAC-CTATAGTTAAA CTTTCCTCTCGCACAGTAATACAC3'

Oligonucleotide #9 (SEQ ID NO:67) (sense):

5'ACCGTCTCCTCAGGTGAGTCCTTACAAC-CTCTCTCTTCTATTCAGCTTAAATAGATTTTACTG CATTTG3'

Oligonucleotide #10 (SEQ ID NO:68) (antisense):

5'CCTAGTCCTTCATGACCTGAAATTCA-GATACACACATTTCCCCCCCAACAAATG-CAGTAAAAT CTATTT3'

Oligonucleotide #11 (SEQ ID NO:69) (sense):

5'TTCAGGTCATGAAGGACTAGGGACACCT-TGGGAGTCAGAAAGGGTCATTGGGAGC-CCGGGCTG ATGCAGACA3'

Oligonucleotide #12 (SEQ ID NO:70) (antisense):

5'GATCGGATCCCTATAAATCTCTGGCCAT-GAAGTCTGGGAGCTGAGGATGTCTGTCTGCATCAG CCCGGGCTC3'

Overlapping oligonucleotides #1 and #2 were joined together by PCR using the following PCR oligos:

(5') PCR 4H (sense): 5'GATCAAGCTTCATGAAATG-CAGGTG3'(SEQ ID NO:71)

(3') PCR 4H' (antisense): 5'CACCTGTGAGTTGAC-CCCTGTTG3' (SEQ ID NO:72)

The resulting fragment was gel purified.

Overlapping oligonucleotides #3 and #4 were joined together by PCR using the following PCR oligos:

(5') PCR 1E (sense): 5'ACAGGGGTCAACTCACAG-GTG3'(SEQ ID NO:73)

(3') PCR 1E' (antisense): 5'GGCCTGTCGCACCCAGTA-CAT3'. (SEQ ID NO:74)

The fragment was gel purified.

Oligonucleotides #5 and #6 were joined together by PCR using the following PCR oligos:

(5') PCR 2F (sense): 5'ATGTACTGGGTGCGACAG-GCC3'(SEQ ID NO:75)

(31) PCR 2F' (antisense): 5'TGTGCTAGAGGACGTGT-CAGC3'. (SEQ ID NO:76)

After gel purification, this fragment was joined to the fragment produced by oligonucleotides #3 and #4 by PCR with the following oligos:

(5') PCR 1E (sense)

(3') PCR 2F' (antisense).

The resultant fragment was gel purified.

Oligonucleotides #7 and #8 were joined together by PCR using the following PCR oligos:

(5') PCR 3G (sense): 5'GCTGACACGTCCTCTAG-CACA3'(SEQ ID NO:77)

(3') PCR 3G' (antisense): 5'GGACTCACCTGAG-GAGACGGT3'. (SEQ ID NO:78)

The resultant fragment was gel purified and added to the construct made by joining oligonucleotides #3 through #6. This was achieved using PCR oligos.

(5') PCR 1E (sense)

(3') PCR 3G' (antisense).

The resultant fragment, made by joining oligonucleotides #3 through #8, was gel purified. The 5' end of the construct (oligonucleotides #1+#2) was then added using PCR oligos.

(5') PCR 4H (sense)

(3') PCR 3G'.

This fragment was gel purified and the next piece (3') was added using oligonucleotides #9 and #10.

Oligonucleotides #9 and #10 were joined by PCR using the following PCR oligos:

(5') PCR 5I (sense): 5'ACCGTCTCCTCAGGT-GAGTCC3' (SEQ ID NO:79)

(3') PCR 5I' (antisense): 5'CCTAGTCCTTCATGACCT-GAA3'. (SEQ ID NO:80)

After gel purification, this 3' piece was added to the remainder of the construct using PCR oligos.

(5') PCR 4H (sense)

(3') PCR 5I' (antisense).

The resultant fragment was gel purified and joined to the remainder of the construct.

Oligonucleotides #11 and #12 were joined by PCR using the following PCR oligos:

(5') PCR 6J (sense): 5'TTCAGGTCATGAACGAC-TAGG3' (SEQ ID NO:81) and (3') PCR 6J'(antisense): 5'GATCGGATC-CCTATAAATCTCTGGCC3' (SEQ ID NO:82)

After gel purification, this final 3' fragment was added to the rest of the construct using oligos (5') PCR4H (sense) and (3') PCR6J' (antisense). The resultant 0.7 kb final construct was gel purified, sequenced, and cloned into the MRC heavy chain vector, as indicated previously.

Figure 35:
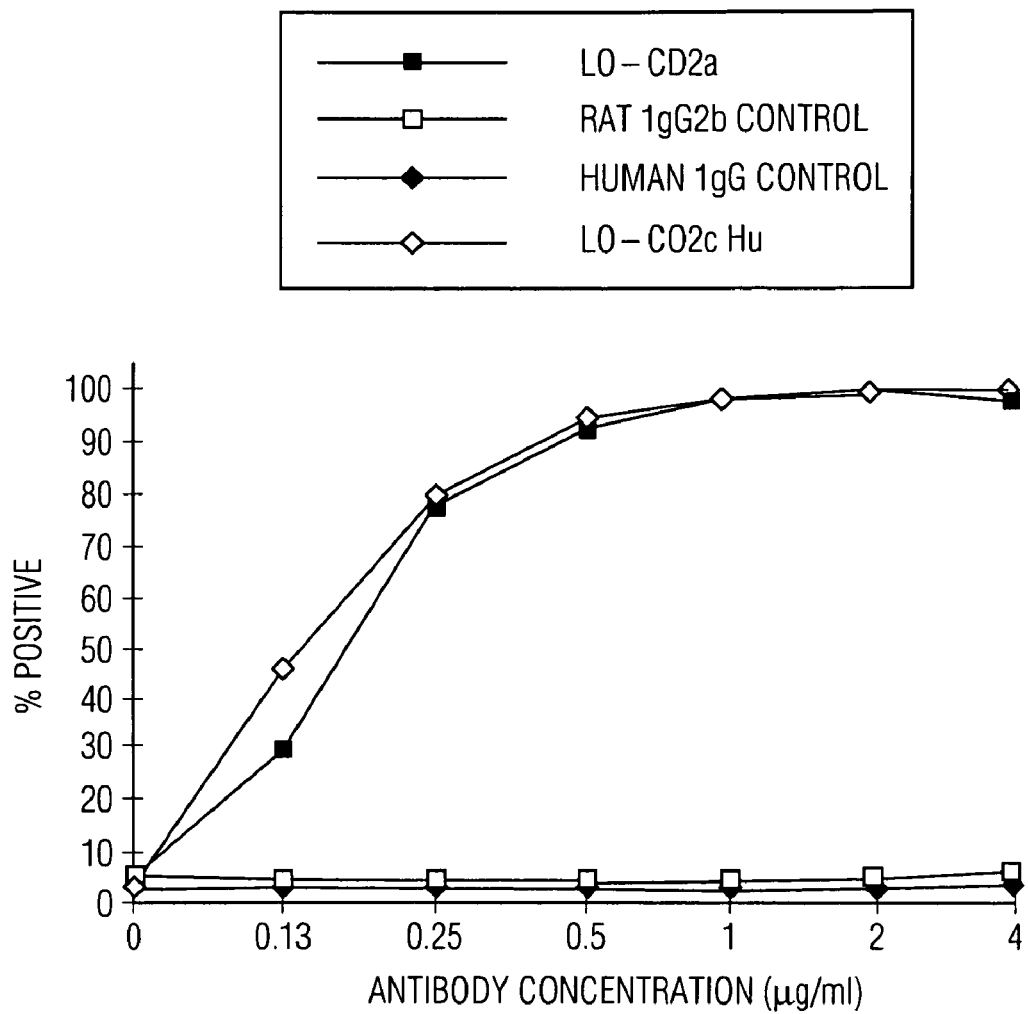

Transient expression in COS cells and detection of secreted antibody were carried out as described previously for the chimeric antibody. The humanized antibody was purified by affinity chromatography (Protein A). Binding studies on Jurkat cells demonstrate similar binding patterns between the humanized and rat forms of LO-CD2a (FIG. 35). The Jurkat cell line, which expresses CD2, was stained with rat LO-CD2a, the humanized LO-CD2a (LO-CD2aHu), or rat IgG2b or human IgG controls. Antibody concentrations ranged from 0 to 4 ig/ml. The rat and humanized forms of LO-CD2a bind to Jurkat cells with similar binding patterns, whereas the rat and human isotype control antibodies do not. Bound antibodies were detected with an isotype-specific FITC-conjugated antisera. The results shown in FIG. 35 are expressed as the percentage of cells positively stained by the antibodies over the range of concentrations mentioned hereinabove. Functional studies indicate that the humanized antibody is also capable of inhibiting a primary MLR. Nanogram quantities of LO-CD2a, LO-CD2aHu, rat IgG2b control, or human IgG1 control were added to culture wells containing equivalent numbers of human peripheral blood mononuclear cells (PBMC) from a designated responder and stimulator (irradiated cells). Control wells contained no antibody. The cultures were incubated for 5 days, then pulsed overnight with tritiated thymidine. (3HT). Proliferation is detected by the uptake of 3HT. The results, as given in Table 3 below, are expressed as the mean CPM as recorded by a Beta plate reader.

TABLE 3

Inhibition of Primary Allogeneic MLR by LO-CD2a and LO-CD2aHu

| Additions to Culture | Mean CPM |
| --- | --- |
| No antibody | 70,636 |
| LO-CD2a | 32,519 |
| LO-CD2aHu | 27,385 |
| Rat IgG2b | 90,859 |
| Human IgG1 | 88,267 |
| Autologous cells only | 1,759 |
| Stimulator cells only | 115 |

Figure 36:
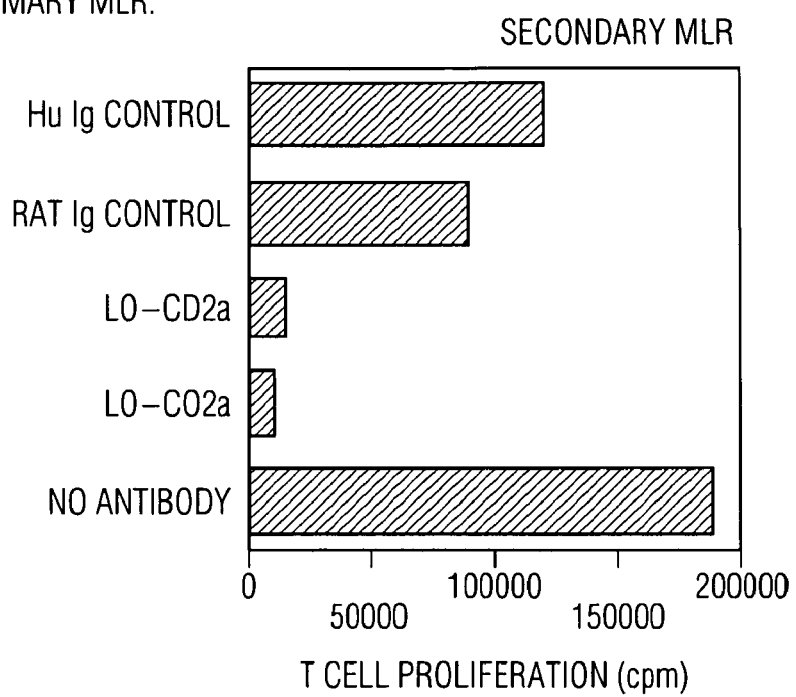

The humanized antibody also induces a hyporesponsive state to challenge with alloantigen in T cells (as measured by uptake of 3HT as mean CPM) when those T cells are cultured in a primary MLR in the presence of alloantigen and humanized LO-CD2a but not when an isotype control (with irrelevant specificity) is substituted for the humanized antibody (FIG. 36). The functional properties of the humanized antibody are similar to those of the rat LO-CD2a.

EXAMPLE 8

LO-CD2a Elicits Alloantigen Specific Hyporesponsiveness

The ability of T cells to recognize alloantigen in a secondary MLR following LO-CD2a addition only to the primary culture was examined. Primary MLR cultures contained responder cells and irradiated stimulator cells in the presence of either LO-CD2a, control antibody (LO-DNP11, Biotranplant, Inc., Charlestown, Mass.), or no antibody, and were incubated for 7 days. Cells were then washed and rested in media alone for 3 additional days. After the rest period, cultured cells were re-challenged with the original stimulator cells or cells obtained from a different donor ("third party" cells).

Figure 37:
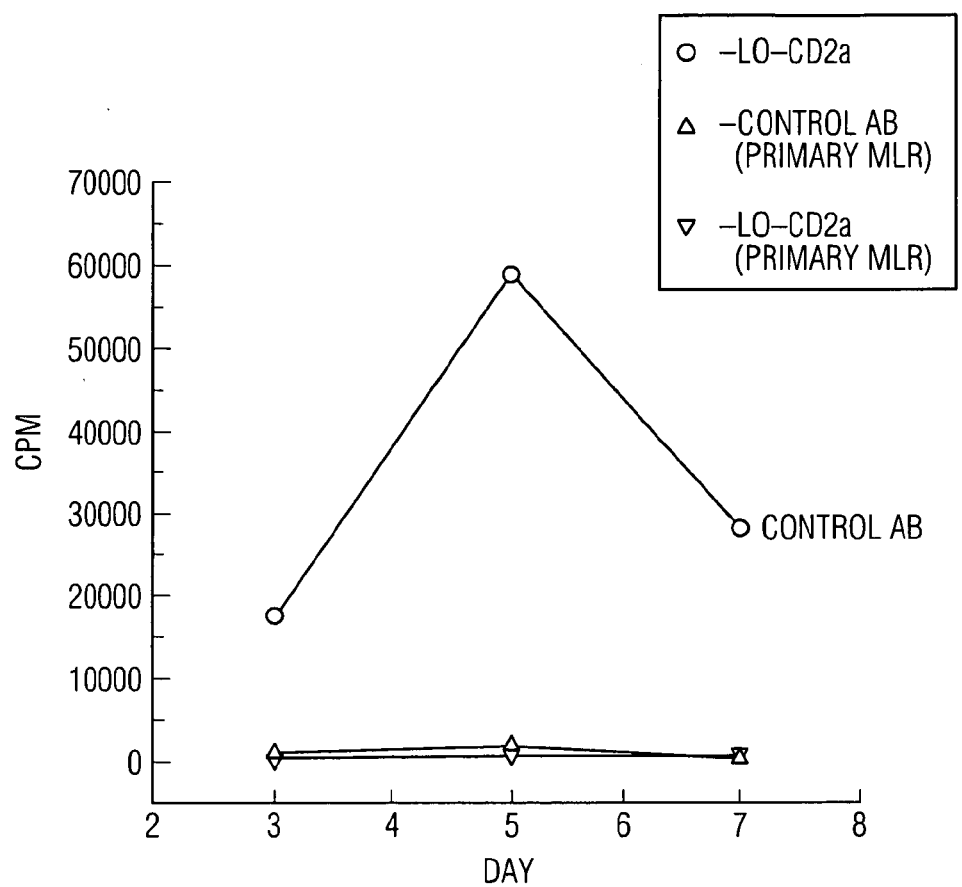

Results of a representative experiment from these studies are illustrated in FIG. 37. In Panel A, a primary response was observed when responder cells were cultured in the presence of control antibody at 200 ng/ml but when cells were cultured in the presence of LO-CD2a at 200 ng/ml no response was observed, consistent with previously reported data. The kinetics of the response were determined by harvesting cultures at days 3, 5, and 7. Data were presented as mean values of triplicate wells run at each data point in which the cpm from individual wells were within 10% of the mean.

As depicted in FIG. 37B, responder cells from cultures treated either with LO-CD2a or control antibody were rechallenged with alloantigen bearing stimulator cells at a 1:1 ratio without any antibody present in the secondary MLR. The kinetics of the response were determined by harvesting cultures at days 3, 5, and 7. The response of the cells cultured in primary MLR with either LO-CD2a or control antibody is included as a control. Data are presented as mean values of triplicate wells run at each data point in which the cpm from individual wells was within 10% of the mean. The data are from the same experiment depicted in FIG. 37A.

As shown in FIG. 37C, cells stimulated in a primary MLR with a specific alloantigen in the presence of LO-CD2a or control antibody then were challenged with alloantigen bearing cells from a third-party donor at a 1:1 ratio without any antibody present in the secondary culture. The kinetics of the response were determined by harvesting cultures at days 3, 5, and 7. The response of cells to autologous stimulator cells cultured in the primary MLR with control antibody or LO-CD2a is included as a control. The data are presented as mean values of triplicate wells run at each data point in which the cpm from individual wells were within 10% of the mean. The data are from the same experiment as depicted in FIGS. 37A and B.

Cells cultured in the presence of control antibody in the primary culture were responsive to re-challenge by the same allogeneic stimulator cells as those in the primary culture (Panel B) and were also responsive to stimulation by third-party cells (Panel C). In contrast, cells cultured in the presence of LO-CD2a during the primary MLR were not responsive either to rechallenge with the primary allogeneic stimulator cells (Panel B) or stimulation by third-party cells (Panel C). The cells in the cultures containing LO-CD2a were viable and responsive to stimuli other than alloantigen. For example, stimulation by either PHA or soluble OKT3 evoked equivalent proliferative responses in cells cultured with LO-CD2a control antibody, or with fresh autologous PBMC (data not shown). Flow cytometric analysis of these cells after rest failed to detect LO-CD2a on the cell surface (data not shown). Thus, these data indicate that exposure to LO-CD2a and alloantigen can induce a state of subsequent alloantigen hyporesponsiveness, i.e., tolerance.

To address the apparent alloantigen specificity of the hyporesponsiveness induced by LO-CD2a during alloantigen stimulation, cells obtained from cultures after alloantigen stimulation were challenged to respond to the soluble protein antigen, tetanus toxoid. Soluble antigen responses require the presence of viable antigen presenting cells (APC), which are depleted in alloantigen stimulated cultures after 7 days. Therefore, in these studies, a fresh source of APC was provided to the cultured cells by adding irradiated autologous PBMC to the secondary assay culture. As depicted in FIG. 38A, responder cells from cultures treated with either LO-CD2a or control antibody were rechallenged with alloantigen bearing stimulator cells at a 1:1 ratio without any antibody present in the secondary MLR. The kinetics of the response were determined by harvesting cultures at days 3, 5, and 7. The response of cells to autologous stimulator cells cultured in primary MLR with either LO-CD2a or control antibody also is included as a control. The data are presented as mean values of triplicate wells run at each data point in which cpm from individual wells were within 10% of the mean.

As depicted in FIG. 38B, responder cells from cultures treated with either LO-CD2a or control antibody were rechallenged with 7.5 ig/ml tetanus toxoid without any antibody present in secondary cultures. The kinetics of the response were determined by harvesting cultures at days 3, 5, and 7. The response of cells cultured in primary cultures with no antibody and autologous stimulator cells served as a control for response to tetanus toxoid.

The results shown in FIGS. 38A and B demonstrate that although cells cultured with LO-CD2a plus alloantigen in a primary MLR were hyposensitive to alloantigen in a secondary MLR, the cells were responsive to tetanus toxoid when presented by fresh APC.

EXAMPLE 9

To address the role of the Fc portion of LO-CD2a, studies were performed to compare the functional effects of the F(ab')$_2$ fragment with the whole antibody.

Figure 39:
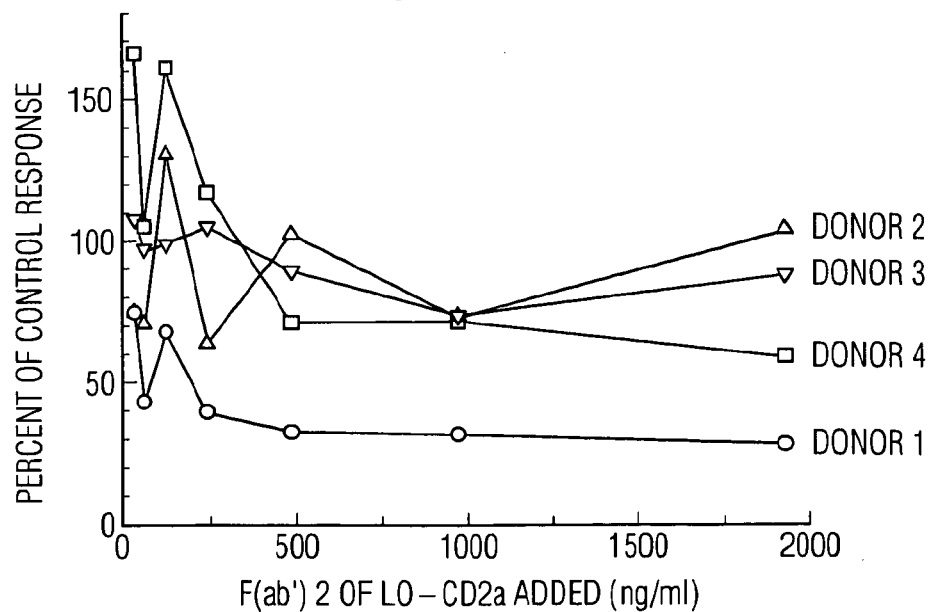

As shown in FIG. 39, PBMC were cultured for 6 days with irradiated Epstein-Barr Virus (EBV) transformed B cell line at a 2:1 responder to stimulator ratio and increasing doses of LO-CD2a or its F(ab')$_2$ fragment. The graph depicts the effect of F(ab')$_2$ fragment on the response of four different donors, and each point is a mean value of triplicate wells run at each data point. The results are reported as a percent of control response. For clarity on the graph, the data from the addition of the whole LO-CD2a antibody are not displayed. At a dose of 30 ng/ml of whole LO-CD2a, the responses of the donors were: donor 1-18%; donor 2-6.6%; donor 3-3.7%; and donor 4-12% of control. The cellular responses without antibody present from the individuals tested had mean values which ranged from 56,690 to 404,843 cpm, and the cpm from individual wells were within 10% of the mean.

Figure 40:
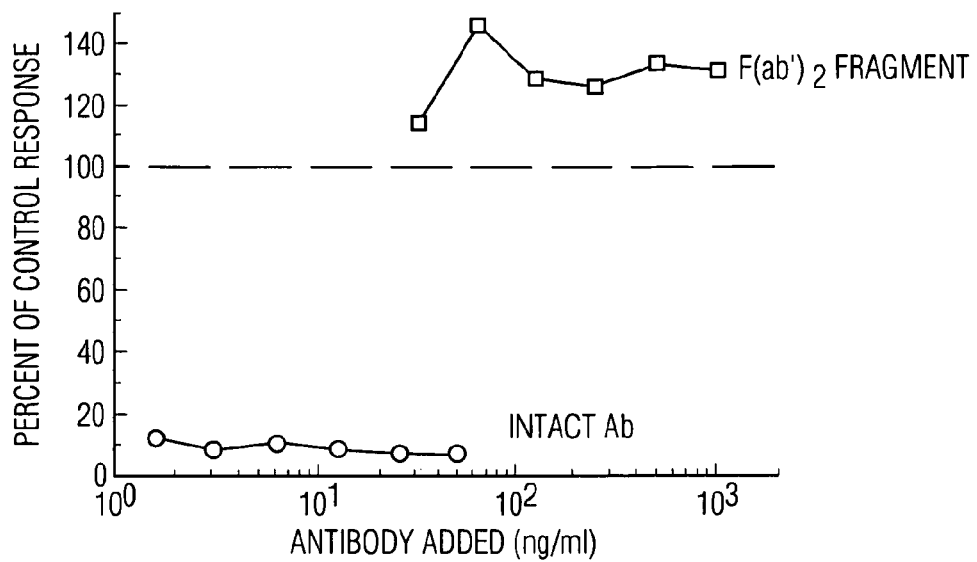

In order to evaluate further the potential inhibitory properties of the F(ab')$_2$ fragment, a dose titration of the F(ab')$_2$ fragment was added to unfractionated PBMC stimulated with soluble OKT3 (an APC-dependent response). As depicted in FIG. 40, PBMC were stimulated with soluble OKT3 (100 ng/ml) for 3 days. Either intact antibody or the F(ab')$_2$ fragment of LO-CD2a was added at day 0 at increasing doses. The results are expressed as percent of the proliferative response of the cells to OKT3 in the presence of an isotype matched control monoclonal antibody. Each data point is a mean of triplicate wells in which the cpm from individual wells were within 10% of the mean. The mean cpm for stimulated PBMC without antibody was 60,117.

The results in FIG. 40 show that T-cell proliferation to OKT3 was not inhibited when the F(ab')$_2$ fragment was used.

EXAMPLE 10

APC are Required for the Inhibitory Properties of LO-Cd2a in In Vitro Cultures

Figure 41:
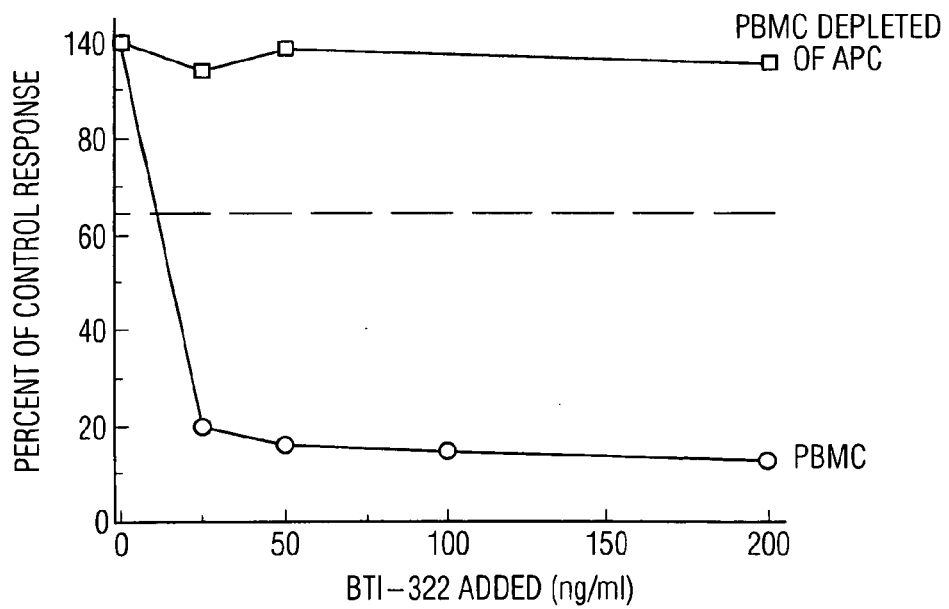

To address the question of the role of APC in the inhibitory properties of LO-CD2a, the T cell population of the PBMC was depleted of CD14, CD56, CD19 and HLA-DR positive cells by immunomagnetic selection. Analysis by flow cytometric techniques of the purified cells demonstrated that the APC population was depleted by >95% (data not shown). Proliferation of these purified T cells to soluble OKT3 (an APC dependent response) was reduced to <1% of the proliferation of unfractionated PBMC by this depletion (data not shown). Purified T cells or unfractionated PBMC were stimulated by plate bound OKT3 (an APC independent method of T cell stimulation) in the presence of absence of LO-CD2a. The ability of LO-CD2a to inhibit T cell activation was eliminated when APC were removed (FIG. 41). As shown in FIG. 41, PBMC or PBMC depleted of APC by immunomagnetic techniques were plated in 96 well plates coated with OKT3 (10 ìg/ml) and cultured for 3 days. LO-CD2a was added at the initiation of the cultures. The results are expressed as a percent of the proliferative response of the cells to OKT3 in the presence of an isotype matched control monoclonal antibody. The plotted data are representative of three experiments, wherein each data point is the mean of triplicate wells in which the cpm from individual wells were within 10% of the mean.

Numerous modifications and variations of the present invention are possible in light of the above teachings and, therefore, within the scope of the appended claims, the invention may be practiced otherwise than as particularly described.

The invention claimed is:

1. A composition, comprising:
   (a) an antibody produced by the cell line deposited as ATCC HB11423; and
   (b) a pharmaceutically acceptable carrier, wherein said antibody is present in said composition in an amount effective to inhibit a T-cell mediated immune response.

2. The composition of claim 1 wherein said antibody is present in said composition in an amount effective to elicit alloantigen specific hyporesponsiveness.

* * * * *